(12) United States Patent
Henno

(10) Patent No.: US 12,291,574 B2
(45) Date of Patent: *May 6, 2025

(54) POOLED NK CELLS FROM UMBILICAL CORD BLOOD ASSOCIATED WITH ANTIBODIES AND THEIR USES FOR THE TREATMENT OF DISEASE

(71) Applicant: EMERCELL SAS, Saint Mathieu-de-Treviers (FR)

(72) Inventor: Patrick Henno, Saint Mathieu-de-Treviers (FR)

(73) Assignee: EMERCELL SAS, Saint Mathieu-de-Treviers (FR)

( * ) Notice: Subject to any disclaimer, the term of this patent is extended or adjusted under 35 U.S.C. 154(b) by 623 days.

This patent is subject to a terminal disclaimer.

(21) Appl. No.: 17/500,874

(22) Filed: Oct. 13, 2021

(65) Prior Publication Data

US 2022/0096554 A1 Mar. 31, 2022

Related U.S. Application Data

(63) Continuation of application No. 15/458,680, filed on Mar. 14, 2017, now abandoned, which is a continuation-in-part of application No. PCT/EP2016/071470, filed on Sep. 12, 2016.

(30) Foreign Application Priority Data

Sep. 11, 2015 (EP) .................................... 15306403

(51) Int. Cl.
| | |
|---|---|
| *C07K 16/32* | (2006.01) |
| *A61K 39/00* | (2006.01) |
| *A61K 39/395* | (2006.01) |
| *C07K 16/28* | (2006.01) |
| *C07K 16/30* | (2006.01) |
| *C12N 5/0783* | (2010.01) |

(52) U.S. Cl.
CPC ...... *C07K 16/2887* (2013.01); *A61K 39/3955* (2013.01); *A61K 39/4613* (2023.05); *A61K 39/464424* (2023.05); *C07K 16/30* (2013.01); *C07K 16/3069* (2013.01); *C07K 16/32* (2013.01); *C12N 5/0646* (2013.01); *C07K 2317/21* (2013.01); *C07K 2317/24* (2013.01); *C07K 2317/732* (2013.01); *C07K 2317/734* (2013.01); *C07K 2317/92* (2013.01)

(58) Field of Classification Search
CPC ................ A61K 35/17; A61K 39/3955; A61K 39/4613; C07K 16/2887; C07K 16/30; C07K 16/32; C07K 2317/21; C07K 2317/24; C07K 2317/732; C07K 2317/734; C12N 5/0646
USPC ........................................................ 424/133.1
See application file for complete search history.

(56) References Cited

U.S. PATENT DOCUMENTS

2015/0225697 A1 * 8/2015 Law ........................ A61K 35/17
435/372

FOREIGN PATENT DOCUMENTS

| WO | WO-2005009466 A1 * | 2/2005 | ............. A61K 35/17 |
| WO | WO-2012146702 A1 * | 11/2012 | ............. A61K 35/17 |

* cited by examiner

*Primary Examiner* — Yan Xiao
(74) *Attorney, Agent, or Firm* — Arrigo, Lee, Guttman & Mouta-Bellum, LLP; Carla Mouta-Bellum

(57) ABSTRACT

The invention relates to the field of cell therapy, particularly NK cell mediated therapy associated with antibodies. The present invention is directed to methods and compositions for increasing the efficiency of therapeutic natural killer cells (NK cells) and/or antibodies, wherein said methods or compositions comprise the use of pooled NK cells from umbilical cord blood units (UCBs), preferably alloreactive NK cells, in combination with a therapeutic antibody in order to enhance the efficiency of the treatment in human subjects, in particularly through an increase in antibody-dependent cell-mediated cytotoxicity (ADCC) mechanism. The present invention relates to said composition as a pharmaceutical composition, preferably for its use for the treatment of a disease in a human subject in need thereof, preferably wherein said disease is a cancer, infectious or immune disease. Finally, the present invention is also directed to a method of treatment of a disease in a human subject in need thereof, comprising the administering to said subject said pooled NK cells from UCBs, preferably alloreactive, in combination with a therapeutic antibody which can be bound to said NK cells.

17 Claims, 29 Drawing Sheets

FIG. 12A
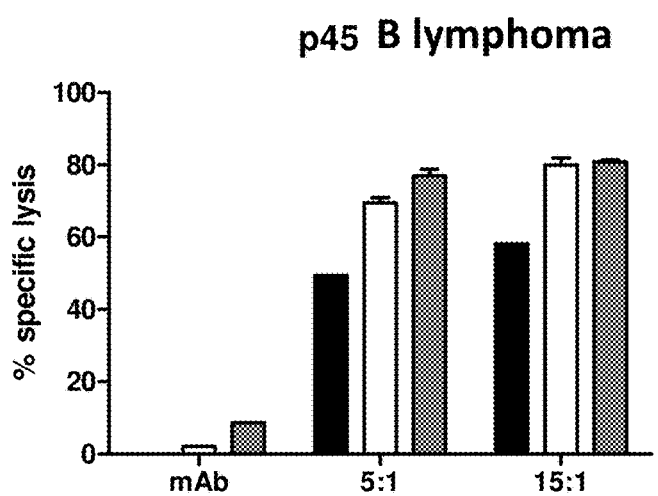
FIG. 12B
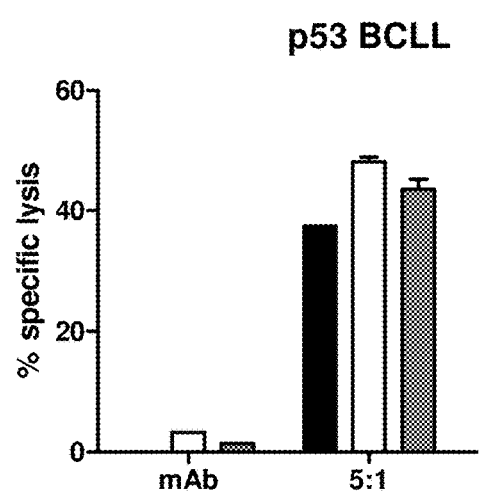
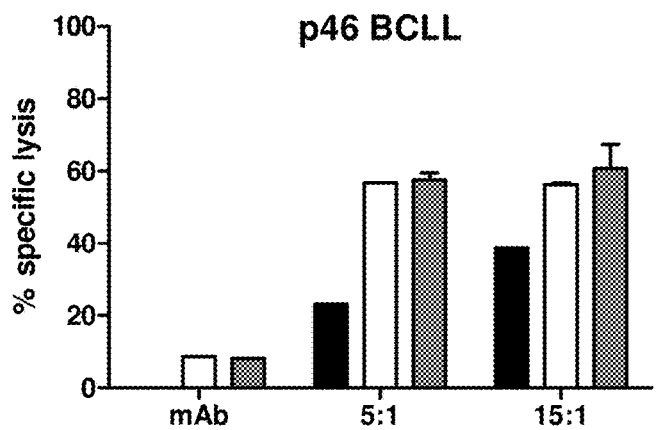
FIG. 12C

FIG. 13A
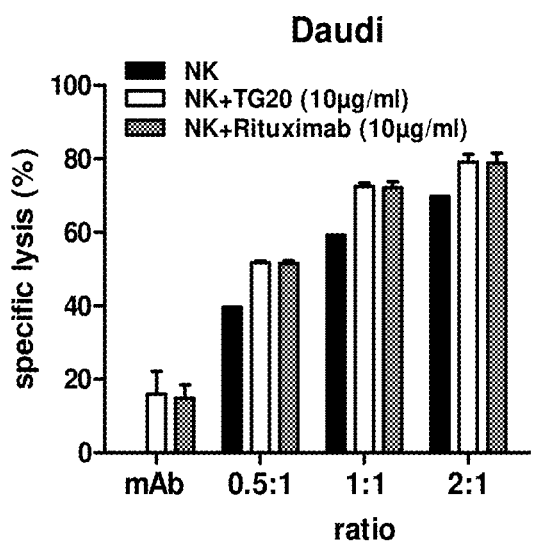
FIG. 13B
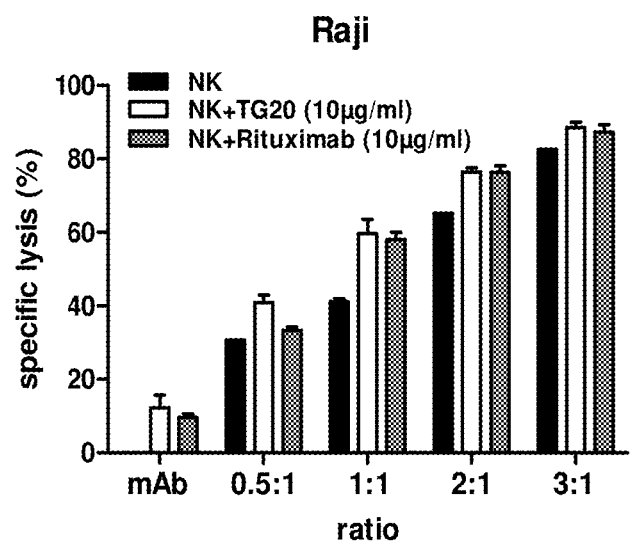
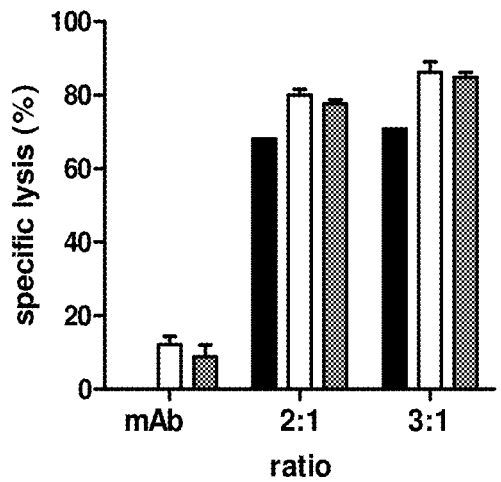
FIG. 13C
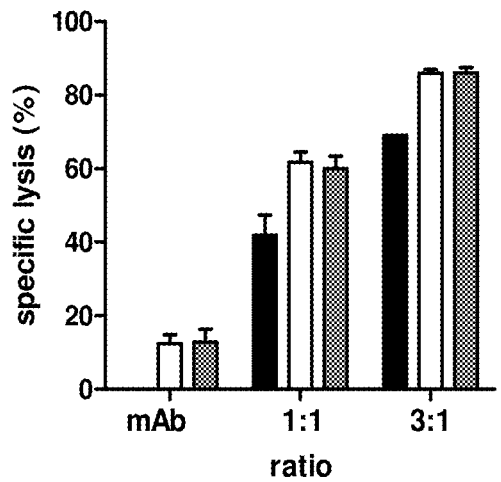
FIG. 13D

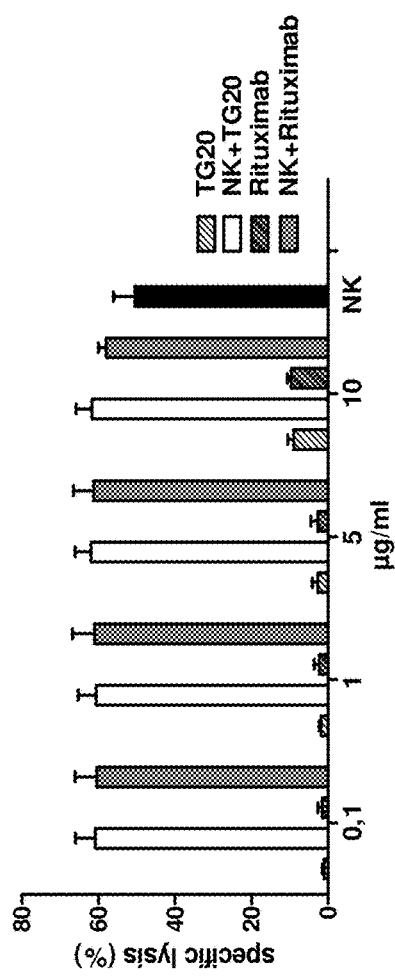
FIG. 14A
FIG. 14B
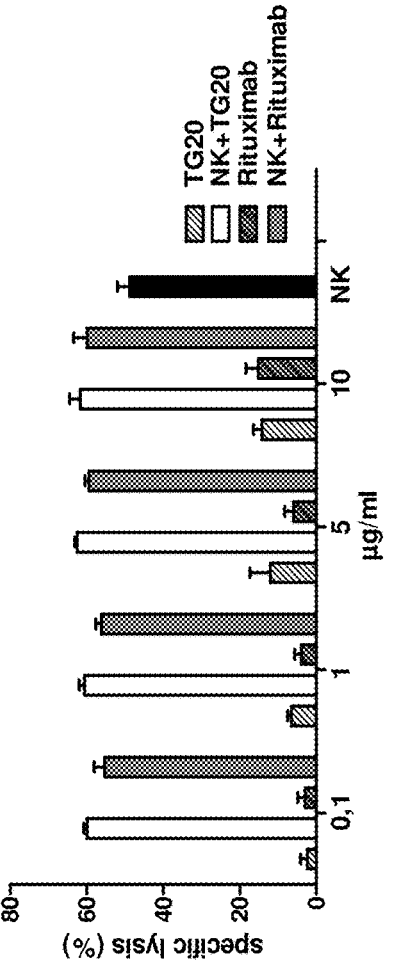
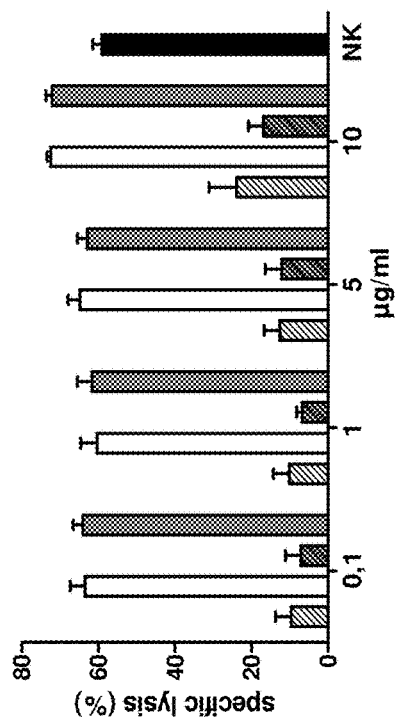
FIG. 14C
FIG. 14D
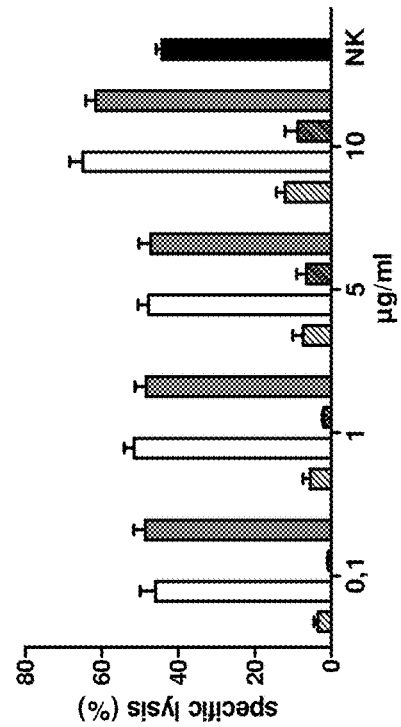

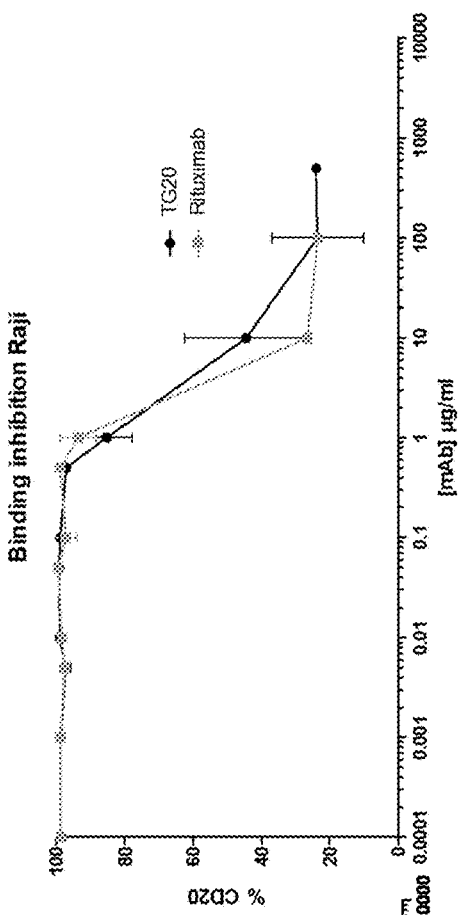
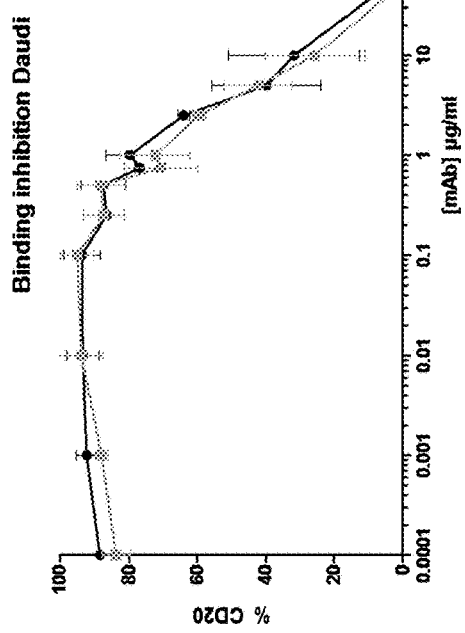
FIG. 22B
FIG. 22A

POOLED NK CELLS FROM UMBILICAL CORD BLOOD ASSOCIATED WITH ANTIBODIES AND THEIR USES FOR THE TREATMENT OF DISEASE

CROSS-REFERENCE TO RELATED APPLICATIONS

This application is a continuation of U.S. application Ser. No. 15/458,680, filed Mar. 14, 2017, which is a continuation in-part of PCT/EP2016/071470, filed Sep. 12, 2016, which claims the benefit of priority of European Patent Application 15306403.5, filed Sep. 11, 2015.

The invention relates to the field of cell therapy, particularly NK cell mediated therapy associated with antibodies. The present invention is directed to methods and compositions for increasing the efficiency of therapeutic natural killer cells (NK cells) and/or antibodies, wherein said methods or compositions comprise the use of pooled NK cells from umbilical cord blood units (UCBs), preferably alloreactive NK cells, in combination with a therapeutic antibody in order to enhance the efficiency of the treatment in human subjects, in particularly through an increase in antibody-dependent cell-mediated cytotoxicity (ADCC) mechanism. The present invention relates to said composition as a pharmaceutical composition, preferably for its use for the treatment of a disease in a human subject in need thereof, preferably wherein said disease is a cancer, infectious or immune disease. Finally, the present invention is also directed to a method of treatment of a disease in a human subject in need thereof, comprising the administering to said subject said pooled NK cells from UCBs, preferably alloreactive, in combination with a therapeutic antibody which can be bound to said NK cells.

NK cell effector functions can be exploited for the treatment of some tumors through their ability to mediate ADCC. NK cell recognition of an antibody-coated target cell, particularly by recognizing the NK cell Fc receptor, CD16 (FcγRIIIa), results in rapid NK cell activation and degranulation.

Different therapeutic strategies based on the use of therapeutic antibodies have been developed to deplete target cells, particularly diseased cells such as virally-infected cells, tumor cells or other pathogenic cells. This includes, for instance, the use of therapeutic Monoclonal antibodies (mAbs) that specifically target tumor cells take advantage of the ADCC effector pathway to tip the balance of an interrogating NK cell in the favor of the activating receptors resulting in tumor cell destruction and an anti-tumor immune response (K. L. Anderson et al., Journal of Biomedicine and Biotechnology, Volume 2011 (2011), Article ID 379123, 7 pages).

Tumor-targeted mAbs that initiate NK cell ADCC have been used clinically. Among these mAbs, we can cited here the antibodies targeting CD20 (such as Rituximab or Ublituximab), Her2/neu (such as Trastuzumab or Pertuzumab), epidermal growth factor receptor (EGFR) (such as Cetuximab or Matuzumab), CD52 (such as alemtuzumab) and disialoganglioside (GD2) (such as Dinutuximab) are examples of clinically successful or in clinal trial antibodies whose mechanisms include NK cell-mediated ADCC. Additional examples of therapeutic antibodies under development are disclosed in the art.

Natural Killer (NK) cells are a fundamental component of the innate immune system. They are capable of recognizing and destroying tumor cells as well as cells that have been infected by viruses or bacteria (Lanier L L, 2008; Nat Immunol 9: 495-502).

Identification and characterization of NK cell receptors and their ligands over the last two decades have shed light on the molecular mechanisms of NK cell activation by tumor cells. The finding of inhibitory receptors supported the 'Missing self' hypothesis proposed by Karre whose pioneering work showed that NK cells killed tumor cells that lacked major histocompatibility complex (MHC) class-I molecule. The inhibitory receptors recognize MHC class I molecules whereas, the activating receptors recognize a wide variety of ligands (P. A. Mathew, J Cell Sci Ther, Volume 3, Issue 7).

NK cells are responsible of the graft versus leukemia (GvL) effect with minimal GvH (Graft versus Host) and HvG (Host versus Graft) effects, pointing attention to the development of immunotherapies involving NK cells. Data from several laboratories suggest that exploiting NK cell alloreactivity could have a large beneficial independently of NK cell source. Mismatched transplantation triggers alloreactivity mediated by NK cells, which is based upon "missing self recognition". Donor-versus-recipient NK cell alloreactions are generated between individuals who are mismatched for HLA-C allele groups, the HLA-Bw4 group and/or HLA-A3/11. KIR ligand mismatching is a prerequisite for NK cell alloreactivity because in 20 donor-recipient pairs that were not KIR ligand mismatched in the graft-versus-host direction, no donor alloreactive NK clones were found.

Another interesting point with NK cells is that even if NK cells also recognize the self-identity molecules (HLA molecules) mainly with their inhibitory receptors, they are activated through a complex equilibrium of activating signal and inhibiting signal and need the activating signal expressed only by infected, abnormal or tumoral cells to kill the cells. Then donor selection is easier because with NK cells alone donor and patient don't need to express quite exactly the same major HLA alleles (HLA match >4/6 for total umbilical cord blood (UCB) graft for example). In contrast, NK expressing inhibitory receptors when the recipient doesn't express the corresponding HLA (absence of inhibitory signal=iKIR-HLA mismatch) lead to better tumor killing without leading to GvHD.

Even if NK cells have a natural cytotoxic potential, their cytotoxic activity can be improved in vitro by different activation mechanisms, and most of these mechanisms are also able to amplify NK cells (with variable amplification factors) leading to more therapeutic cells, more efficient.

Finding a good way to amplify/activate NK cells is important to improve the therapeutic potential of these cells (quantity and potency).

In vitro activation protocols include cytokines and growth factor use, such as IL-2, IL-15, IL-18, IL-21, SCF, Flt3-L ( . . . ) with or without accessory cells such as peripheral blood mononuclear cells, tumoral cells or cell lines (see M. Villalba Gonzales et al., WO2009/141729). Using accessory cells presenting a particular iKIR-HLA mismatch (4 major iKIR-HLA mismatch: HLA A3/A11; HLA Bw4; HLA C1; HLA C2 and associated iKIR receptors).

Umbilical cord blood (UCB) has been shown to be a good source of NK cells, with higher NK cells percentages and good in vivo expansion/activation (see M. Villalba Gonzales et al., WO2012/146702).

The depletion of cells bearing the antigen specifically recognized by the antibody can be mediated through the mechanism of ADCC, complement dependent lysis, and direct antitumor inhibition of tumor growth through signal given via the receptor targeted by the antibody. These antibodies which represent a novel efficient approach to human therapy, particularly for treatment of tumors, do not always exhibit alone a strong efficacy. For example, while rituximab, alone or in combination with chemotherapy was shown to be effective in the treatment of certain Non-Hodgkin's Lymphoma (NHL) grades, a significant % of patients with low grade NHL can exhibit low clinical response using rituximab.

There is therefore a need in the art for increasing the efficiency of the therapeutic antibodies.

Novel approaches to enhance the efficacy of the therapeutic antibodies have been disclosed. Some of these approaches are based on the increase of the ADCC mechanism in vivo, when therapeutic antibodies are administrating in combination of alloreactive natural killer (NK) cells.

For this approach, UCB unit can be used to provide the desired NK cells contained in one UCB unit. Nevertheless, and despite the possibility to amplify and activate the NK cells contained in one UCB unit with a good rate of amplification, it is will be desirable to provide these NK cells product, for clinical therapies, available, purity, with high expansion rates and activation state and exhibiting NK cells cytotoxic activity.

In addition, it would be desirable that such method based on the administrating of alloreactive natural killer (NK) cells from UCB unit in combination simultaneously, separately or sequentially with therapeutic antibodies, can be carried out from a large quantity of cells, particularly activated NK cells, in a same batch (production lot), expected to treat at least more than 1, preferably, 50, more preferably around 100 patients, therapeutic agents needing to show less variability as possible for said cells.

To this end, it would be desirable to provide a method which offers the ability to obtain in a same lot of production, a large quantity of specific enriched cell populations, with a cell-manufacturing process which complies with the good manufacturing practice (cGMP), commercial-scale production and chemistry, manufacturing and controls standards of regulatory agencies.

This is the object of the present invention.

For the first time, and in a surprising manner, the Applicant succeeded in implementing a method allowing the enhance of the ADCC efficacy of a therapeutic antibody by combining said antibody with alloreactive human amplified and/or activated NK cells in which said amplified and/or activated NK cells have been obtained from a pooled UCB units.

The inventors demonstrate here that the efficiency of a therapeutic antibody can be greatly enhanced by the co-injection/administrating of selected, alloreactive amplifying/activating and pooling UCB NK cells from different donors and said therapeutic antibody.

According to a first embodiment, the present invention relates to a pharmaceutical composition comprising a therapeutic antibody, which can be bound by a natural killer cells (NK cells), preferably by a Fc receptor, and a population of natural killer cells (NK cells), preferably alloreactive NK cells, wherein said cells population is obtained by a method comprising the steps of:
(a) providing at least n umbilical cord blood units (UCB units), or fraction thereof containing said NK cells, with n≥2, preferably 3≤n≤50; and
(b) pooling said at least n UCB units, or fraction thereof containing said NK cells, to produce said population of NK cells.

In a preferred embodiment, said composition containing said therapeutic antibody and said NK cells population according to the present invention is a composition or a product as a combined preparation for simultaneous, separate or sequential use.

In a preferred embodiment, said therapeutic antibody of said composition according to the present invention is a monoclonal antibody or a fragment thereof capable to bind said NK cells Fc receptor, and wherein said monoclonal antibody, or fragment thereof, comprises at least the 6 complement determining regions (CDRs) of the heavy and the light chain of said antibody specific of the antigen of the subject cell which is desired to target.

In a preferred embodiment, said NK cells Fc receptor of said composition according to the present invention said NK cells Fc receptor is the FcγRIIIa receptor (CD16).

In a preferred embodiment, said therapeutic antibody of said composition according to the present invention is an antibody whose mechanisms include NK cell-mediated ADCC, preferably selecting from the group consisting of an anti-CD20, an anti-Her2/neu, an anti-epidermal growth factor receptor (EGFR), and an anti-ganglioside GD2 antibody (anti-GD2).

In a preferred embodiment, said therapeutic antibody of said composition according to the present invention is a human, humanized or chimeric antibody or a fragment thereof, more preferably a recombinant monoclonal antibody.

More preferred are glycoengineered antibodies exhibiting low fucosylated or non fucosylated (or afucosylated) IgG Fc domain, known to increase ADCC activity.

In a preferred embodiment, said therapeutic antibody of said composition according to the present invention is selected from the group of:
Anti-CD20
Rituximab, Ublituximab (also called TG20, TGR-1101), Obinutuzumab, Ocaratuzumab, Ocrelizumab, Odulimomab, Ofatumumab, Tositumomab, Veltuzumab, FBTA05 or Ibritumomab tiuxetan;
Anti-HER2/Neu
Trastuzumab, Ertumaxomab, Pertuzumab and Herceptin-Like from LFB-US;
Anti-EGFR
Cetuximab, Futuximab, Imgatuzumab, Matuzumab, Necitumumab or Nimotuzumab;
Anti-GD2
Dinutuximab; and
Anti-CD52
Alemtuzumab.

In a more preferred embodiment, said therapeutic antibody of said composition according to the present invention is selected from the group consisting of anti-CD20 and anti-HER2/neu antibodies, preferably low or afucosylated monoclonal anti-CD20 and anti-HER2/neu antibodies.

Ublituximab R603 LFB and TG20 LFB US which are low/afucosylated recombinant monoclonal antibodies are the more preferred anti-CD20 monoclonal antibodies.

Trastuzumab and Herceptin-like are the more preferred anti-HER2/Neu antibodies, Herceptin-like which is a low/non-fucosylated antibody being the most preferred.

Additional examples of therapeutic antibodies whose mechanisms include NK cell-mediated ADCC are well known by the skilled person and disclosed in the art, and is part of the present list of therapeutic antibodies and thus comprised in the present invention.

In a preferred embodiment the therapeutic antibody is not coated at the surface of the NK cells before its administration.

In another embodiment the therapeutic antibody is binding at the surface of the NK cells via the binding between its Fc portion and the CD16 receptor presents at the surface of the NK cells.

The terms "antibody" or "antibodies" are used interchangeably in the broadest sense and include monoclonal antibodies (e.g., full length or intact monoclonal antibodies), polyclonal antibodies, multivalent antibodies or multispecific antibodies (e.g., bispecific antibodies so long as they exhibit the desired biological activity).

More particularly, such molecule consists in a glycoprotein comprising at least two heavy (H) chains and two light (L) chains inter-connected by disulfide bonds. Each heavy chain is comprised of a heavy chain variable region (or domain) (VH) and a heavy chain constant region. The heavy chain constant region is comprised of three domains, CH1, CH2 and CH3. Each light chain is comprised of a light chain variable region (VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

The heavy chains of immunoglobulins can be divided into three functional regions: the Fd region, the hinge region, and the Fc region (crystallizable fragment). The Fd region comprises the VH and CH1 domains and, in combination with the light chain, forms Fab—the antigen-binding fragment. The Fc fragment is responsible for the immunoglobulin effector functions, which includes, for example, complement fixation and binding to cognate Fc receptors of effector cells. The hinge region, found in IgG, IgA, and IgD immunoglobulin classes, acts as a flexible spacer that allows the Fab portion to move freely in space relative to the Fc region.

The term «Monoclonal Antibody» is used in accordance with its ordinary meaning to denote an antibody obtained from a population of substantially homogeneous antibodies, i.e. the individual antibodies comprising the population are identical except for possible naturally occurring mutations that may be present in minor amounts. In other words, a monoclonal antibody consists in a homogenous antibody resulting from the proliferation of a single clone of cells (e.g., hybridoma cells, eukaryotic host cells transfected with DNA encoding the homogenous antibody, prokaryotic host cells transformed with DNA encoding the homogenous antibody, etc.), and which is generally characterized by heavy chains of a single class and subclass, and light chains of a single type. Monoclonal antibodies are highly specific, being directed against a single antigen. Furthermore, in contrast to polyclonal antibodies preparations that typically include different antibodies directed against different determinants, or epitope, each monoclonal antibody is directed against a single determinant on the antigen.

In a second aspect, in the composition according to the present invention,
  i) said cells population of NK cells is obtained by a method further comprising the step of: (c) depleting the T cells contained in the pool obtained in step (b); or
  ii) said cells population of NK cells is obtained by a method comprising the step of depleting the T cells contained in each of the n UCB units before the step (b) of pooling.

In a preferred embodiment, in the composition according to the present invention, said cells population of NK cells is obtained by a method wherein said n UCB units when pooled present the same pattern for major HLA class I groups genotype, preferably wherein each HLA group present in the pooled n UCB is recognized by the same major inhibitory KIR by NK cells.

In another preferred embodiment, in the composition according to the present invention, said cells population of NK cells is obtained by a method wherein said major HLA class I group is selected from the group consisting of HLA A3/A11 which is recognized by KIR3DL2, HLA Bw4, which recognized by KIR3DL1, HLA C group 1 which is recognized by KIR2DL2/3 and HLA C group 2 which is recognized by KIR2DL1.

In another preferred embodiment, in the composition according to the present invention, said population of NK cells is obtained by a method comprising further a method of expanding said population of NK cells from cells contained in said n UCB units, and wherein,
  optionally each UCB units has been preliminary and separately expanded for said NK cells before the step of pooling said at least n UCB units; and/or
  expanding the desired cells obtained from the population of cells obtained after the step of pooling said at least n UCB units in a suitable medium to produce said expanded population of desired cells.

In another preferred embodiment, in the composition according to the present invention, said population of NK cells is an activated population of NK cells, obtained by a method further comprising a step of activating said population of NK cells.

In another preferred embodiment, in the composition according to the present invention, said population of NK cells is an activated population of NK cells wherein:
  optionally each UCB units has been preliminary and separately expanded and activated for said NK cells before the step of pooling said at least n UCB units; and/or
  activating the desired cells obtained from the population of cells obtained after the step of pooling said at least n UCB units in a suitable medium to produce said activated population of desired cells.

In a third aspect, in the composition according to the present invention, said population of NK cells is obtained by a method selected in the group of methods consisting of:
  A) the method comprising the step of:
    i) providing at least n UCB units, or fraction thereof containing NK cells, with n≥2, preferably 3≤n≤50, and wherein said at least n UCB units present the same pattern for major HLA class I groups genotype, preferably wherein each HLA group present in the pooled n UCB is recognized by the same major inhibitory KIR by NK cells;
    ii) optionally red cell-/erythrocytes-depleting each UCB unit;

iii) optionally, the population of cells obtained in step i) or ii) is frozen, kept in liquid nitrogen and thawed before step iv);
iv) depleting the T cells contained in each UCB unit;
v) for each of the UCB units obtained in the preceding step, separately expand and, optionally, activate the NK cells contained in one UCB unit by contacting the NK cells contained in the UCB unit, or fraction thereof containing NK cells, in a suitable medium to produce said expanded population and, optionally, activated NK cells for each UCB unit, preferably during 3 to 28 days; and
vi) pooling the nUCB units cells obtained in the preceding step UCB units, or fraction thereof containing NK cells, to produce a population of pooled expanded and, optionally, activated NK cells.

B) the method comprising the step of:
i) providing at least n UCB units, or fraction thereof containing NK cells, with n≥2, preferably 3≤n≤50, and wherein said at least n UCB units present the same pattern for major HLA class I groups genotype, preferably wherein each HLA group present in the pooled n UCB is recognized by the same major inhibitory KIR by NK cells;
ii) optionally red cell-/erythrocytes-depleting each UCB unit;
iii) optionally, the population of cells obtained in step i) or ii) is frozen, kept in liquid nitrogen and thawed before step iv);
iv) for each of the UCB units obtained in the preceding step, separately expand and, optionally, activate the NK cells contained in one UCB unit by contacting the NK cells contained in the UCB unit, or fraction thereof containing NK cells, in a suitable medium to produce said expanded population and, optionally, activated NK cells for each UCB unit, preferably during 3 to 28 days;
v) pooling the nUCB units cells obtained in the preceding step UCB units, or fraction thereof containing NK cells, to produce a population of pooled expanded and, optionally, activated NK cells; and
vi) depleting the T cells contained in the pooled NK cells obtained after step v).

C) the method comprising the step of:
i) providing at least n UCB units, or fraction thereof containing NK cells, with n≥2, preferably 3≤n≤50, and wherein said at least n UCB units present the same pattern for major HLA class I groups genotype, preferably wherein each HLA group present in the pooled n UCB is recognized by the same major inhibitory KIR by NK cells;
ii) optionally red cell-/erythrocytes-depleting each UCB unit;
iii) optionally, the population of cells obtained in step i) or ii) is frozen, kept in liquid nitrogen and thawed before step iv);
iv) depleting the T cells contained in each UCB unit;
v) pooling the nUCB units cells obtained in the preceding step UCB units, or fraction thereof containing NK cells, to produce a population of pooled NK cells; and
vi) expanding and, optionally, activating the pooled NK cells obtained in the preceding step by contacting the NK cells contained in the pool, or fraction thereof containing NK cells, in a suitable medium to produce said population of pooled expanded and, optionally, activated NK cells, preferably the amplification factor for NK cells after the expanding step(s) is at least 100 or 300 for an expanding/activation step(s) total duration comprised between 9 and 28 days.

D) the method comprising the step of:
i) providing at least n UCB units, or fraction thereof containing NK cells, with n≥2, 3≤n≤50, and wherein said at least n UCB units present the same pattern for major HLA class I groups genotype, preferably wherein each HLA group present in the pooled n UCB is recognized by the same major inhibitory KIR by NK cells;
ii) optionally red cell-/erythrocytes-depleting each UCB unit, preferably by density gradient separation, more preferably by Ficoll-Paque® density gradient separation, or by a step of freezing and thawing;
iii) optionally, the population of cells obtained in step i) or ii) is frozen, kept in liquid nitrogen and thawed before step iv);
iv) pooling the nUCB units cells obtained in the preceding step UCB units, or fraction thereof containing NK cells, to produce a population of pooled NK cells;
v) depleting the T cells contained in the pooled NK cells obtained after step iv; and
vi) expanding and, optionally, activating the pooled NK cells obtained in the preceding step by contacting the NK cells contained in the pool, or fraction thereof containing NK cells, in a suitable medium to produce said population of pooled expanded and, optionally, activated NK cells, preferably the amplification factor for NK cells after the expanding step(s) is at least 100 or 300 for an expanding/activation step(s) total duration comprised between 9 and 28 days In a fourth aspect, in the composition according to the present invention, said population of activated NK cells is obtained by a method wherein, said suitable medium suitable to expand and to activate the NK cells comprised accessory cells and/or at least one suitable NK activated factor.

The present invention is also directed to a composition according to the present invention, for its use for the treatment or the prevention of a disease in a human subject in need thereof, preferably wherein said disease is a cancer, infectious or immune disease.

The present invention is also directed to a composition according to the present invention, for its use for the treatment or the prevention of a cancer wherein this cancer is selected from lymphoma B-CLL and NHL.

The present invention is also directed to a composition according to the present invention, for its use for the treatment or the prevention of a disease in a human subject in need thereof, wherein said therapeutic antibody and said alloreactive NK cells are administered into said subject simultaneously.

The present invention also relates to a method of treatment of a disease in a human subject in need thereof, comprising:
a) administering to said subject alloreactive pooled UCB units NK cells as described herein and,
b) administering to said subject a therapeutic antibody which can be bound by CD16.

In another aspect, the present invention is directed to method of increasing ADCC in a subject receiving therapeutic antibody treatment, wherein said antibody can be bound by CD16 and said method comprises administering to said subject prior to, simultaneously or after the administration of said therapeutic antibody an amount of alloreactive NK cells sufficient to increase ADCC, and wherein said alloreactive NK cells are obtained), wherein said NK cells population is obtained by a method comprising the steps of:
(a) providing at least n umbilical cord blood units (UCB units), or fraction thereof containing said NK cells, with n≥2, preferably 3≤n≤50; and
(b) pooling said at least n UCB units, or fraction thereof containing said NK cells, to produce said population of NK cells.

In a preferred embodiment of the composition or the method of the present invention, the pooled UCBs NK cells population is obtained by the preferred following methods or preferred embodiment as described below.

A method comprising the steps of:
(a) providing at least n umbilical cord blood units (UCB units), or fraction thereof containing said NK cells, with n≥2, preferably 3≤n≤50; and
(b) pooling said at least n UCB units, or fraction thereof containing said NK cells, to produce said population of NK cells.

More preferably, 3≤n≤5 and 3≤n≤25 being the most preferred.

In the context of the present invention, by "fraction of UCB unit containing said cells", it is intended to designate a fraction of the UCB unit containing at least the population of cells or part of said population which is desired to be produced.

In a preferred manner, said method further comprising the step of:
(c) depleting the T cells contained in the pool obtained in step (b).

According to another preferred embodiment, said method comprises a step of depleting the T cells contained in each of the n UCB units before the step (b) of pooling.

In a preferred embodiment, in said method, the n UCB units which are pooled in step b) present the same pattern for major HLA class I groups genotype.

In the present description, by "present the same pattern for major HLA class I groups genotype", it is intending to designate UCB units whose group of HLA molecules is recognized by the same inhibitory KIR or preferably wherein each HLA group present in the pooled n UCB is recognized by the same major inhibitory KIR by NK cells.

In another preferred embodiment of the method according each UCB present in the pooled n UCB belongs to a HLA group which is recognized by the same inhibitory KIR.

As used herein the term "KIR" or "inhibitory KIR" has its general meaning in the art and includes but is not limited to KIR2DL1, KIR2DL2, KIR2DL3, KIR3DL1 and KIR3DL2.

The main/major inhibitory KIRs are KIR2DL1, KIR2DL2, KIR2DL3, KIR3DL1 and KIR3DL2.

KIR2DL1 recognizes HLA-C w4 and related, 'group2' alleles. KIR2DL2 and KIR2DL3 recognize HLA-Cw3 and related, 'group 1' alleles. KIR3DL1 is the receptor for HLA-B allotypes with Bw4 motifs. Finally, KIR3DL2 is the receptor for HLA-A3/11.

In another preferred embodiment, said major HLA class I group is selected from the group consisting of HLA A3/A11 which is recognized by KIR3DL2, HLA Bw4, which recognized by KIR3DL1, HLA C group 1 which is recognized by KIR2DL2/3 and HLA C group 2 which is recognized by KIR2DL1.

A preferred source of UCB units are human UCB units.

In a particularly preferred embodiment, said source, is a source of frozen human UCB.

In a preferred embodiment, the method for producing an expanded population of cells from cells contained in n UCB units, comprising the step of:

(A) producing a population of cells from at least n UCB units, or fraction thereof containing said cells, by the method for producing a population of cells according to the present invention, optionally each UCB units has been preliminary and separately expanded for said cells before step A); and
(B) expanding the desired cells obtained from the population of cells obtained in step (A) in a suitable medium to produce said expanded population of desired cells.

In the method for producing an expanded population of cells from cells contained in n UCB units, the step (B) can be an optionally step in case of each UCB units has been preliminary and separately expanded for said cells before the step b) of pooling in step A).

In another preferred aspect, the method for producing a population of differentiated cells from desired cells contained in n UCB units, comprising the step of:
(A) producing a population of cells from said n UCB units, or fraction thereof containing said desired cells, by the method for producing a population of cells according to the present invention, optionally each UCB units has been preliminary and separately differentiated for said cells before step A); and
(B) differentiating the desired cells obtained from the preceding step in a suitable medium to produce said population of differentiated cells.

In the method of for producing a population of differentiated cells from cells contained in n UCB units, the step (B) of differentiating can be an optionally step in case of each UCB units has been preliminary and separately differentiated for said cells before the step b) of pooling in step A).

In another preferred aspect, the method for producing a population of cells containing activated natural killer (NK) cells, comprising:
(A) producing a population of cells containing activated NK cells from at least n UCB units, or fraction thereof containing said NK cells, by the method for producing a population of cells according to the present invention, optionally each UCB units has been preliminary and separately expanded for said NK cells before step A);
(B) activating said NK cells obtained from the step (A) in a suitable medium to produce said population of cells containing activated NK cells;
C) optionally, recovering said activated NK cells from said population.

In another preferred aspect, the method for producing a population of expanded activated NK cells, comprises:
(A) producing a population of cells containing NK cells from at least n UCB units, or fraction thereof containing said NK cells, by the method for producing a population of cells according to the present invention, optionally each UCB units has been preliminary and separately expanded and activated for said NK cells before step A);
(B) expanding and activating said NK cells obtained from the step (A) in a suitable medium to produce said population of expanded activated NK cells; and
(C) optionally, recovering said expanded activated NK cells.

In another preferred aspect, the method for producing a population of expanded, optionally, activated NK cells from n UCB units, comprises the step of:
i) providing at least n UCB units, or fraction thereof containing NK cells, with n≥2, preferably 2≤n≤100 or 3≤n≤50, more preferably 3≤n K 25, and wherein said at least n UCB units present the same pattern for major HLA class I groups genotype, preferably wherein each HLA group present in the pooled n UCB is recognized by the same major inhibitory KIR by NK cells;
ii) optionally red cell-/erythrocytes-depleting each UCB unit, preferably by density gradient separation, more preferably by Ficoll-Paque® density gradient separation, by the Hetastarch (Hydroxyethyl Starch; HES) method, by using the PrepaCyte® CB device or by a step of freezing and thawing;
iii) optionally, the population of cells obtained in step i) or ii) is frozen, kept in liquid nitrogen and thawed before step iv);
iv) depleting the T cells contained in each UCB unit;
v) for each of the UCB units obtained in the preceding step, separately expand and, optionally, activate the NK cells contained in one UCB unit by contacting the NK cells contained in the UCB unit, or fraction thereof containing NK cells, in a suitable medium to produce said expanded population and, optionally, activated NK cells for each UCB unit, preferably during 3 to 28 days;
vi) pooling the n UCB units cells obtained in the preceding step UCB units, or fraction thereof containing NK cells, to produce a population of pooled expanded and, optionally, activated NK cells.

In another preferred aspect, the method of producing a population of expanded and, optionally, activated NK cells from n UCB units, comprises the step of:
i) providing at least n UCB units, or fraction thereof containing NK cells, with n≥2, preferably 2≤n≤100 or 3≤n≤50, more preferably 3≤n≤25, and wherein said at least n UCB units present the same pattern for major HLA class I groups genotype, preferably wherein each HLA group present in the pooled n UCB is recognized by the same major inhibitory KIR by NK cells;
ii) optionally red cell-/erythrocytes-depleting each UCB unit, preferably by density gradient separation, more preferably by Ficoll-Paque® density gradient separation (type Ficoll-Paque PREMIUM®), by the Hetastarch (Hydroxyethyl Starch; HES) method, by using the PrepaCyte® CB device or by a step of freezing and thawing;
iii) optionally, the population of cells obtained in step i) or ii) is frozen, kept in liquid nitrogen and thawed before step iv);
iv) for each of the UCB units obtained in the preceding step, separately expand and, optionally, activate the NK cells contained in one UCB unit by contacting the NK cells contained in the UCB unit, or fraction thereof containing NK cells, in a suitable medium to produce said expanded population and, optionally, activated NK cells for each UCB unit, preferably during 3 to 28 days;
v) pooling the nUCB units cells obtained in the preceding step UCB units, or fraction thereof containing NK cells, to produce a population of pooled expanded and, optionally, activated NK cells; and
vi) optionally, depleting the T cells contained in the pooled NK cells obtained after step v).

In a preferred embodiment, the step vi) of depleting the T cells contained in the pooled NK cells obtained after step v) is not an optionally step and is part of the claimed method.

In another preferred embodiment, the step vi) of depleting the T cells contained in the pooled NK cells obtained after step v) is followed by a step of selecting the NK cells exhibiting the CD56+ biomarker, whether it is still desirable to eliminate remaining non-activated NK cells at this end of the process.

In another preferred aspect, the method for producing a population of expanded and, optionally, activated NK cells from n UCB units, comprises the step of:
i) providing at least n UCB units, or fraction thereof containing NK cells, with n≥2, preferably 2≤n≤100 or 3≤n≤50, more preferably 3≤n≤25, and wherein said at least n UCB units present the same pattern for major HLA class I groups genotype, preferably wherein each HLA group present in the pooled n UCB is recognized by the same major inhibitory KIR by NK cells;
ii) optionally red cell-/erythrocytes-depleting each UCB unit, preferably by density gradient separation, more preferably by Ficoll-Paque® density gradient separation, by the Hetastarch (Hydroxyethyl Starch; HES) method, by using the PrepaCyte® CB device or by a step of freezing and thawing;
iii) optionally, the population of cells obtained in step i) or ii) is frozen, kept in liquid nitrogen and thawed before step iv);
iv) optionally, or preferably, depleting the T cells contained in each UCB unit;
v) pooling the nUCB units cells obtained in the preceding step UCB units, or fraction thereof containing NK cells, to produce a population of pooled NK cells; and
vi) expanding and, optionally, activating the pooled NK cells obtained in the preceding step by contacting the NK cells contained in the pool, or fraction thereof containing NK cells, in a suitable medium to produce said population of pooled expanded and, optionally, activated NK cells, preferably during 1 to 5 weeks, preferably the amplification factor for NK cells after the expanding step(s) is at least 100, preferably, 200, 300 or 500 for an expanding/activation step(s) total duration comprised between 9 and 28 days.

In another preferred aspect, the method for producing a population of expanded, and, optionally, activated NK cells from n UCB units, comprises the step of:
i) providing at least n UCB units, or fraction thereof containing NK cells, with n≥2, preferably 2≤n≤100 or 3≤n≤50, more preferably 3≤n≤25, and wherein said at least n UCB units present the same pattern for major HLA class I groups genotype, preferably wherein each HLA group present in the pooled n UCB is recognized by the same major inhibitory KIR by NK cells;
ii) optionally red cell-/erythrocytes-depleting each UCB unit, preferably by density gradient separation, more preferably by Ficoll-Paque® density gradient separation, by the Hetastarch (Hydroxyethyl Starch; HES) method, by using the PrepaCyte® CB device or by a step of freezing and thawing;
iii) optionally, the population of cells obtained in step i) or ii) is frozen, kept in liquid nitrogen and thawed before step iv);
iv) pooling the nUCB units cells obtained in the preceding step UCB units, or fraction thereof containing NK cells, to produce a population of pooled NK cells;
v) optionally, or preferably depleting the T cells contained in the pooled NK cells obtained after step iv; and
vi) expanding and, optionally, activating the pooled NK cells obtained in the preceding step by contacting the NK cells contained in the pool, or fraction thereof containing NK cells, in a suitable medium to produce said population of pooled expanded and, optionally, activated NK cells, preferably during 1 to 5 weeks, preferably the amplification factor for NK cells after the expanding step(s) is at least 100, preferably, 200, 300 or 500 for an expanding/activation step(s) total duration comprised between 9 and 28 days.

All the methods relative to the production of activated/expanded NK cells are particularly suitable for preparing activated NK cells, from pooled UCB units, with miss expression of one of the following KIRs: KIR2DL2 and KIR2DL3, KIR2DL1, KIR3DL1 and KIR3DL2. Consequently, in this case, the activated/expanded pooled NK cells as above prepared will be alloreactive toward cells from others which lack the corresponding KIR ligand and, conversely, will be tolerant of cells from another individual who has the same KIR ligands.

Thus, by these methods, it can be produced a collection, or a therapeutic cells bank, of at least 2 different production lots, preferably 3, more preferably 4, of pooled activated/expanded NK-cells obtainable by a method for producing NK cells of the invention, or a collection of at least 2, 3 or 4 fractions of said production lots, and wherein each production lot exhibits a different miss expression of one of the major inhibitory KIRs, preferably selected from the group of KIR2DL2 and KIR2DL3, KIR2DL1, KIR3DL1 and KIR3DL2 inhibitory KIRs.

Such a collection of at least 2 different production lots, preferably 3, more preferably 4, of pooled activated/expanded NK-cells obtainable by a method for producing pooled activated/expanded NK-cells NK cells contained in the composition of the invention is comprised in the present invention.

In a preferred embodiment said collection, is a collection of storage containers comprises at least 2, 3 or 4 containers that each contains a pooled activated/expanded NK-cells, or fraction thereof, obtainable by a method for producing NK cells of the invention and exhibiting a particular miss expression of one of the major inhibitory KIRs.

According to the present invention, one production lot, or fraction thereof which is needed in quantity for treating one patient, of the claimed collection can be used for transplantation in a patient in need thereof, preferably a patient exhibiting target cells that do not express the specific major KIR ligand which is recognized by the pooled activated/amplified NK cells production lot which will be transplanted.

HLA/KIRs genotyping/phenotyping of UCB/NK cells or patient target cells may be performed by any well-known standards methods.

In a preferred embodiment, said suitable medium suitable to expand and to activate the NK cells comprised accessory cells and/or at least one suitable NK activated factor.

In a preferred embodiment, said accessory cells are selected from the group of:
  mammals cells, preferably human cell, more preferably from HLA-typed collection of cells and, optionally, irradiated cells, particularly gamma-, X- or UV-irradiated cells, gamma-irradiated cells being preferred;
  transformed mammals cells, preferably human cells, wherein in said cell, the expression of one gene encoding for a Killer-Cell Immunoglobulin-like Receptor(s) (KIR) ligand has been inhibited.

In a preferred embodiment, said cells from HLA-typed collection of cells are from the PLH cell line, preferably selected from the group of ECACC No. 88052047, IHW number 9047 and HOM-2, ID no HC107505, IHW number 9005.

In a preferred embodiment, said accessory cell is a transformed mammal cell wherein the expression of one gene encoding for a KIR ligand has been inhibited and which further comprises the inhibition or the reduction of the MHC-I expression and/or the inhibition of the expression of the ERK5 gene. The method for preparing such accessory cells is well known by the skilled person (see WO 2012/146702 published on Nov. 1, 2012 which is incorporated herein by reference).

The inhibition or reduction of the MHC-I expression is said accessory cell may be performed by any method well known in the art. For example said methods are exemplified in the international patent application publication WO2009141729A2. Typically, said inhibition or reduction of MHC-I expression is performed by using inhibitor of beta-2-microglobulin gene expression.

As indicated above, said accessory cell will be presenting a negative ERK5 phenotype. The term "cell presenting a negative ERK5 phenotype" means a cell having a reduction of at least 10%, preferably 25% to 90%, for example 25% to 50% or 50% to 75% in the level of expression or the quantity of ERK5 protein present in the cell, in particular in the mitochondrial fraction, compared with its level of expression.

The inhibition or reduction of the ERK5 gene expression is said cell may be performed by any method well known in the art. For example said methods are exemplified in the international patent application publication WO2009141729A2. Typically, said inhibition or reduction of gene ER 5 expression is performed by using inhibitor of ER 5 gene expression.

In a preferred embodiment, said accessory cells have been immortalized, preferably by Epstein Barr Virus (EBV) transformation.

As a result said accessory cell will constitute a cell line that proliferate indefinitely in culture. Methods for immortalizing cells are well known in the art, particularly using the "Epstein Barr virus" ("EBV") process for immortalize human lymphocyte.

In a preferred embodiment, said suitable medium comprised as suitable NK activated factor interleukin-2 (IL-2), IL-7 and/or IL-12 and/or IL-15, or with alpha- or beta-interferon, preferably human recombinant activated factor.

When accessory cells are not used for activating the NK cells, the activation can be carried out using the following possible medium containing NK cells activating factor:
  1/ IL-2 5 ng/ml+/−anti-CD3 50 ng/ml+IL-7 10 ng/ml+IL-12 10 ng/ml, preferably after 7 days;
  2/ hIL-15 30 ng/ml+hIL-21 30 ng/ml (PeproTech)+hydrocortisone $10^{-6}$ M>CD34+ 21 days of cultivation thus 21 days of cultivation for the maturation/activation of the NK Cells;
  3/ IL-2 500 U/ml+beads CD335 (NKp46) and CD2;
  4/ Mix of cytokines IL-7, SCF, IL-2, IL-15 (strong concentration) and GM-CSF, G-CSF, IL-6 (low concentration) for NK cells expansion from D14 to D42, in bioreactor, from CD34+ amplification; D0-9=low molecular heparin+mix of cytokines (strong concentration) SCF, Flt3L, TPO, IL-7 and (low concentration) GM-CSF, G-CSF, IL-6 (CD34+ amplification); J9-14=low molecular heparin+mix of cytokines (strong concentration) SCF, Flt3L, IL-15, IL-7 and GM-CSF, G-CSF, IL-6 (low concentration, NK differentiation).
  (IL-18 and IFN alpha can be also used).

Activation and Expanding in Presence of Accessory Cells:
  1/ IL-2 500 U/ml+autologous/allogenic irradiated feeder PBMC (25 Gy) ou EBV-LCL (100 Gy), ratio feeder cells:NK 20:1 (or 10:1 for UCB unit scale-up) at D0
  2/ IL-2 200 U/ml+mitomycin treated feeder (PBMC+K562 ratios 1:1) ratio feeder cells:NK 8:1

3/ IL-2 500 U/ml+allogenic irradiated feeder PBMC (5 000 rad) at D0 and D7 ratio feeder cells:total 10:1+ OKT3 (anti-CD3) 30 ng/ml in the culture medium or pre-incubated with feeder cells 4/ IL-2 500 U/ml+irradiated feeder Jurkat-KL1 (300 Gy) at D0

5/ IL-2 500 U/ml+autologous irradiated feeder PBMC (2000 rad, +OKT3 10 ng/ml at the beginning for stimulate the T lymphocytes of the feeders cells (depleted din the non-irradiated faction)) ratio feeder cells: NK 5:1 J0

6/ IL-2+IL-15+feeder irradiated feeder K562-mb15-41BBL (100 Gy)

In another preferred embodiment, in this method for the obtention of the pooled UCBs NK cells population, the step of depleting the T cells is carried out by a method comprising the step of:

contacting the cells with a depleting antibody; and
removing the cells detected by said depleting antibody.

The depleting antibody is preferably at least an antibody selected from the group consisting of an anti-CD3, an anti-CD14, and an anti-CD 20 antibody, preferably an anti-CD3 antibody.

In the population of depleted cells obtained, less than 0.5% or even less than 0.1% or even less than 0.001% are CD3 positive cells.

In another preferred embodiment, in this method, each UCB unit or the pooled n UCB units are red cell-/erythrocytes depleted, preferably by density gradient separation, more preferably by Ficoll-Paque® density gradient separation, by the Hetastarch (Hydroxyethyl Starch; HES) method, by using the PrepaCyte® CB device or by a step of freezing and thawing;

In another preferred embodiment, in this method, each UCB unit or the pooled n UCB units are red cell-depleted by a method comprising the lysis of the red blood cells, particularly by a method including a step of freezing and thawing the cells contained in each of the UCB unit or in the n UCB units pooled cells.

In another preferred embodiment, the UCB units used in step b) or in step i) are thawed UCB units from frozen stored UCB units.

Said pooled UCB units, or fraction thereof containing cells, obtained at the end of the method is preferably stored at a temperature below −70° C., preferably below −80° C., more preferably in liquid nitrogen.

In another preferred embodiment of this method,
each UCB unit is preliminary diluted in a suitable culture medium, preferably in a RPMI medium before use; and/or
after the red-cell/erythrocytes depletion of each UCB unit or of the pooled n UCB units, the collected cells are resuspended in a suitable culture medium, preferably in a RMPI medium, or in medium type X-VIVO™ (Lonza), AIM-V™ medium (Invitrogen) or CellGro™ (CellGenix), this medium optionally containing fetal bovine serum AB negative (FBS); and/or
if the collected cells from each red-cell depleted UCB unit or from the pooled red-cell depleted UCB units are stored frozen, the collected cells are resuspended in a suitable culture comprising a white cells cryoprotectant.

More preferably, the ratio between the NK cells and the accessory cells present in the suitable medium for NK cells expansion/activation is comprised between 0.01 and 2, preferably between 0.05 and 1.0, more preferably between 0.1 and 0.5.

More preferably, the accessory cells present in the suitable medium for NK cells expansion/activation and the NK cells to be expanded/activated are HLA-KIR mismatched.

According to another preferred embodiment, the invention relates to a method for the production of a pooled, and activated and/or expanded NK cells according to the present invention, wherein said method further comprising a step of CD56+NK cells enrichment.

According to another preferred embodiment, it is described a method for the production of at least two distinct pools a population of expanded, optionally, activated NK cells from UCB units, wherein the major HLA class I group recognized by NK cells for each pooled n UCB is different, and wherein each pool of a population of expanded, optionally, activated NK cells from n UCB units is produced by a method for producing a pooled activated and/or expanded NK cells according to the present invention.

More particularly, it is disclosed a method for the production of at least 2, 3, preferably 4 distinct pools a population of expanded, optionally, activated NK cells from UCB units according to the present invention, wherein the major HLA class I group recognized by NK cells for each pooled n UCB is different and selected from the group consisting of HLA A3/A11 which is recognized by KIR3DL2, HLA Bw4, which recognized by KIR3DL1, HLA C group 1 which is recognized by KIR2DL2/3 and HLA C group 2 which is recognized by KIR2DL2.

According to another embodiment, it is also disclosed a population of cells:
obtained by the method according to the present invention, or
obtainable by the method according to the present invention and wherein said "obtainable" population of cells contains cells, preferably NK cells originated from at least n UCB units, or fraction thereof containing NK cells, with n≥2, preferably 2≤n≤100 or 3≤n≤50, more preferably 3≤n K 25, and, preferably, wherein said n UCB units further present the same pattern for major HLA class I groups genotype, preferably wherein the major HLA class I group recognized by NK cells for each pooled n UCB is different and selected from the group consisting of HLA A3/A11 which is recognized by KIR3DL2, HLA Bw4, which recognized by KIR3DL1, HLA C group 1 which is recognized by KIR2DL2/3 and HLA C group 2 which is recognized by KIR2DL2.

More preferably, said population of cells obtainable by the above method further exhibiting for each pooled n UCB a miss expression of one of the KIRs selected from the group of KIR2DL2 and KIR2DL3, KIR2DL1, KIR3DL1 and KIR3DL2.

The invention also relates to a pharmaceutical composition according to the present invention further comprising a pharmaceutically acceptable carrier.

In the present description, "pharmaceutically acceptable carrier" refers to a compound or a combination of compounds made part of a pharmaceutical composition that do not cause secondary reactions and that, for example, facilitate the administration of the active compounds, increase their lifespan and/or effectiveness in the body, increase their solubility in solution or improve their preservation. Said pharmaceutically acceptable carriers are well known and will be adapted by those persons skilled in the art according to the nature and the mode of administration of the active compounds selected.

According to another aspect, the invention is directed to a product or a composition comprising a collection of storage containers for mammalian cells, preferably for human cells, wherein each of said storage containers contains a fraction of a production lot of a population of cells, preferably pooled UCBs NK cells obtainable or obtained by the above described method and a therapeutic antibody which can be bound by CD16.

Preferably, said collection of storage containers for mammalian cells according to the present invention contains expanded and/or activated NK cells.

Preferably, said collection of storage containers for mammalian cells according to the present invention or said composition according to the present invention, contains at least $10^7$, preferably 2 to 10. $10^7$ or 10 to 100. $10^7$ activated and/or expanded NK cells, depending of the weight of patient to be treated.

Preferably, each of said storage containers collection according to the present invention, or said composition according to the present invention, contains NK cells and being essentially free of CD3+ T cells, preferably less than 0.1% or less than 0.01%.

Preferably, said collection of storage containers for mammalian cells according to the present invention or said composition according to the present invention, contains:
- at least 75%, preferably over 85 or 90% of NK cells exhibiting the marker the marker CD56+; and/or
- at least 75%, preferably over 80% of NK cells exhibiting CD45RAdim.

According to another aspect, the invention is directed to a storage container of a collection of storage containers according to the present invention, or said composition according to the present invention, for its use for suppressing the proliferation of tumor cells, preferably for the prevention and/or the treatment of cancer or for the treatment of infection.

In another aspect, the present invention is directed to a pharmaceutical kit comprising:
a first composition comprising a population of alloreactive natural killer cells (NK cells), wherein said cells population is obtained by a method comprising the steps of:
(a) providing at least n umbilical cord blood units (UCB units), or fraction thereof containing said NK cells, with n≥2; and
(b) pooling said at least n UCB units, or fraction thereof containing said NK cells, to produce said population of NK cells.

In a preferred embodiment said first composition comprises a population of alloreactive natural killer cells (NK cells), obtained from a mixture of at least n umbilical cord blood units (UCB units), or fraction thereof containing said NK cells, with 3≤n≤50

In a preferred embodiment said first and second composition are administered simultaneously, separately or sequentially.

In a preferred embodiment said second composition comprises a monoclonal antibody directed against a cell receptor which is overexpressed by tumoral cells.

In a preferred embodiment said first said second composition comprises a monoclonal antibody directed against a cell receptor and wherein said monoclonal antibody is a low or non-fucosylated antibody.

In a preferred embodiment said first said second composition comprises a monoclonal antibody which is derived from a milk of a transgenic mammal or from the YB2/0 cell line (ATCC, CRL-1662) or subclone thereof.

In a preferred embodiment said first said second composition comprises a monoclonal antibody selected the group consisting of anti-CD20, anti-HER2/Neu and anti-EGFR antibodies.

In a preferred embodiment said first said second composition comprises a monoclonal antibody selected the group consisting of TG20, Ublituximab, Trastuzumab and Herceptin-like antibodies.

In a preferred embodiment said first said second composition comprises antibody is a human, humanized or chimeric antibody or a fragment thereof.

In a preferred embodiment said first said second composition comprises is selected from the group of:
Anti-CD20 antibody
 Rituximab, Ublituximab, Obinutuzumab, Ocaratuzumab, Ocrelizumab, Odulimomab, Ofatumumab, Tositumomab; Veltuzumab, FBTA05 or Ibritumomab tiuxetan;
Anti-HER2/Neu antibody
 Trastuzumab, Ertumaxomab or Pertuzumab;
Anti-EGFR antibody
 Cetuximab, Futuximab, Imgatuzumab, Matuzumab, Necitumumab or Nimotuzumab;
Anti-GD2 antibody
 Dinutuximab; and
Anti-CD52 antibody
 Alemtuzumab.

In a preferred embodiment said first composition comprises cells population of NK cells obtained by a method further comprising the step of:
(c) depleting the T cells contained in the pool obtained in step (b); or
(d) depleting the T cells contained in each of the n UCB units before the step (b) of pooling.

In a preferred embodiment, in the first composition, said population of NK cells is obtained by a method comprising further a method of expanding said population of NK cells from cells contained in said n UCB units, and wherein,
optionally each UCB units has been preliminary and separately expanded for said NK cells before the step of pooling said at least n UCB units; and/or
expanding the desired cells obtained from the population of cells obtained after the step of pooling said at least n UCB units in a suitable medium to produce said expanded population of desired cells.

In a preferred embodiment in the first composition, said population of NK cells is an activated population of NK cells, obtained by a method further comprising a step of activating said population of NK cells.

In a preferred embodiment in the first composition, said population of NK cells is an activated population of NK cells wherein:
optionally each UCB units has been preliminary and separately expanded and activated for said NK cells before the step of pooling said at least n UCB units; and/or
activating the desired cells obtained from the population of cells obtained after the step of pooling said at least n UCB units in a suitable medium to produce said activated population of desired cells.

In a preferred embodiment in the first composition, said population of NK cells is obtained by a method wherein said suitable medium suitable to expand and to activate the NK cells comprised accessory cells and/or at least one suitable NK activated factor.

In another aspect, the present invention is directed to a method for treating cancer comprising the administration to a subject in need of treatment for cancer of a therapeutically effective amount of a first composition and a second composition, wherein said first composition comprising a population of alloreactive natural killer cells (NK cells) which are derived from a mixture of at least n umbilical cord blood units (UCB units), or a mixture of fraction thereof containing said NK cells, with n≥2; and said second composition comprising a monoclonal antibody or a specific binding fragment thereof directed to a cell receptor antigen of cells of said subject.

In a preferred embodiment, the method for treating cancer according to present invention comprises the administration to a subject in need of treatment for cancer of a therapeutically effective amount of a first composition and a second composition, wherein said first composition comprising a population of alloreactive natural killer cells (NK cells) derived from a mixture of at least n umbilical cord blood units (UCB units), with 3≤n≤50.

In a preferred embodiment, in the method for treating cancer according to present invention, said first and second composition are administered simultaneously, separately or sequentially.

In a preferred embodiment, in the method for treating cancer according to present invention, said cancer is selected from cancers overexpressing a cell receptor at the surface of the tumoral cells of the subject in need of the treatment, and wherein the monoclonal antibody of said second composition is directed against said receptor.

In a preferred embodiment, in the method for treating cancer according to present invention, said second composition comprises a monoclonal antibody which is a low or non-fucosylated antibody.

In a preferred embodiment, in the method for treating cancer according to present invention, said second composition comprises a monoclonal antibody which is derived from a milk of a transgenic mammal or from the YB2/0 cell line (ATCC, CRL-1662) or subclone thereof.

In a preferred embodiment, in the method for treating cancer according to present invention, said second composition comprises a monoclonal antibody selected the group consisting of anti-CD20, anti-HER2/Neu and anti-EGFR antibodies.

In a preferred embodiment, in the method for treating cancer according to present invention, said second composition comprises a monoclonal antibody selected the group consisting of TG20, Ublituximab, Trastuzumab and Herceptin-like antibodies.

In a preferred embodiment, in the method for treating cancer according to present invention, said cancer to be treated are selected from the group of hematologic malignancy tumor cells, solid tumor cells or carcinoma cells, preferably leukemia cells, acute T cell leukemia cells, chronic myeloid lymphoma (CML) cells, acute myelogenous leukemia cells, chronic myelogenous leukemia (CML) cells, multiple myeloma cells, or lung, colon, prostate, glyoblastoma cancer.

By solid tumor, it is intended to designate a malignancy that forms a discrete tumor mass in contrast to lymphoproliferative malignancies such as leukemia, which may diffusely infiltrate a tissue without forming a mass.

Preferably said solid tumor or solid cancer is selected from the group of brain, breast, ovarian, prostate, colorectum, kidney, sarcoma and melanoma solid tumor.

In a more preferred embodiment, in the method for treating cancer according to present invention, said cancer to be treated are selected from the group of HER2-positive cancer and said second composition of the pharmaceutical kit of the present invention comprises an anti-HER2 monoclonal antibody or a specific binding fragment thereof.

More preferably said HER2-positive cancer is a breast or an ovarian cancer.

More preferably said HER2-positive cancer is a breast or an ovarian cancer and said second composition of the pharmaceutical kit of the present invention. comprises an anti-HER2 monoclonal selected from the group of Trastuzumab or derived or biosimilar antibody thereof, particularly low or non-fucosylated Trastuzumab, Herceptine-like, trastuzumab obtained from milk of transgenic mammal, preferably from milk of transgenic goat capable of secreting chimeric or humanized Trastuzumab.

In a preferred embodiment, the present invention is directed to a method for treating disease which are characterized by having too many B cells, overactive B cells, or dysfunctional B cells comprising the administration to a subject in need of treatment for said disease of a therapeutically effective amount of a first composition and a second composition, wherein said first composition comprising a population of alloreactive natural killer cells (NK cells) which are derived from a mixture (also named a pool) of at least n umbilical cord blood units (UCB units), or a mixture of fraction thereof containing said NK cells, with n≥2, and said second composition comprising an anti-CD20 monoclonal antibody or a specific binding fragment thereof.

In a preferred embodiment, in the method for treating disease which are characterized by having too many B cells, overactive B cells, or dysfunctional B cells according to present invention, said first and second composition are administered simultaneously, separately or sequentially.

In a preferred embodiment, in the method for treating disease which are characterized by having too many B cells, overactive B cells, or dysfunctional B cells according to present invention, said first composition is obtained by a process as preferably disclosed above and in the Examples of the present specification for obtaining expanded and/or activated NK cells from a mixture (also named a pool) of at least 2 UCB.

Preferably said disease to be treated is selected from the group of cancer pathologies, more preferably hematologic malignancy tumor cells, leukemia cells, acute T cell leukemia cells, chronic myeloid lymphoma (CML) cells, acute myelogenous leukemia cells, chronic myelogenous leukemia (CML) cells, multiple myeloma cells.

Preferably said disease to be treated which are characterized by having too many B cells, overactive B cells, or dysfunctional B cells is selected from the group of autoimmune diseases or infectious diseases, dysimmune/autoimmune diseases, particularly selected for rheumatoid arthritis treatment, refractory rheumatoid disease (for example rheumatoid disease having an inadequate response to one or more anti-TNF-alpha therapy and/or methotrexate therapy), multiple sclerosis, systemic lupus erythematosus, chronic inflammatory demyelinating polyneuropathy and autoimmune anemias.

In a more preferred embodiment, in the method for treating disease which are characterized by having too many B cells, overactive B cells, or dysfunctional B cells cancer according to present invention, said second composition of the pharmaceutical kit of the present invention comprises an anti-CD20 monoclonal antibody or a specific binding fragment thereof selected from the group of rituximab, TG20 and Ublituximab or derived or biosimilar antibody thereof, particularly low or non-fucosylated anti-CD20 antibodies, optionally obtained from milk of transgenic mammal, preferably from milk of transgenic goat capable of secreting chimeric or humanized low or afucosylated or glycoengineered anti-CD20 antibodies.

According to the present invention, the pooled/mixture activated and/or expanded NK cells as prepared according to the invention or said composition according to the present invention, may also useful for the treatment of infectious diseases or dysimmune/autoimmune diseases.

In a preferred embodiment, the cells contained in the storage container or the composition according to the present invention, are administered to the subject by a systemic or local route, depending of the disease/pathology to be treated. Preferably, said compounds may be administered systemically by intramuscular, intradermal, intraperitoneal or subcutaneous route, or by oral route. The composition comprising the antibodies according to the invention may be administered in several doses, spread out over time.

Their optimal modes of administration, dosing schedules and galenic forms may be determined according to criteria generally considered in the establishment of a treatment adapted to a patient such as, for example, the age or the weight of the patient, the seriousness of the patient's general health, tolerance to the treatment and side effects noted.

The invention will be further illustrated by the following figures and examples. However, these examples and figures should not be interpreted in any way as limiting the scope of the present invention.

DESCRIPTION OF FIGURES

FIGS. 2 and 3 illustrate the NK proliferation obtained after or without CD3 depletion.

FIGS. 12A-12C: Percentage of patient cells lysis induced by the combination of NK cells+mAb for p45 B lymphoma patient cells (FIG. 12A) and for B-CLL p53 and p46 patient cells (FIGS. 12B and 12C).

FIGS. 13A-13D: Percentage of cell line cells lysis induced by the combination of NK cells+mAb for Daudi cell line (FIG. 13A), Raji cell line (FIG. 13B), Ri-1 cell line (FIG. 13C) and SUDHL4 cell line (FIG. 13D).

FIGS. 14A-14D: Study of anti-CD20 dose effect (E:T 1/1) on cell lines.

Percentage of cell line cells lysis induced by the Anti-CD20 mAb or the combination of NK cells+mAb for Daudi cell line (FIG. 14A), Raji cell line (FIG. 14B), Ri-1 cell line (FIG. 14C) and SUDHL4 cell line (FIG. 14D).

Figure 15A:
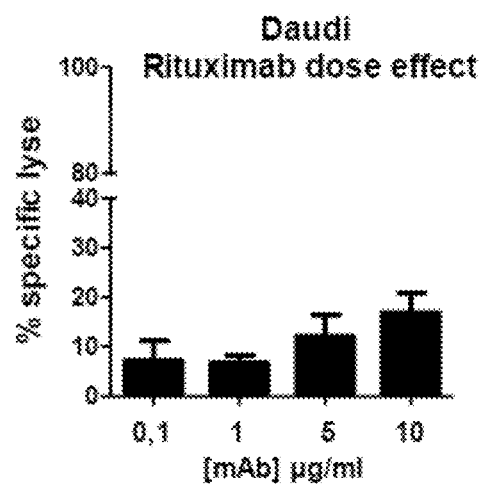
Figure 15B:
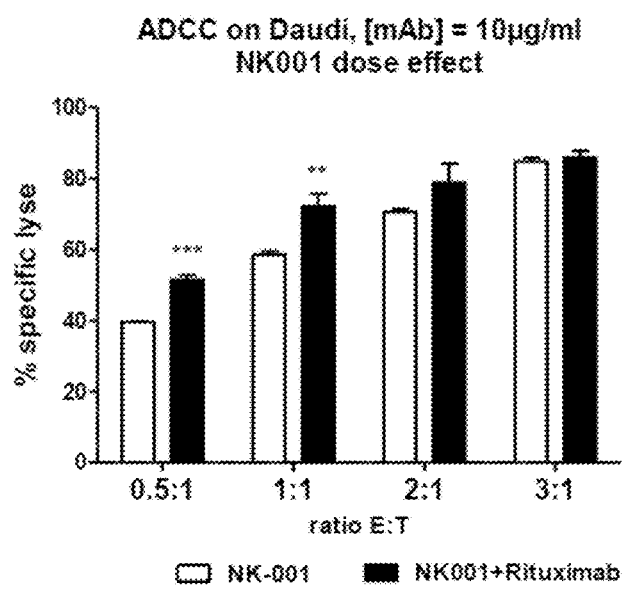
Figure 16:
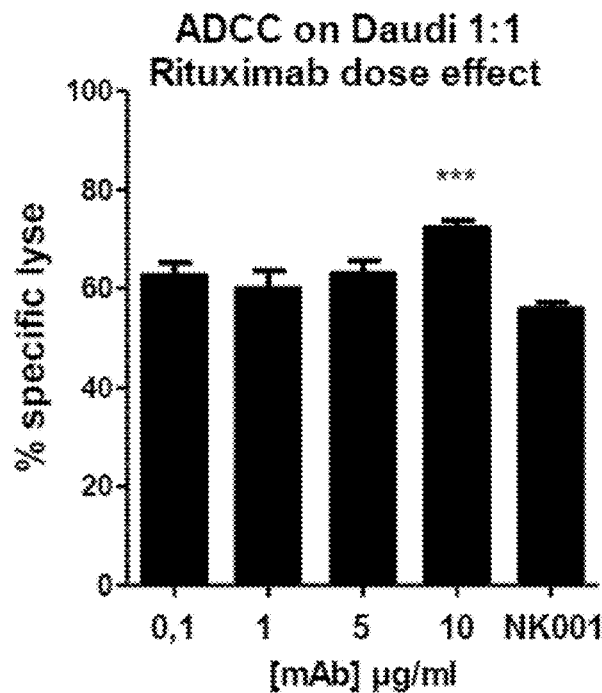
Figure 17:
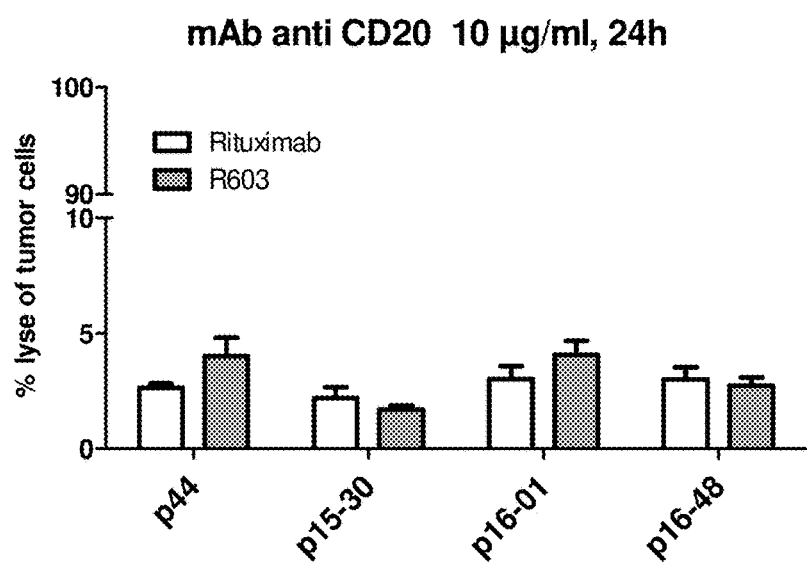
Figure 18:
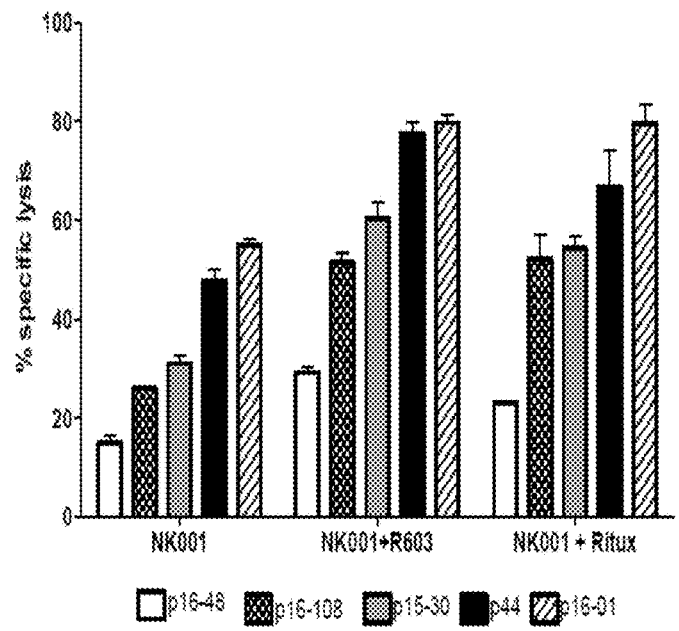
Figure 19A:
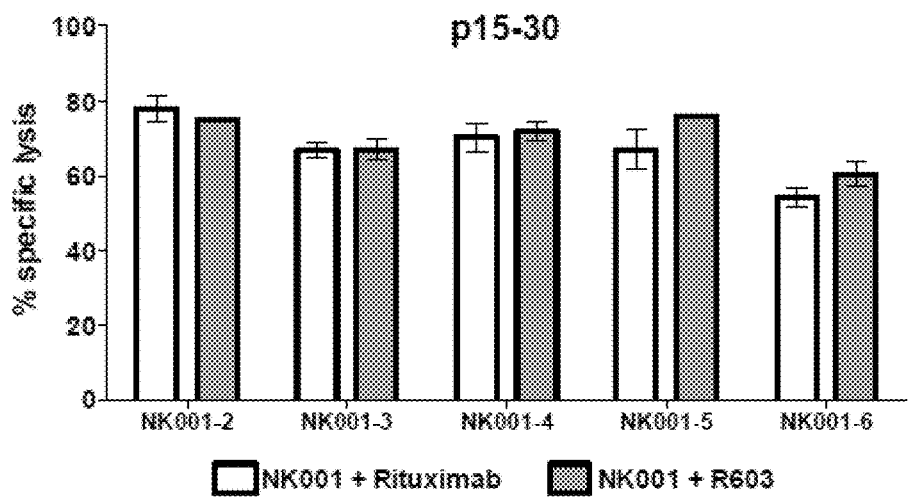
Figure 19B:
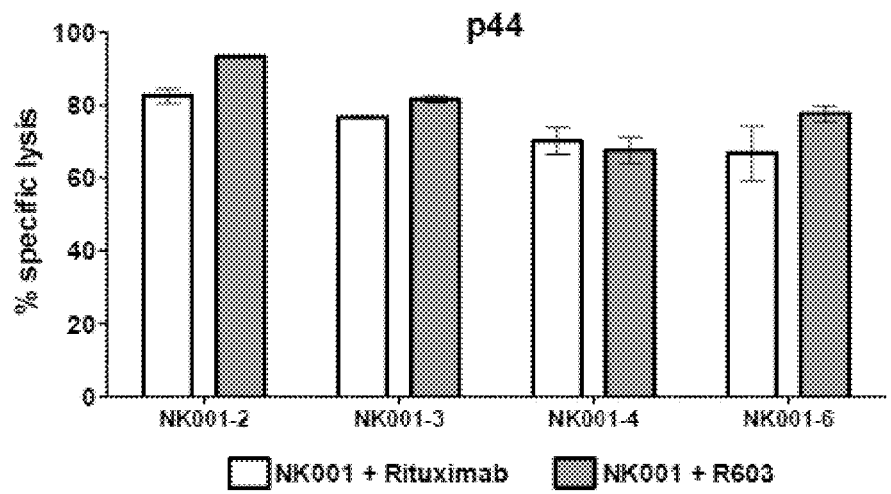
Figure 19C:
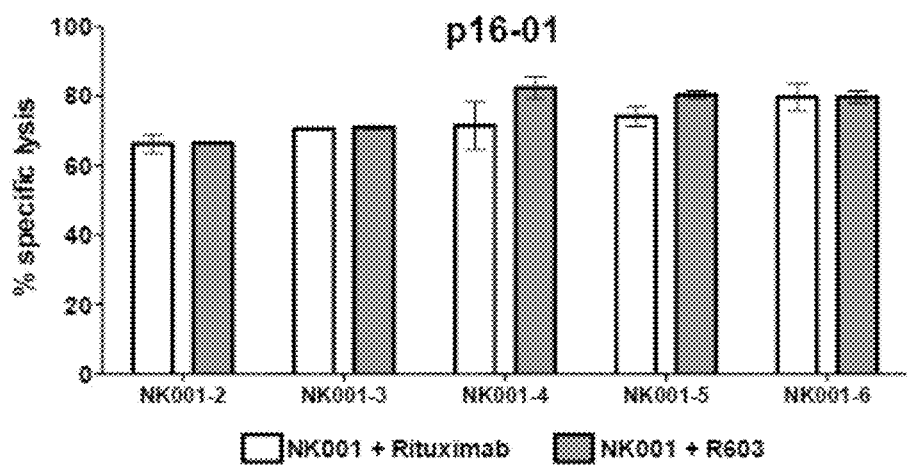
Figure 20:
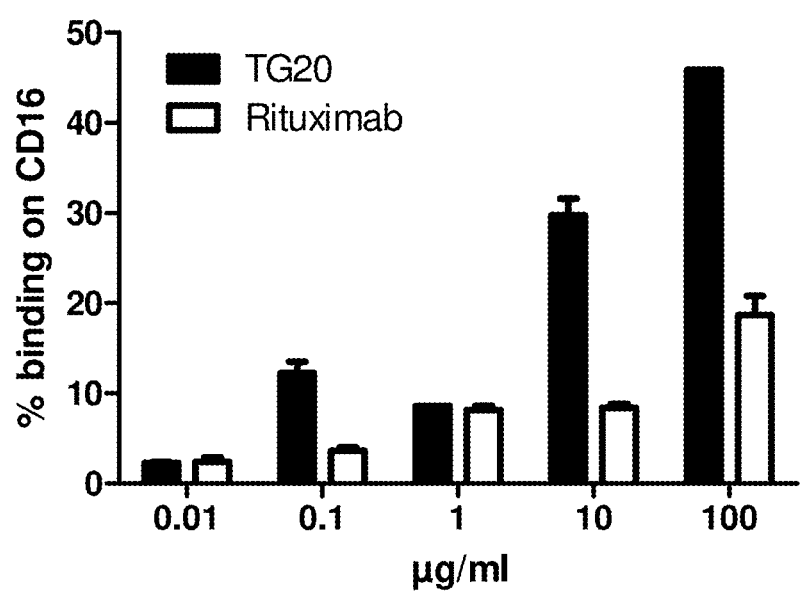

FIGS. 15A and 15B illustrates Rituximab cytotoxicity dose effect and ADCC with Rituximab+NK001 dose effect on Daudi cell line FIG. 16 illustrates the NK001 and NK001+Rituximab dose effect on Daudi ADCC FIG. 17 illustrates mAb anti CD20 cytotoxicity on clinical sample FIG. 18 illustrates ADCC induced by NK-001 in synergy with anti CD20 on clinical sample FIGS. 19A-19C illustrates the reproducibility of the results obtained for ADCC with 3 lots of NK001 on p15-30 (A), p44 (B) and P16-01 (C) clinical samples, between R603 and Rituximab FIG. 20 illustrates Anti-CD20 mAb binding on NK001

Figure 21B:
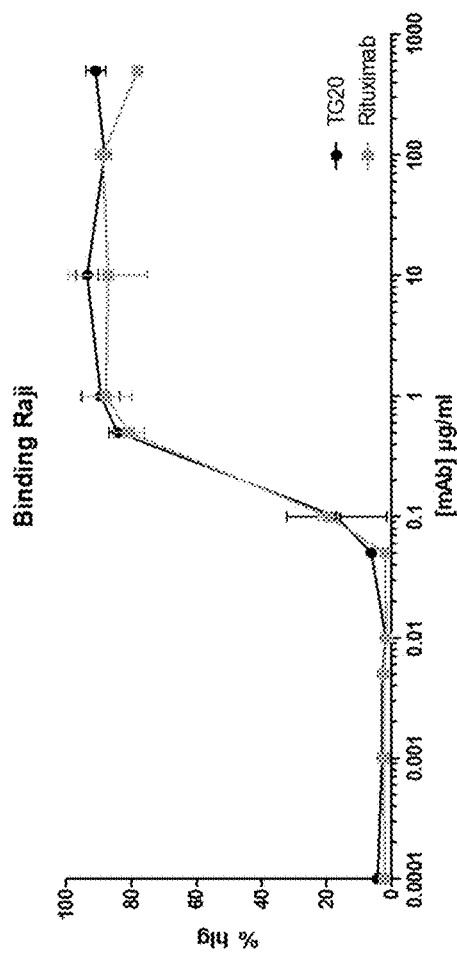
Figure 21A:
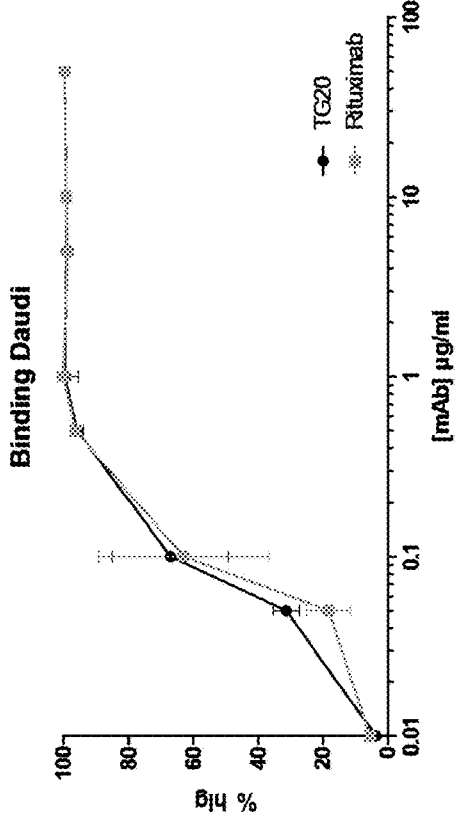
Figure 23A:
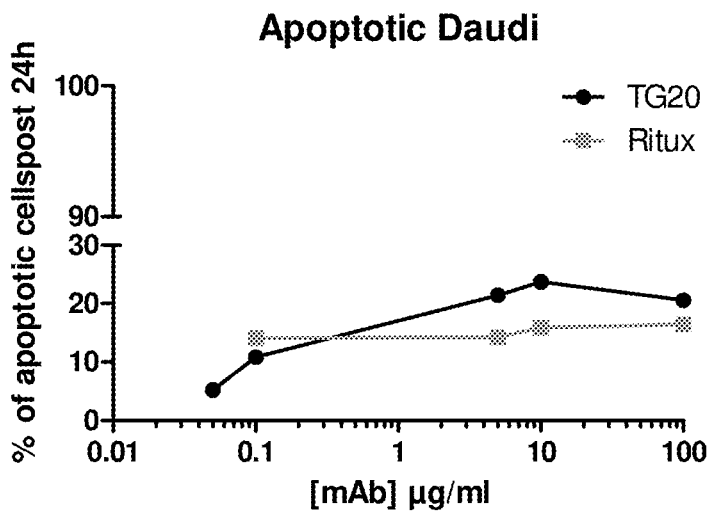
Figure 23B:
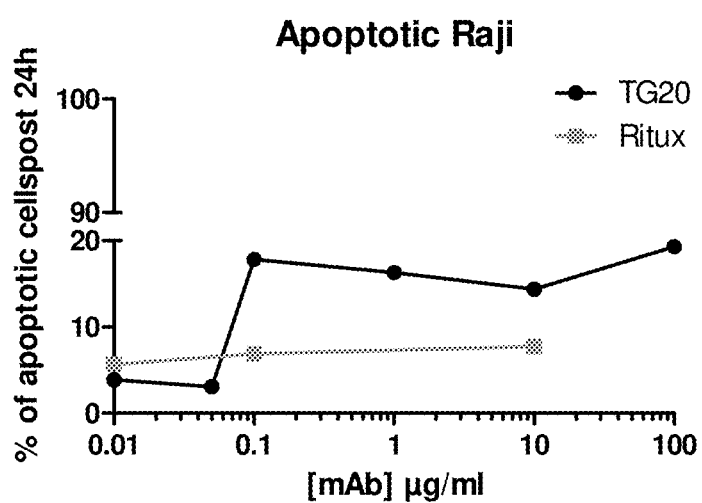
Figure 24A:
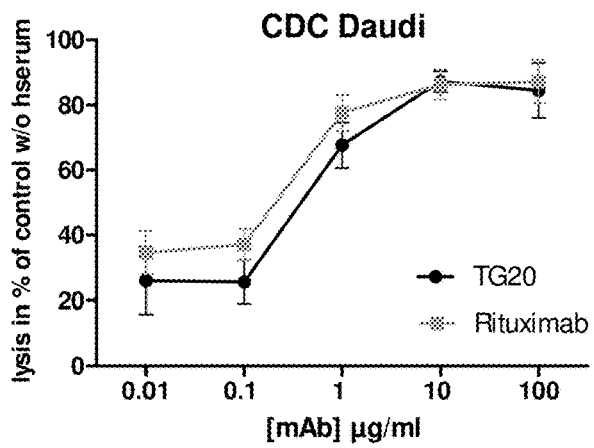
Figure 24B:
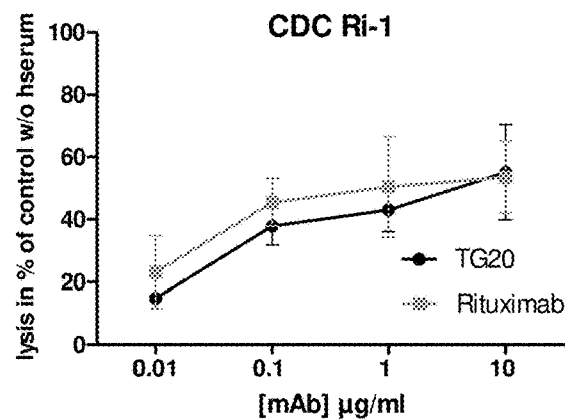
Figure 24C:
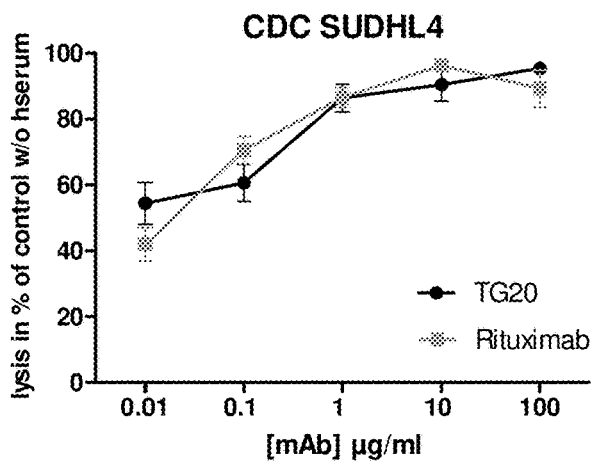
Figure 25:
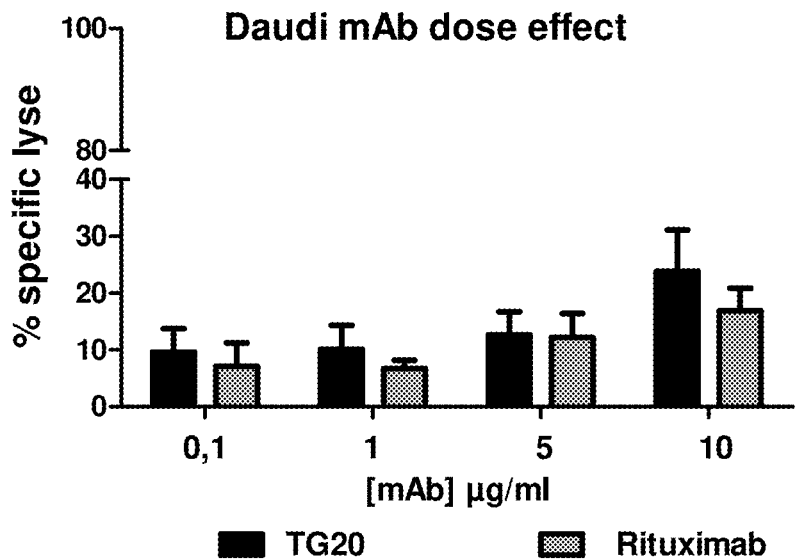
Figure 26:
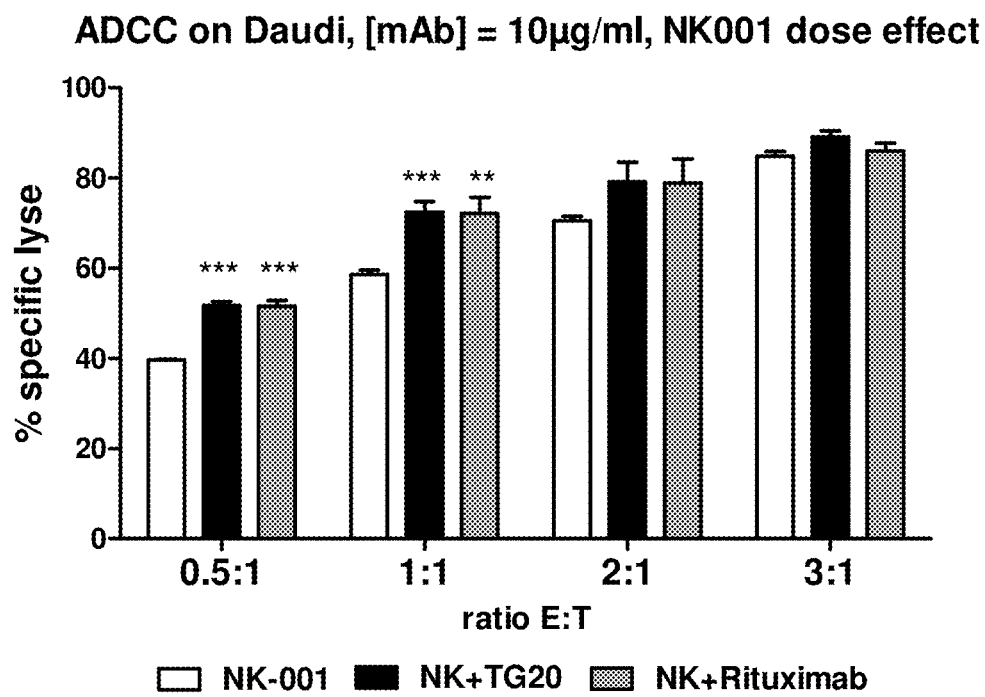
Figure 27:
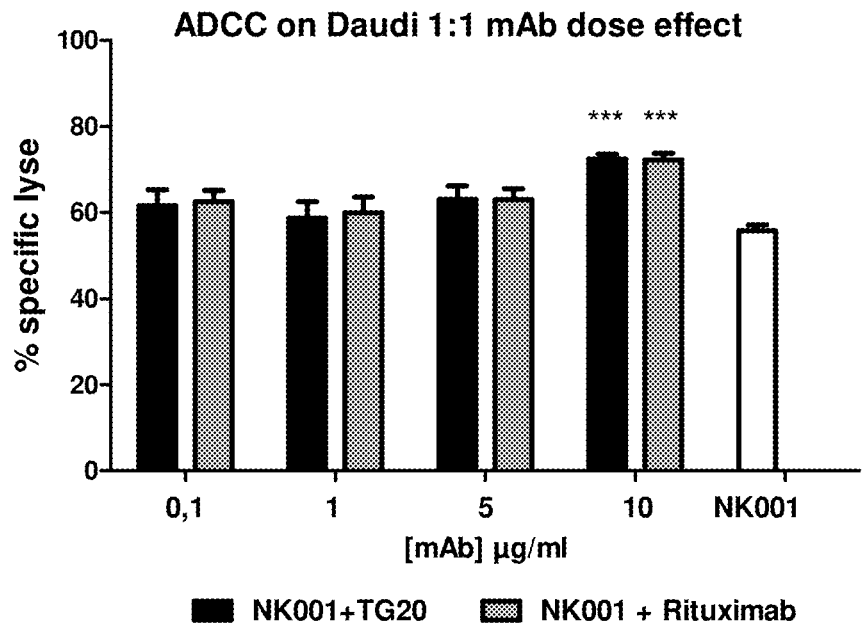
Figure 28:
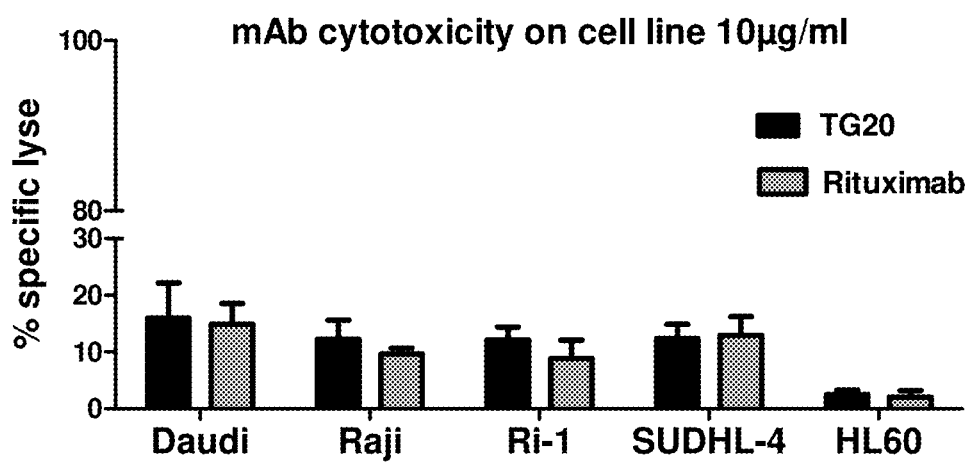
Figure 29:
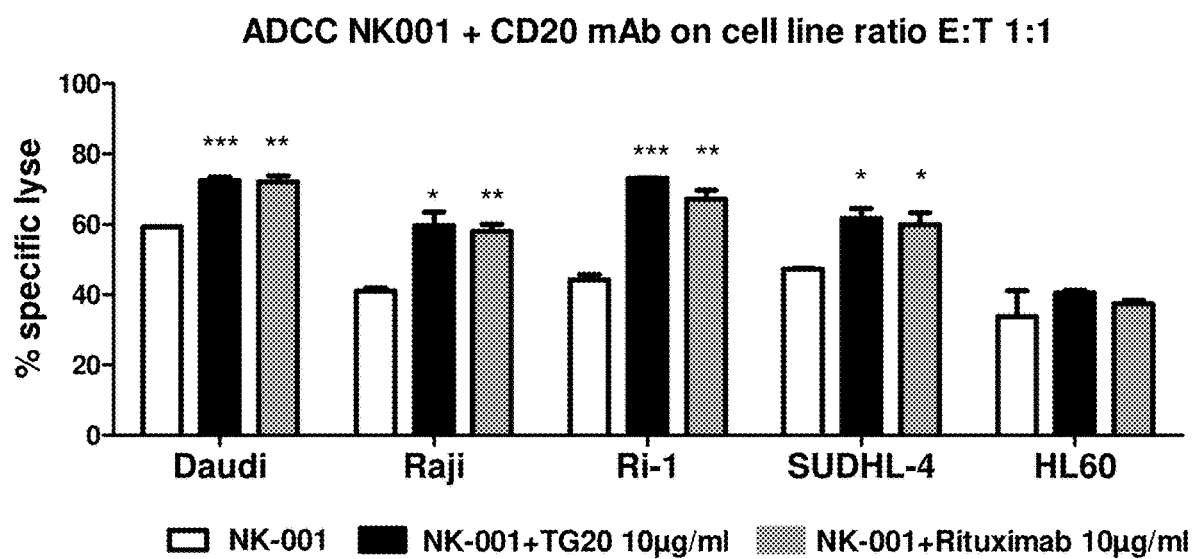
Figure 30:
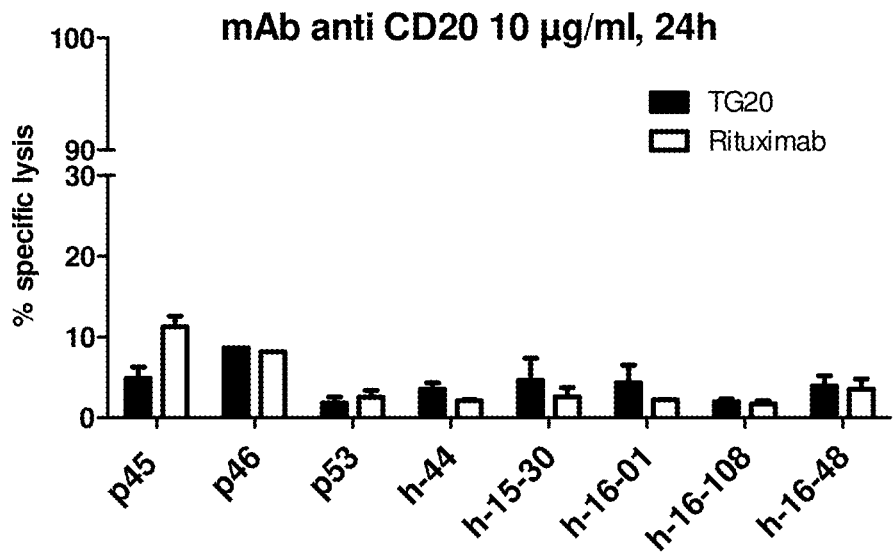
Figure 31:
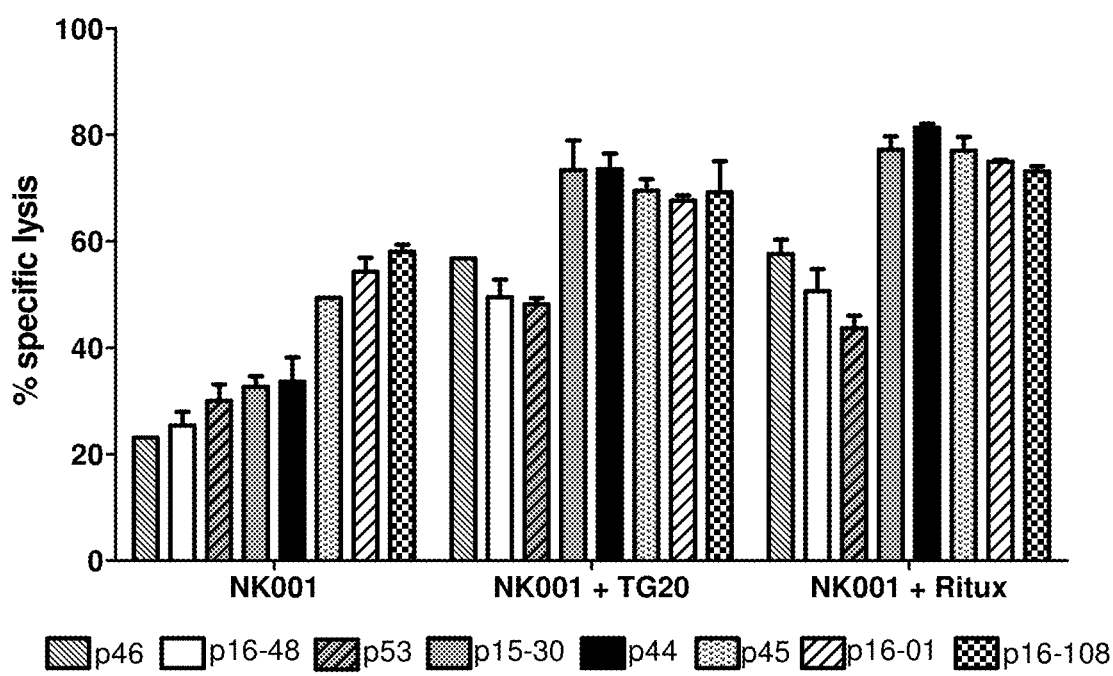
Figure 32A:
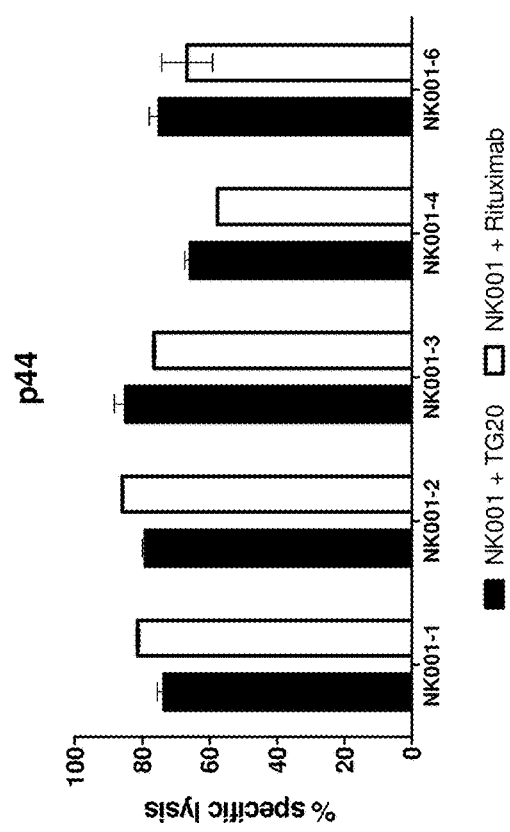
Figure 32B:
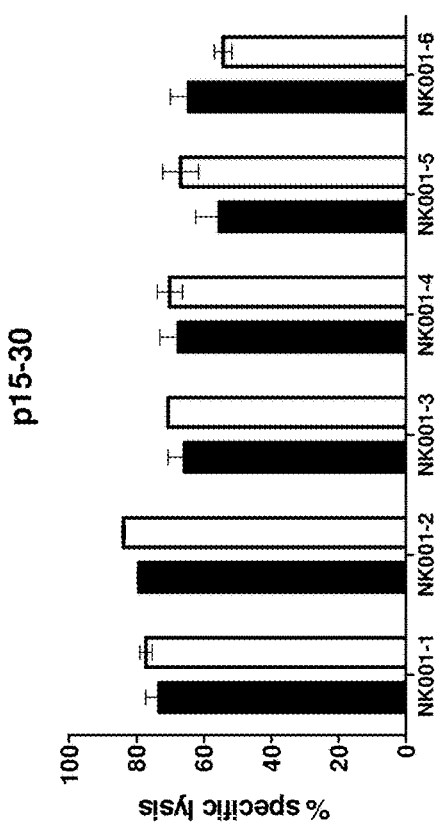
Figure 32C:
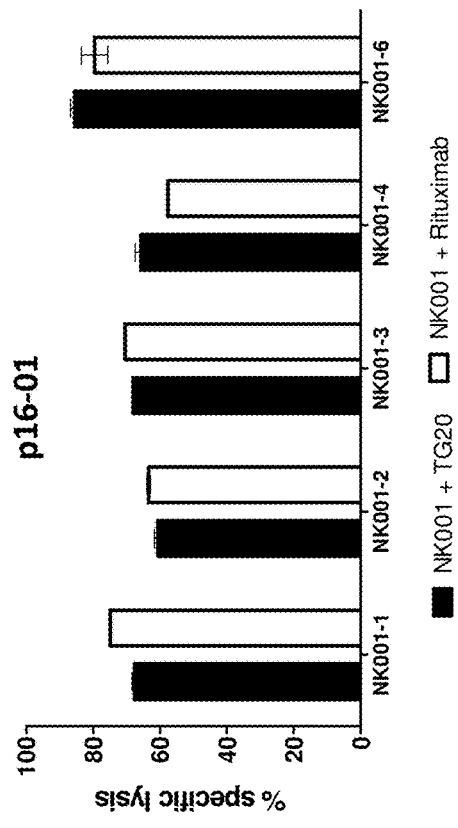
Figure 33:
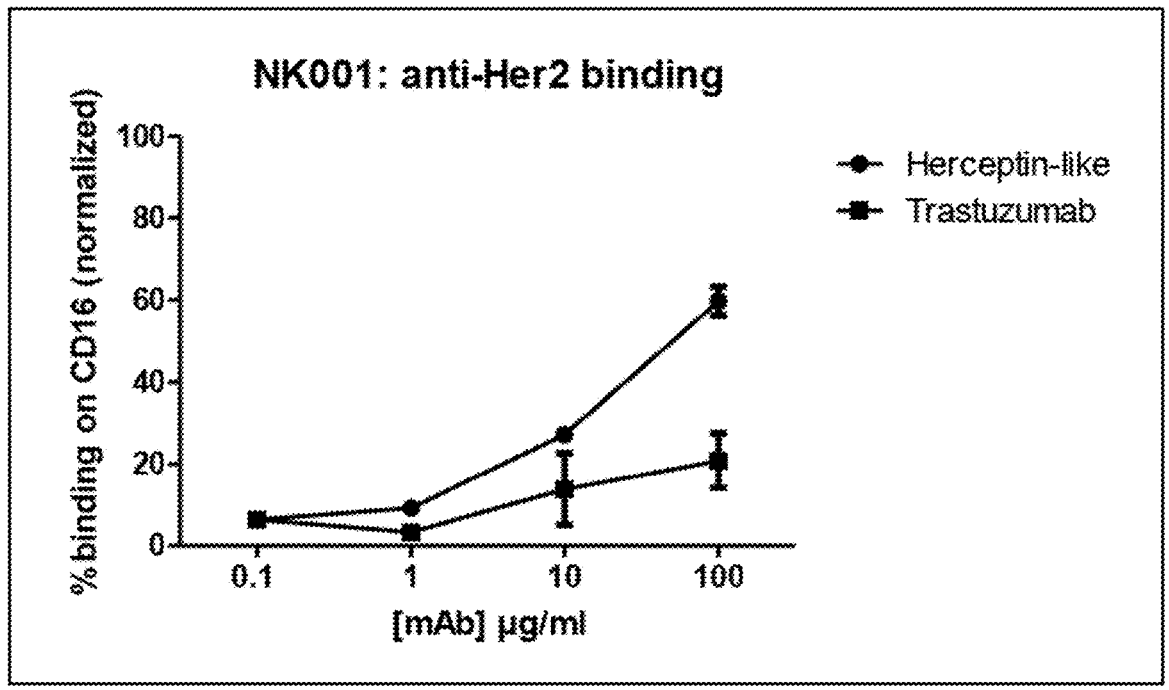
Figure 34:
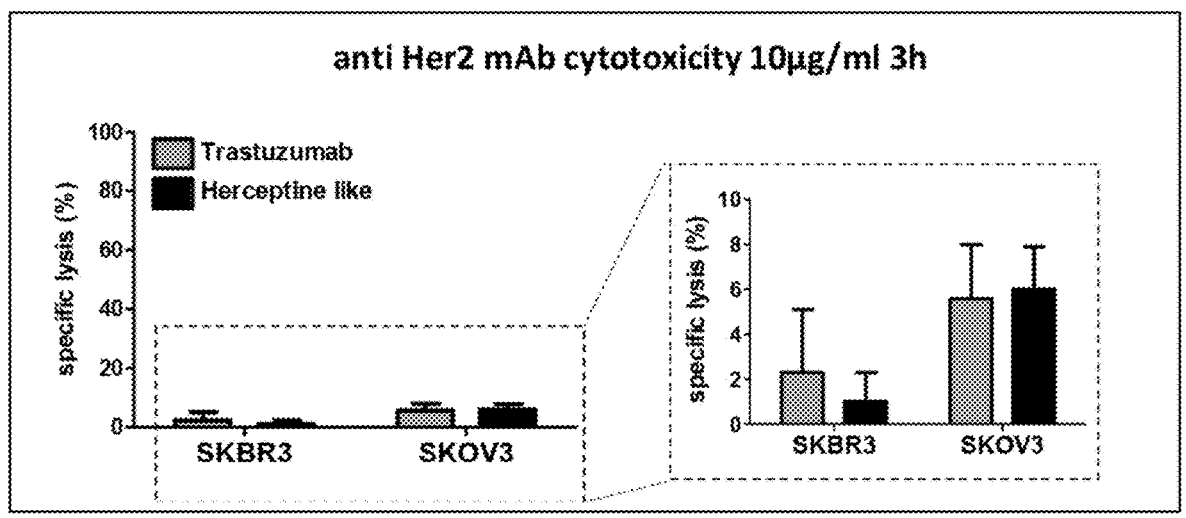

FIGS. 21A and 21B illustrate the direct binding analyse on Daudi (high CD20) (A) or on Raji (low CD20) (B) between TG20 and Rituximab FIGS. 22A and 22B illustrate the binding analyses by inhibition of CD20 labelling on Daudi (A) or Raji (B) cell line between TG20 and Rituximab FIGS. 23A and 23B illustrate the quantification of apoptotic cells in proportion to the dose of anti CD20 mAb after 24 h of incubation on Daudi (A) or Raji (B) cell line between TG20 and Rituximab FIGS. 24A, 24B and 24C illustrate the complement Dependent Cytotoxicity (CDC) analyse on Daudi (A) or Ri-1 (B) and SUDHL4 (C) cell line between TG20 and Rituximab FIG. 25 illustrates the cytotoxicity of anti CD20 mAb: dose effect between TG20 and Rituximab FIG. 26 illustrates ADCC on Daudi induced by NK-001+ anti CD20 mAb [10 µg/ml]: NK001 dose effect FIG. 27 illustrates ADCC on Daudi induced by NK-001+ anti CD20 mAb: mAb dose effect FIG. 28 illustrates the cytotoxicity of anti CD20 mAb on Daudi, Raji, Ri-1, SUDHL4 and HL60 cell line between TG20 and Rituximab FIG. 29 illustrates ADCC induced by NK-001 in synergy with anti CD20 mAb on Daudi, Raji, Ri-1, SUDHL4 and HL60 cell line between TG20 and Rituximab FIG. 30 illustrates the anti CD20 mAbs cytotoxicity on 8 different clinical samples between TG20 and Rituximab FIG. 31 illustrates ADCC induced by NK-001+anti CD20 mAbs on 8 different clinical samples between TG20 and Rituximab FIGS. 32A, 32B and 32C illustrate illustrates the reproducibility of the results obtained for ADCC with 3 lots of NK001 on p15-30 (A), p44 (B) and P16-01 (C) clinical samples between TG20 and Rituximab FIG. 33 illustrates Anti Her2 mAbs binding on NK001 between Herceptine-like and Trastuzumab FIG. 34 illustrates Anti-Her2 mAbs cytotoxicity induced by 10 g/ml of anti Her2 mAbs Herceptine-like and Trastuzumab on SKBR3 and SKOV3 cell line.

Figure 35A:
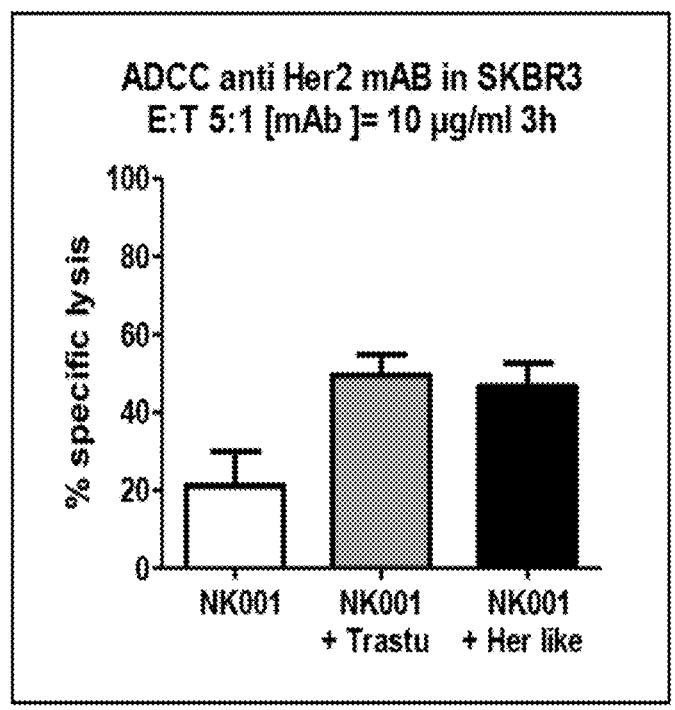
Figure 35B:
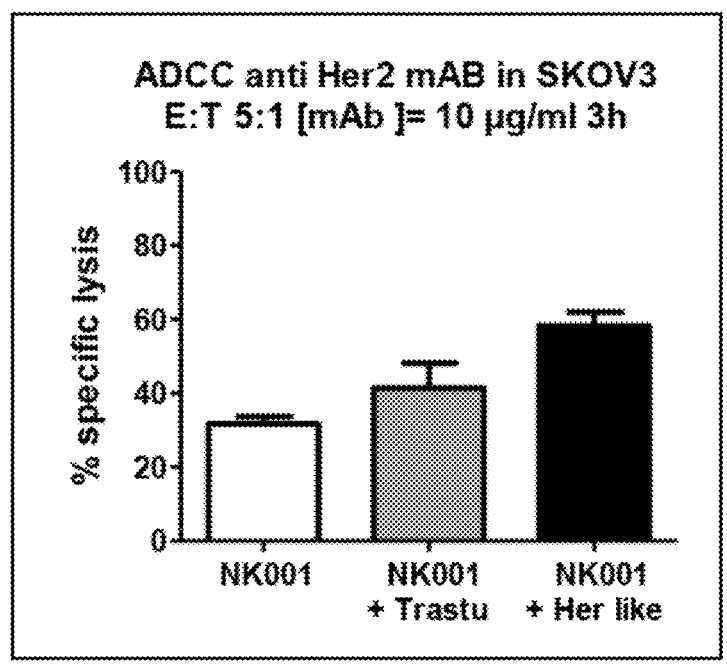
Figure 36:
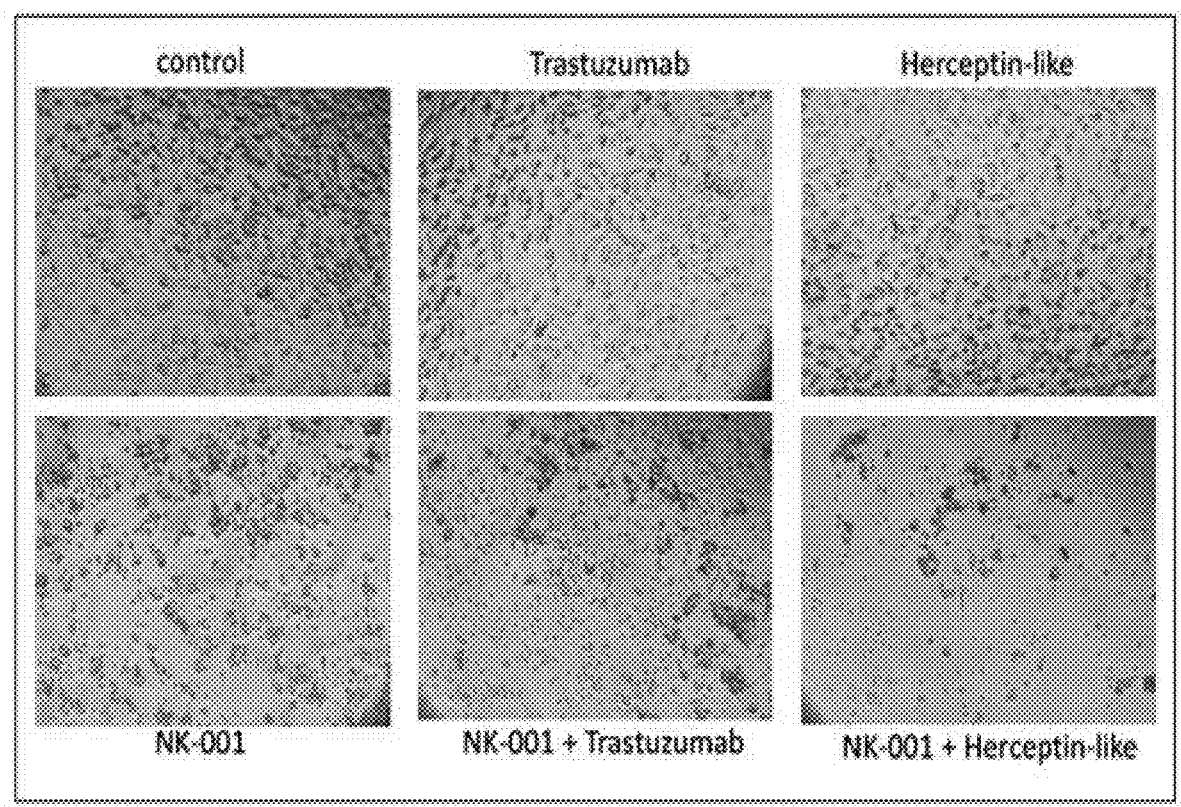
Figure 37:
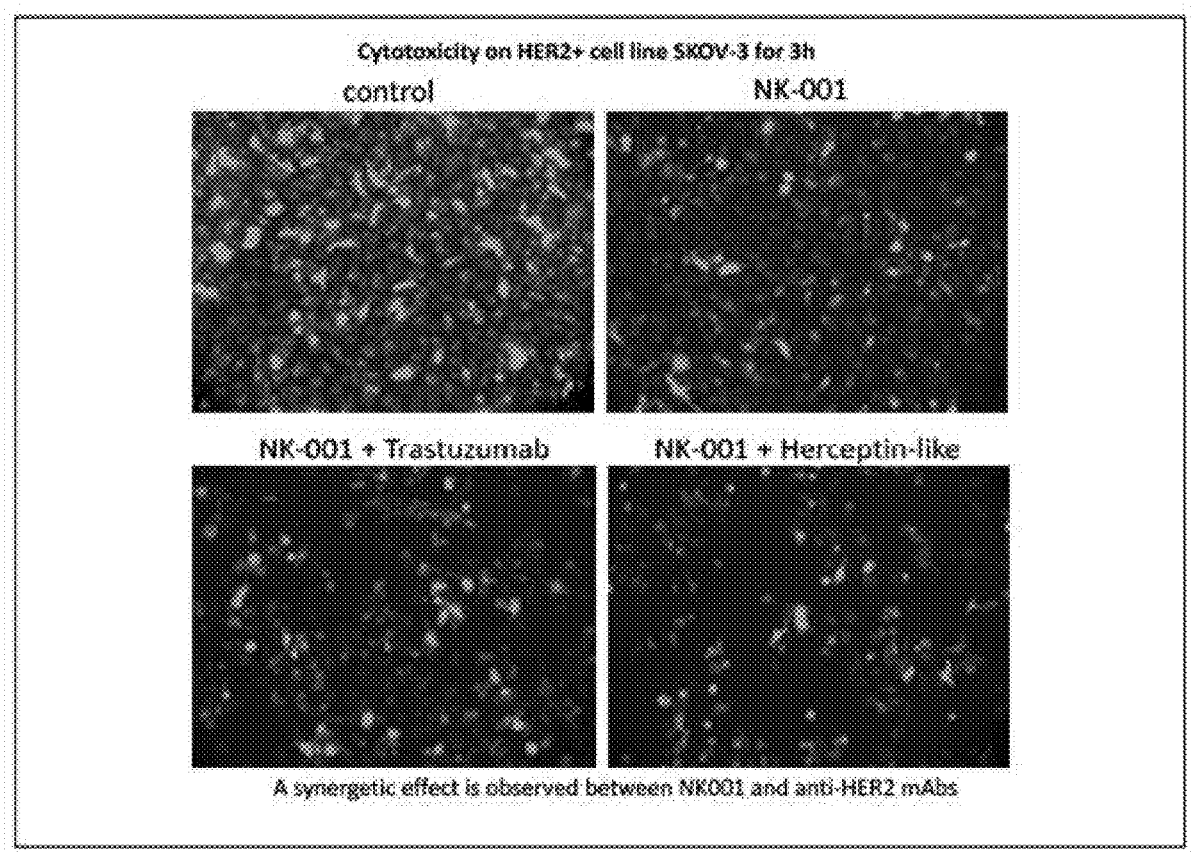

FIGS. 35A and 35B illustrate ADCC induced by NK-001+anti Her2 mAb [10 µg/ml] on SKBR3 (A) and SKOV3 (B) cell line with E:T ratio 5:1 for 3 h FIG. 36 represents images of bright field microscopy (10×) showing the synergic effect observed between NK001 and anti-Her2 mAbs cytotoxicity on SKOV3 cell line between Herceptine-like and Trastuzumab FIG. 37 represents images of fluorescence microscopy (Cyto tell green 10×) showing the synergic effect observed between NK001 and anti-Her2 mAbs cytotoxicity on SKOV3 cell line between Herceptine-like and Trastuzumab.

EXAMPLE 1: MATERIALS AND METHODS

Cells:

PLH (Example 4): no HLA-C1, ECACC bank no 88052047, IHW number 9047

This cell line was obtained by EBV immortalization of B lymphocytes coming from a scandinavian woman. This cell is completely HLA genotyped and have the particularity to express HLA Class I alleles from C group 2, A3/A11 and Bw4 types but not from C group 1 (complete informations on IMGT/HLA database).

This cell line is used as accessory cell for NK amplification/activation protocol because it allows to choose a specific HLA mismatch between accessory cell and UCBs (expressing HLA C group 1, and potentially the associated inhibitory receptor KIR2DL2/3). Being transformed by EBV infection increases its NK activation ability because of membranary expression of some viral induced ligands for NK activating receptors.

HOM-2 (Example 4): no HLA-C2, ID n° HC107505, IHW number 9005

This cell line was obtained by EBV immortalization of B lymphocytes coming from a Canadian/North American woman. This cell is completely HLA genotyped and have the particularity to express HLA Class I alleles from C group 1, A3/A11 and Bw4 types but not from C group 2 (complete informations on IMGT/HLA database).

This cell line is used as accessory cell for NK amplification/activation protocol because it allows to choose a specific HLA mismatch between accessory cell and UCBs (expressing HLA C group 2, and potentially the associated inhibitory receptor KIR2DL1). Being transformed by EBV infection increases its NK activation ability because of membrane expression of some viral induced ligands for NK activating receptors.

Media, Buffers and Cytokines:
1/ Density gradient cell separation medium of Ficoll and sodium diatrizoate used for the separation of lymphocytes: Histopaque-1077 from Sigma Aldrich, Saint Louis, MO, USA 2/ Kit for counting cells and looking at their viability with the Muse machine, labelling the cells with 7AAD and a fluorescent DNA probe: count and viability kit from Millipore, Darmstadt, Germany 3/ Cellular culture medium: RPMI 1640 Glutamax from Invitrogen, Carlsbad, CA, USA, purchased from France distributor Thermo Fisher Scientific 4/ Nutrient source in cellular culture medium: Fœtal Bovine Serum from Invitrogen, Carlsbad, CA, USA, purchased from France distributor Thermo Fisher Scientific 5/ Organic solvent for cells freezing: dimethyl sulfoxide, DMSO from B. Braun, Melsungen, Germany 6/ Buffer for flow cytometry labelling: PBS from Invitrogen, Carlsbad, CA, USA, purchased from France distributor Thermo Fisher Scientific 7/ Cytokine for NK amplification/activation: recombinant human rhIL-2 from ebioscience, San Diego, CA, USA 8/ Cytokine for NK amplification/activation: recombinant human rh-IL15 from Miltenyi, Bergisch Gladbach, Germany

EXAMPLE 2: EXAMPLE OF MANUFACTURING PROCESS

Figure 1A:
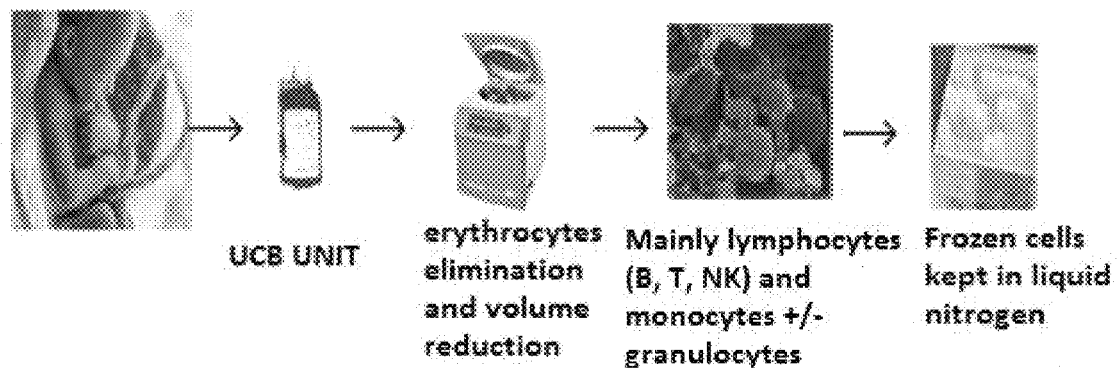
FIGS. 1-1 to 1-3 (sub-figures1, 2 and 3 of FIG. 1) is a schema illustrating an example of a manufacture process of the present invention.
Figure 1B:
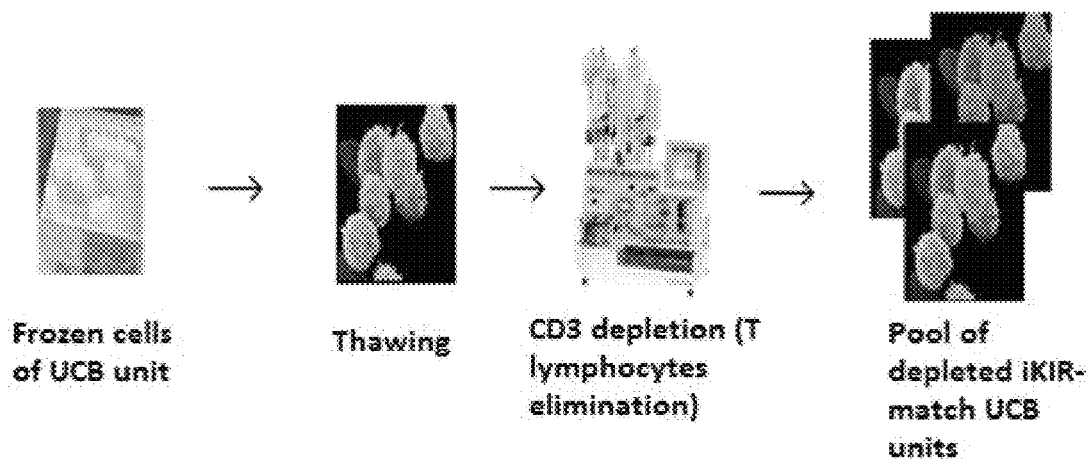
Figure 1C:
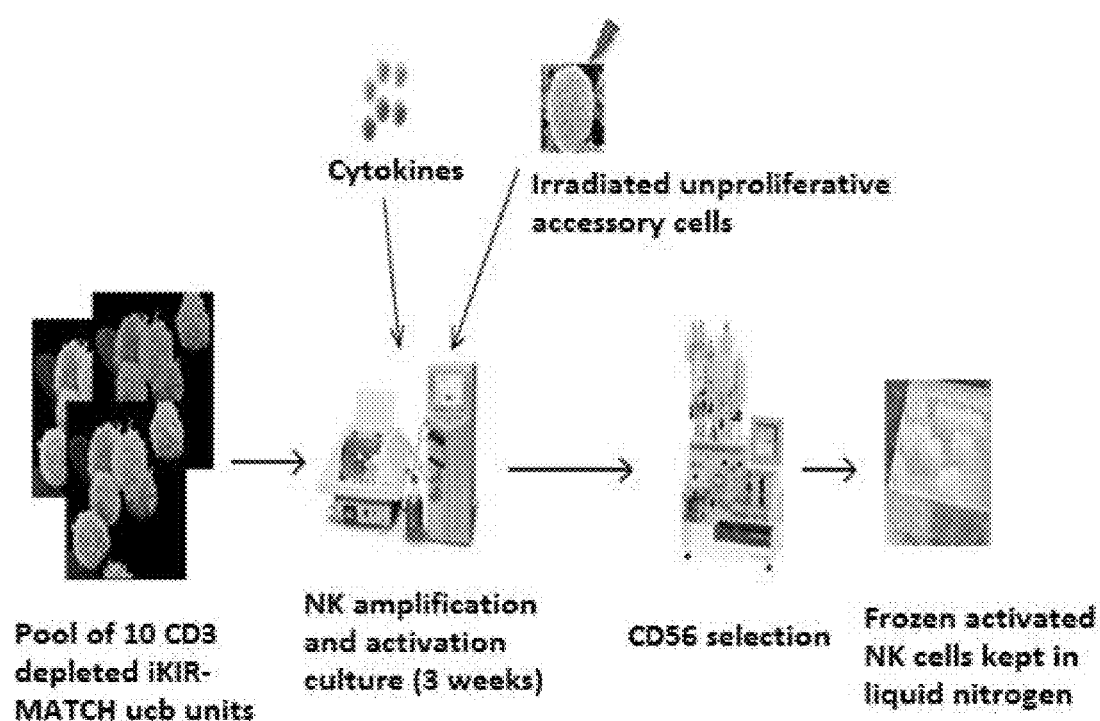
Figure 2:
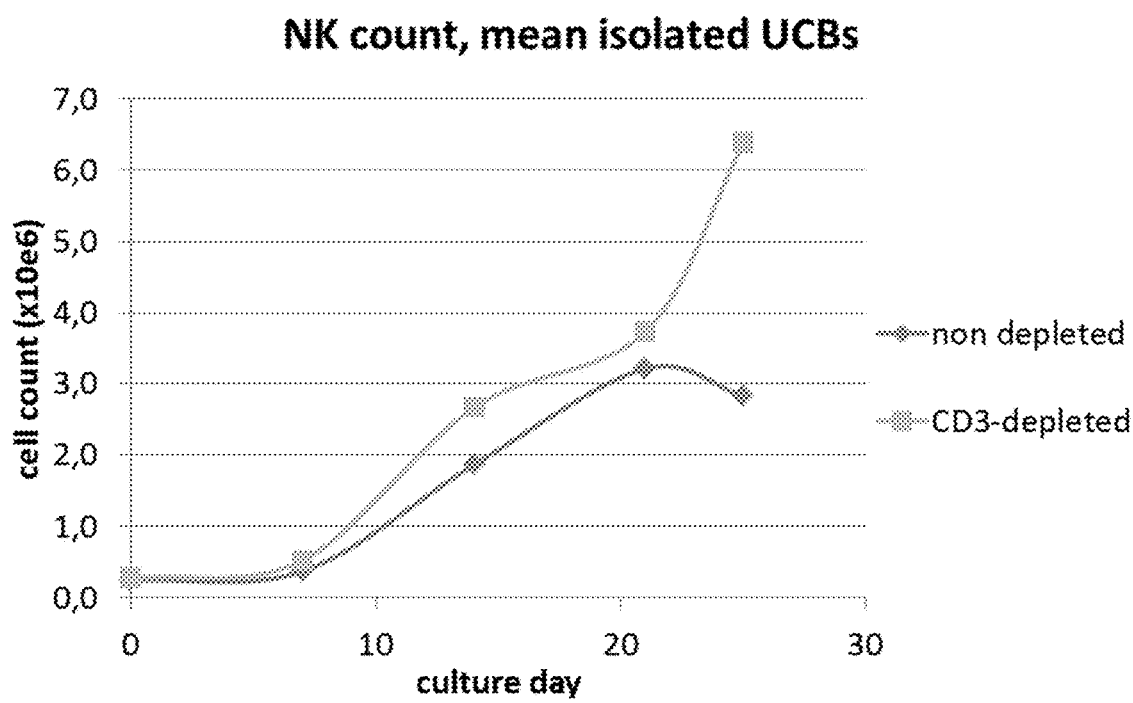
Figure 3:
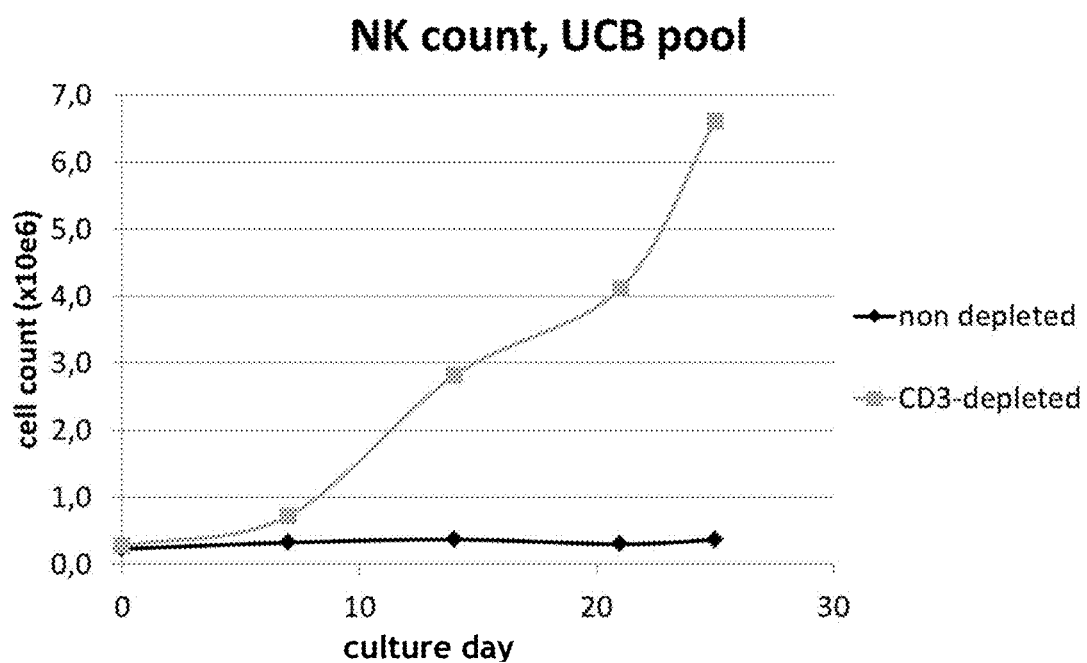

Process details: see FIGS. 1-1 to 1-3

UCBs were processed by ficoll UCB mononuclear cells isolation before first freezing.

CD3 depletions were done with a manual magnetic depletion kit.

Pooled UCBs present the same pattern for major HLA class I groups genotype (each HLA group is recognized by a major inhibitory KIR by NK cells): HLA A3/A11, recognized by KIR3DL2; HLA Bw4, recognized by KIR3DL1; HLA C group 1, recognized by KIR2DL2/3; HLA C group 2 recognized by KIR2DL1.

Pooled UCBs are activated with an accessory cell missing one of the HLA recognized by the expressed pooled UCBs iKIRs.

NK cells were amplified for 20-24 days.

Cytokines used are IL-2 (100 IU/ml) and IL-15 (5 ng/ml). These concentrations can be modified to obtain similar results.

Accessory cells are EBV-immortalized cell lines (cells expressing virus induced activating ligands) with specific HLA genotypes (one major HLA class I group missing).

Accessory cells can be irradiated by different ways with different irradiation doses (here we mainly used 20 seconds UV irradiation, but also 105 Gy gamma irradiation for the last experiment, that showed better amplification results).

Irradiated accessory cells can be used with or without prior cryopreservation: freshly irradiated cells or as irradiated cryopreserved cells (irradiation just before freezing).

For the 3 last experiments, irradiated accessory cells were added to the UCB cells at NK:accessory cell ratio 1:4, each 3-4 days (days 0; 4; 8; 12; +/−15; +/−18). Some results (previous and other not shown results) were obtained using ratio 1:2, or ratio total cells:accessory cells from 1:1 to 1:3, with addition frequencies from 3 days to 7 days. This parameter can be changed, still obtaining similar amplification/activation results.

In the experiments shown we didn't perform the CD56+ selection at the end of the process because NK cells derived from pooled CD3-depleted UCBs represented already more than 90% of alive cells at the end of the process. The CD56 selection step is not essential, but will probably improve NK purity and be preferable (and potentially totally required) for a pharmaceutical product.

Some steps of the process can be changed:

UCBs will be processed differently before first freezing, using a GMP-compliant method such as Hetastarch™ or PrepaCyte CB™ device (or other existing and clinically accepted method).

Even if current preclinical and clinical knowledge show that a iKIR-HLA mismatch gives better results than iKIR-HLA match, it is still possible that in our case iKIR-HLA has different influence in clinical outcome. So for the moment, the literature knowledge-based development should be with a process using NK/accessory cell mismatch and NK/patient same mismatch. Future preclinical and clinical data could change this parameter if unnecessary.

NK amplification culture duration can be optimized: from 14 to 28 days.

IL-2 and IL-15 concentrations can be optimized.

The CD3-depletion will be done with an automatic clinically accepted device such as cliniMACS.

The CD3-depletion can also be done just after erythrocyte elimination and volume reduction (maybe better results in term of NK recovery).

One of the results demonstrates that in some undefined cases, the CD3-depletion is not necessary for UCB pooled NK cells good amplification/activation.

To obtain an important quantity of activated multi-donors-derived NK cells characterized in a unique pharmaceutically defined lot, the preferentially CD3-depleted UCB units can be pooled at various moments of the process: before amplification culture, during amplification culture, or at the end of the amplification culture.

EXAMPLE 3: OBJECTIVES

1. First Experiment

Because it is known that T lymphocytes from different donors will kill each other by HLA differences recognition, and because NK cells need activator signal to be cytotoxic, we asked whether it is possible to pool CD3-depleted UCBs expressing the same major HLA groups (depending their recognition by inhibitory KIR's) but not the same HLA alleles. Total mononuclear cells and CD3-depleted mononuclear cells from 3 UCBs were pooled to verify if CD3-depletion was essential.

2. Second Experiment

Because we want to produce 4 class of NK cells presenting an iKIR-HLA mismatch for each major iKIR/HLA pair, we needed to investigate if success of pooling UCBs was only due to the first particular HLA genotyping used previously or could be reproduced with another HLA genotyping of UCBs: We asked whether another accessory cell line using another iKIR-HLA mismatch will allow NK amplification/activation from a pool of 3 CD3-depleted UCBs expressing the same HLA groups.

3. Third Experiment

Because to treat around 100 patients we will need to pool 10 UCBs, we asked whether a pool of 5 UCBs (half) expressing the same HLA groups allow the same NK amplification/activation.

EXAMPLE 4: EXPERIMENTS CARRIED OUT

1. First Experiment

UCB mononuclear cells obtained by Ficoll separation were cryopreserved, then thawed and CD3-depleted using a stem cell kit for a part. Three CD3-depleted or total UCBs with same the major HLA class 1 groups A3/A11+, Bw4+, C1+, C2+ genotype were pooled and cultured for 21-25 days with IL-2, IL-15 and irradiated accessory cells PLH (A3/A11+,Bw4+,C1−,C2+ genotype) added each 4 days.

2. Second Experiment

UCB mononuclear cells obtained by Ficoll separation were cryopreserved, then thawed and CD3-depleted using a stem cell kit. Three CD3-depleted UCBs with same the major HLA class 1 groups A3/A11−,Bw4+,C1−,C2+ genotype were pooled and cultured for 21-25 days with IL-2, IL-15 and irradiated accessory cells HOM-2 (A3/A11+, Bw4+,C1+,C2-genotype) added each 4 days.

3. Third Experiment

UCB mononuclear cells obtained by Ficoll separation were cryopreserved, then thawed and CD3-depleted using a stem cell kit. Five CD3-depleted UCBs with same the major HLA class 1 groups A3/A11−,Bw4+,C1+,C2− genotype were pooled and cultured for 21 days with IL-2, IL-15 and irradiated accessory cells PLH (A3/A11+,Bw4+,C1−,C2+ genotype) added each 4 days.

4. Evaluated Parameters

Alive NK cells were regularly counted using the MUSE Millipore system and flow cytometry characterization of cellular composition in the culture.

Expression of activating markers of NK cells was regularly evaluated by flow cytometry (CD16 for potent synergistic effect with monoclonal antibody therapies; CD69 as common activating receptor).

At day 20 of culture, cytotoxicity was evaluated against well-known K562 target cells, and tumoral cells for experiment 2 and 3 (2 h incubation with NK:K562 ratio 3:1, NK:purified B lymphoma cells ratio 3:1, NK:AML cells (in total PBMC sample of the patient) ratio 10:1).

EXAMPLE 5: RESULTS

1. First Experiment (See FIGS. 2 and 3)

UCB 1: HLA A11:01/A29:02, B35:01/B44:02, C04:01/C16/01>HLA A3/A11+, Bw4+, C1+, C2+

UCB2: HLA A11:01/A23:01, B35:02/B49:01, C04:01/07:01>HLA A3/A11+, Bw4+, C1+, C2+

UCB3: HLA A2/A3, B18/B51, C5/C14>HLA A3/A11+, Bw4+, C1+, C2+

NK proliferation from isolated UCBs show better results after CD3-depletion because T lymphocytes are in competition with NK cells for proliferation with the cytokines used (and CD8-T lymphocytes directed against EBV antigen are also stimulated by accessory cells).

NK from pooled CD3-depleted UCBs proliferate similarly than from isolated UCBs, but if UCBs are not CD3-depleted, T lymphocytes from the different donors are cytotoxic for the other one and NK cells cannot proliferate.

TABLE 1

| | UCB1 | UCB2 | UCB3 | Pooled UCBs | CD3-depleted UCB1 | CD3-depleted UCB2 | CD3-depleted UCB3 | Pooled CD3-depleted UCBs |
|---|---|---|---|---|---|---|---|---|
| NK Amplification Factor | 2.6 | 17.8 | 15.7 | 1.6 | 20 | 14.9 | 76.7 | 23.9 |
| % NK CD 16+ (ADCC-related) | 72.7 | 80.2 | 72.9 | 46 | 54.4 | 63.6 | 63.6 | 68.3 |

TABLE 1-continued

|  | UCB1 | UCB2 | UCB3 | Pooled UCBs | CD3-depleted UCB1 | CD3-depleted UCB2 | CD3-depleted UCB3 | Pooled CD3-depleted UCBs |
|---|---|---|---|---|---|---|---|---|
| % NK CD69+ | 86.7 | 88.6 | 94.7 | 94.3 | 92.9 | 95.1 | 96 | 86.6 |
| Common target lysis % | ND | ND | ND | ND | 64.1 | 58 | 50.9 | 52.7 |

NK amplification factor is relatively low in this experiment due to technical issue.

Activating receptors are well expressed, and cytotoxicity against common target K562 of cultured NK cells is highly better than with un-activated NK cells.

This experiment showed that pooling UCB with same major HLA groups genotyping for NK amplification is feasible but require prior CD3-depletion. Amplified NK cells are well-activated.

Figure 4:
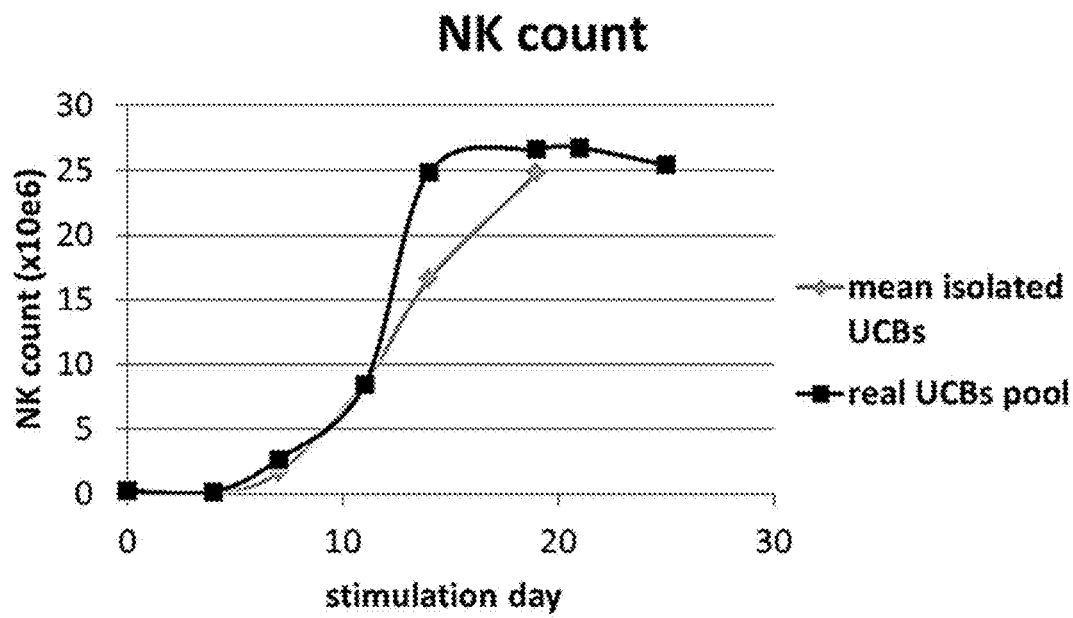
FIG. 4 illustrates the NK proliferation obtained from pooled CD3-depleted UCB units.

2. Second Experiment (See FIG. 4)

UCB1: HLA A01/02, B27:05/B40:02/C02:02/C15:02>HLA A3/A11−, Bw4+, C1−, C2+
UCB2: HLA A2/A31, B50/B51, C06:02/15:02>HLA A3/A11−, Bw4+, C1−, C2+
UCB3: HLA A23/A24, B44/B44, C4/C5>HLA A3/A11−, Bw4+, C1−, C2+

NK proliferation from pooled CD3-depleted UCBs with this new genotype is similar to NK proliferation with isolated CD3-depleted UCBs.

TABLE 2

|  | CD3-depleted UCB1 | CD3-depleted UCB2 | CD3-depleted UCB3 | Pooled CD3-depleted UCBs |
|---|---|---|---|---|
| NK Amplification Factor | 86.3 | 184.4 | 47.1 | 124.7 |
| % NK CD 16+ (ADCC-related) | 86.3 | 81.6 | 99.8 | 90 |
| % NK CD69+ | 99.6 | 94.9 | 99.2 | 98.5 |
| Common target lysis % | 93 | 97.6 | 90.1 | 87.7 |
| B Lymphoma tumoral cells lysis | 37 | 48.2 | 78.4 | 31.6 |

NK amplification factor is higher in this experiment (no technical issue), but can still be improved by protocol optimization specifically for the new accessory cell line.

Activating receptors are very well expressed. Cytotoxicity against common target K562 of cultured NK cells is highly better than with unactivated NK cells, and we observe a significant cytotoxicity against B lymphoma tumoral cells with a 2 hours incubation.

Pooling CD3-depleted UCBs with another major HLA groups genotype, and amplifying NK cells with another iKIR-HLA mismatch and another accessory cell line is feasible. Amplified NK cells are well-activated.

Figure 5:
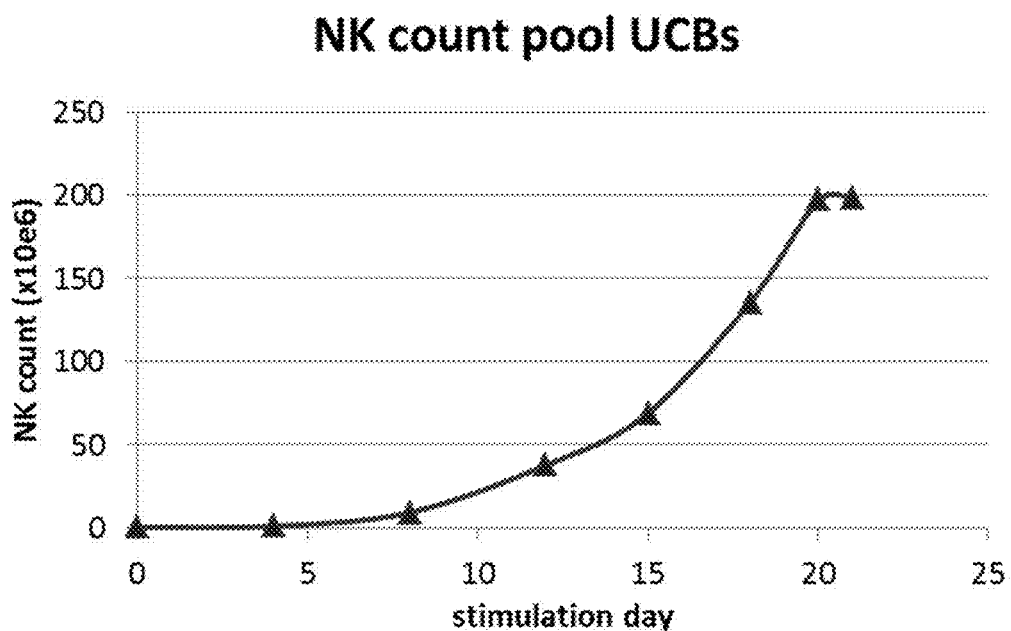
FIG. 5 illustrates the NK proliferation obtained from 5 pooled CD3-depleted UCB units.

3. Third Experiment (See FIG. 5)

UCBs: HLA A3/A11−, Bw4+, C1+, C2−

TABLE 3

|  | Pooled CD3-depleted UCBs |
|---|---|
| NK Amplification Factor | 583.2 |
| % NK CD 16+ (ADCC-related) | 81.7 |

TABLE 3-continued

|  | Pooled CD3-depleted UCBs |
|---|---|
| % NK CD69+ | 99.8 |
| Common target lysis % | 97.9 |
| AML umoral cells lysis | 10.4 |

NK proliferation from 5 pooled CD3-depleted UCBs is good.

NK amplification factor is higher in this experiment.

Activating receptors are very well expressed. Cytotoxicity against common target K562 of cultured NK cells is highly better than with unactivated NK cells, and we observe a small specific cytotoxicity against AML tumoral cells with a 2 hours incubation (but we couldn't observe cytotoxicity after 20 h because at this time patient cells died because of thawing).

Pooling 5 CD3-depleted UCBs and amplifying NK cells with an important amplification factor is feasible with our manufacturing process. Amplified NK cells are well-activated.

4. Complementary Results

Figure 6:
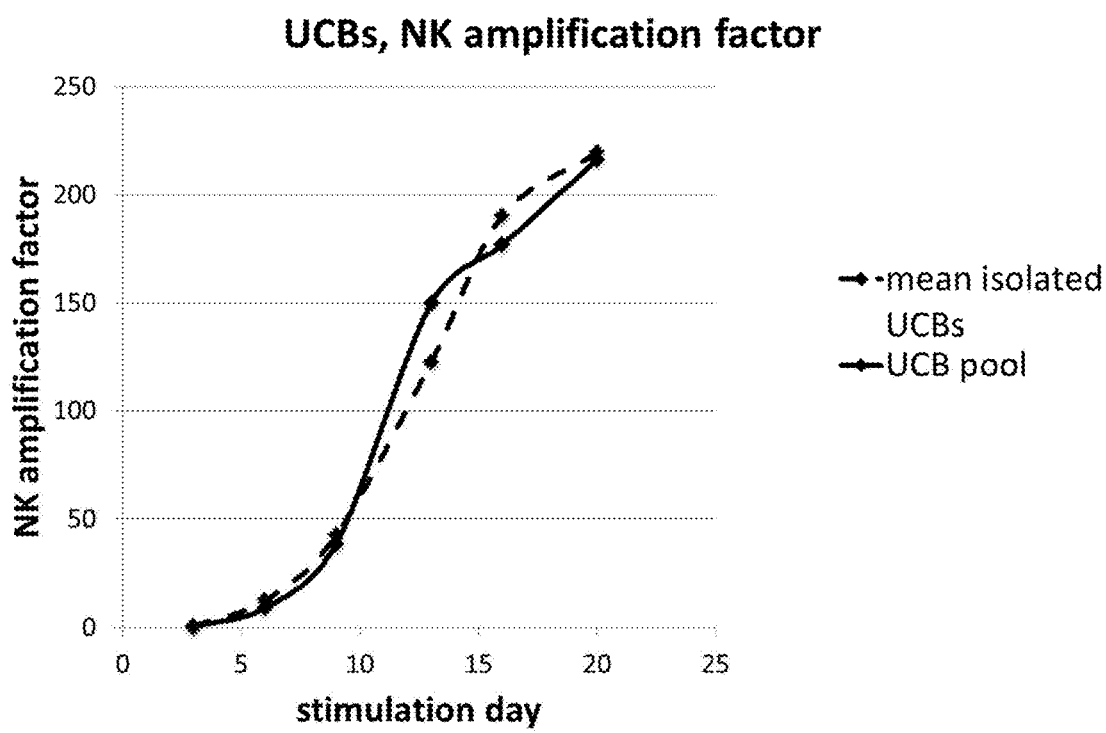
FIG. 6 illustrates the NK proliferation obtained from pooled UCB units without prior CD3-depletion.

Experiment showing good amplification of NK cells from pooled UCBs without prior CD3-depletion (no reproducibility assay): (see FIG. 6)

3 iKIR-HLA mismatch UCBs amplified with PLH:

UCB 1: HLA A2:01/A68:01; B38:01/B57:01; C6:02/C12:03>C1+, C2+, A3/A11−, Bw4+

UCB 2: HLA A1:01/A2:01; B52:01/B57:01; C6:02/C12:02>C1+, C2+, A3/A11−Bw4+

UCB 3: HLA A02/02; B15:09/B50:02; C06/C07>C1+, C2+, A3/A11−, Bw4−

NK amplification can be similar in isolated or pooled UCBs without prior CD3-depletion.

Figure 7:
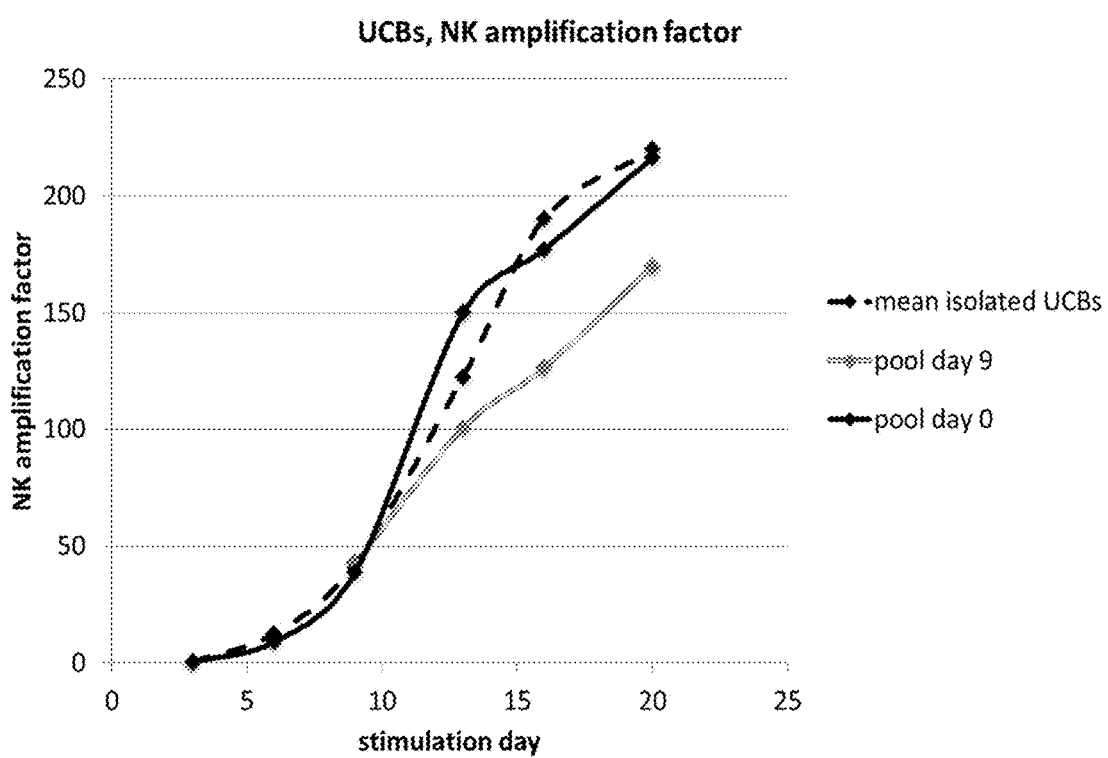
FIG. 7 illustrates the NK proliferation from pooled UCB units after 9 days of culture with CD3-non depleted UCBs.

Experiments showing possibility of pooling after 9 days culture (with CD3-non depleted UCBs):

1/ same previous experiment (see FIG. 7)

TABLE 4

|  | UCB1 | UCB2 | Pool D0 | Pool D9 |
|---|---|---|---|---|
| % B Lymphoma lysis | 74 | 91 | 90 | 91 |

It is possible to pool 9 days activated NK cells (here without prior CD3-depletion) keeping a significant but lower NK amplification.

Figure 8:
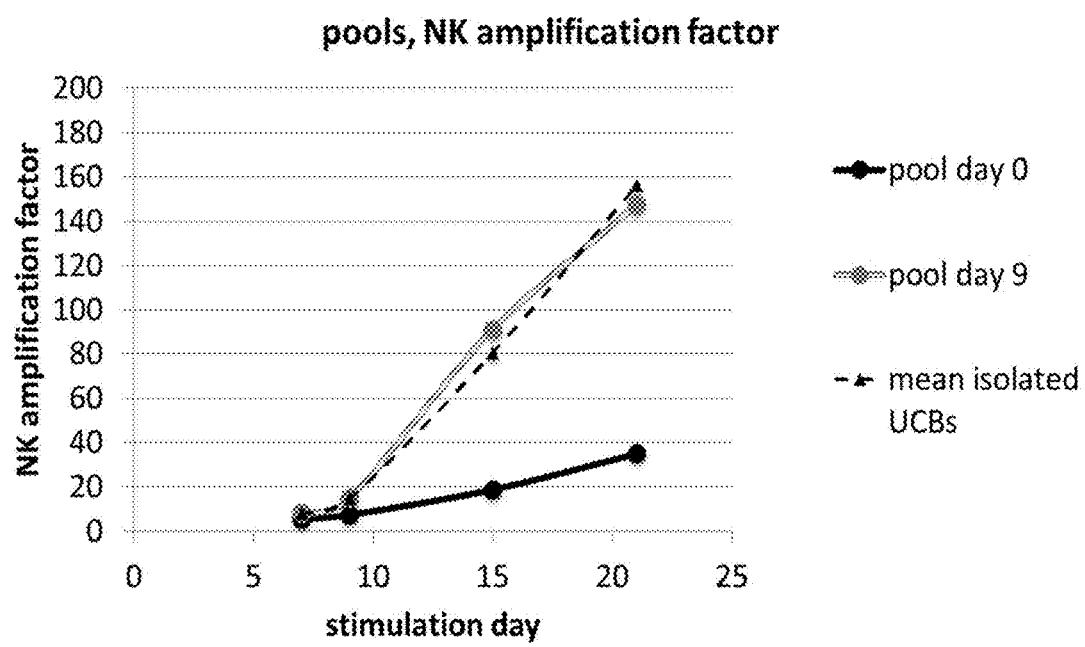
FIG. 8 illustrates the NK proliferation amplification factor obtained with 2 KIR-HLA matched UCBs and amplified with PLH accessory cells

2/ Experiment with 2 iKIR-HLA matched UCBs amplified with PLH: (see FIG. 8)

UCB 1: HLA A11:01/A29:02, B35:01/B44:02, C04:01/C16/01>HLA A3/A11+, Bw4+, C1+, C2+

UCB2: HLA A11:01/A23:01, B35:02/B49:01, C04:01/07:01>HLA A3/A11+, Bw4+, C1+, C2+

When NK didn't amplify properly in CD3-non depleted, pooling UCBs after 9 days amplification (increasing NK % and NK activation status, but still with high T lymphocytes %) seemed to overcome the problem. They showed an in vitro similar good cytotoxicity against B lymphoma tumoral cells (overnight, ratio E:T 1:1).

Figure 9:
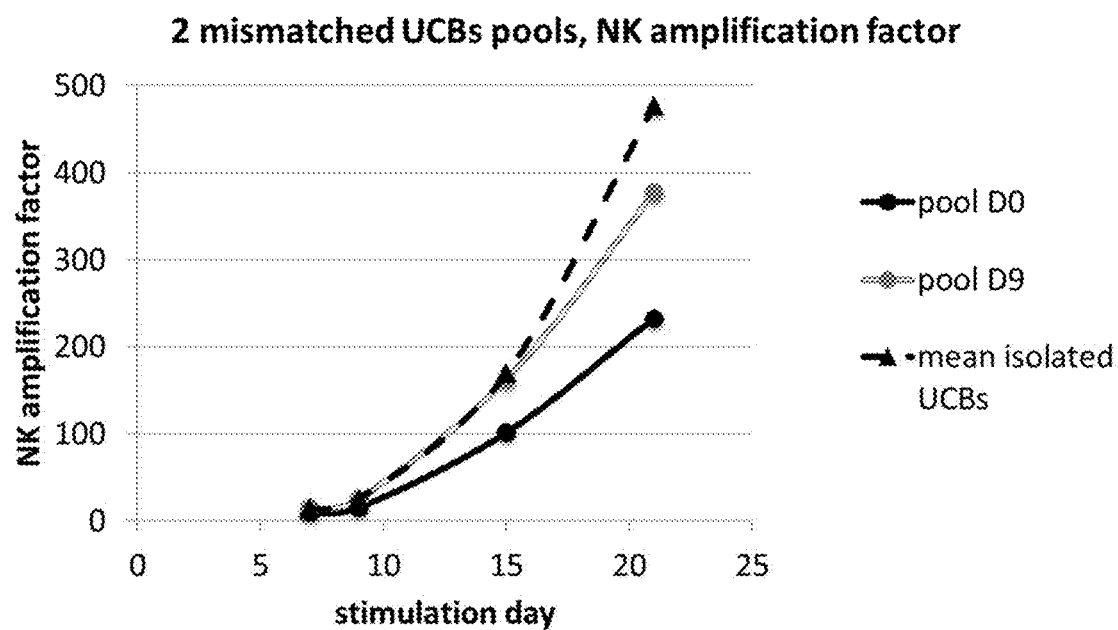
FIG. 9 illustrates the NK proliferation amplification factor obtained with 2 KIR-HLA mismatched UCBs amplified with PLH accessory cells.

3/ Experiment with 2 iKIR-HLA mismatched UCBs amplified with PLH: (see FIG. 9)

UCB1: HLA A02:02/30:01, B42:01/B53:01, C04:01/17:01>HLA A3/A11−, Bw4+, C1−, C2+

UCB2: HLA A11:01/A23:01, B35:02/B49:01, C04:01/07:01>HLA A3/A11+, Bw4+, C1+, C2

TABLE 5

|  | UCB1 | UCB2 | Pool D0 | Pool D9 |
|---|---|---|---|---|
| % B Lymphoma lysis | 74 | 92 | 96 | 97 |

NK cells from CD3-non depleted iKIR-HLA mismatched pooled UCBs showed a lower amplification factor, and pooling these UCBs after 9 days amplification gave better NK amplification. They showed an in vitro similar good cytotoxicity against B lymphoma tumoral cells (overnight, ratio E:T 1:1).

EXAMPLE 6: PERSPECTIVES

1. Process Optimization

Preferably, the manufacturing process of pooled activated/expanded NK cells according to the present invention will be adapted to the pharmaceutical regulatory obligations, and every step of the process adapted for the best quality guarantee.

First, and for example, acceptance criteria of UCB units must be set, such as more than 1.4 or 1.6 $10^6$ total nucleated cells (currently 1.85 $10^6$ total nucleated cells for our local UCB bank), with potentially a minimal threshold for the NK percentage such as 7% (3-15% NK generally observed in UCB total nucleated cells).

The "Ficoll" method used in the above examples for UCB mononuclear cells (UCBMC) isolation can be easily replaced by well-adapted standard and well-known method for clinical application, and pharmaceutical conditions, for example using a closed sterile single use system with bags, using adapted procedures such as HES 6% and centrifugations erythrocytes elimination and volume reduction, or Prepacyte CB isolation system. These systems certainly improve the total nucleated cell recovery in the first step.

Preferably, CD3-depletion of UCBMCs can be better adapted to regulatory compliances and/or GMP process for pharmaceutical uses, for example with an adapted clinically upgradable material such as CliniMACS™, and by determining the best step time for CD3-depletion whether it is needed, before or after first cryopreservation step for the best cell recovery and the best CD3-depletion quality.

Preferably, the freezing, cryopreservation and thawing procedures for UCBMC can be improved using authorized procedures for clinical applications after validation of the manufacturing process. Adapted material for bag closed system can be used and cryopreservation conditions (media, cell concentration) can be easily optimized by the skilled person for the method of the present invention. These optimization steps only should certainly improve the total cell recovery after thawing. In the same time, the acceptance criteria for each thawed UCBMCs to go further into the manufacturing process according to pharmaceutical guidelines should be set.

Preferably, HLA-genotyping and inhibitory KIR expression evaluation procedures should be validated to select the different UCB units allowed to be pooled for the amplification/activation step: selection criteria should be set for each lot.

Preferably, GMP compliant upgradable accessory cells, whether they will be included in the method of the invention, with a final screening on NK amplification: activation for clones selection. Final accessory cells must be well-characterized for use in a therapeutic agent production procedure. This optimization step could also improve NK amplification/activation results.

Preferably, irradiation procedure will be optimized and validated for the best amplification/activation results with clinically adapted quality parameters, and acceptance criteria of cryopreserved irradiated accessory cells lots will be set, including unproliferation evaluation, cells viability, EBV inactivation . . . etc.

Irradiated accessory cells exact addition procedure will be optimized for the final clones used in the process including accessory cells.

Preferably, a dynamic culture closed system in bioreactors will be used for amplification/activation step with at least 5, preferably 10 pooled UCB units, such as the Wave System™ (GE Healthcare) already tested for NK culture.

Preferably, culture medium used for the amplification/activation step, using animal serum-free media such as X-VIVO™ media from Lonza, CellGro SCGM™ from Cellgenix or AIM V™ from Invitrogen (already tested for NK cultures) can be used.

Preferably, CD56 positive selection of amplified/activated NK cells using an adapted clinically upgradable material such as CliniMACS™, will be used.

2. Pharmaceutical Development: Final Product Characterization and Acceptance Criteria Preferably, a step of acceptance criteria of final amplified/activated products must will be included in the process, including product identification steps (genetic stability, chimerism, phenotype) and a standard potency evaluation procedure.

Preferably, the genetic stability of NK cells before and after the process of the present invention will be checked, looking at their karyotype (for example by G-banded karyotyping or cytoscanHD microarray methods well-known by the filled person), and the chimerism of the final pooled NK cells from the different donors must be defined (for example by standard multiplex PCR STR methods).

Preferably and to better identify and characterize the final product and to define acceptance criteria, the expression of more NK phenotypical markers (NKG2D, NKG2C, CD94, NKp44, NKp30, NKp46, CD158 . . . ) will be evaluated (for example by flow cytometry).

Preferably, each product lot will be tested with a validated cytotoxicity assay against commonly used well-known target cells Preferably, the absence of contaminations such as bacteria, fungi, mycoplasma and viruses (particularly EBV) must be verified during or after the final step of the process, as the absence of endotoxins and cytokines used during the manufacturing process.

EXAMPLE 7: POOLED UCBS NK CELLS CYTOTOXICITY ASSOCIATED WITH ANTI-CD20 ANTIBODIES

Material and Methods

UCBs:
  HLA A3/A11+, HLA Bw4+, HLA Cg1+et HLA Cg2−;
  Activated in presence of PLH (HLA Cg1−) and thus, no inhibition via their KIR2DL2 et KTR2DL3
  Alloreactivity of the NK HLA Cg1+KIR2DL2/KIR2DL3+ against the tumoral cells (HLA Cg1)

UCBs Treatment:
  Production of a population of expanded and activated NK cells from 5 UCB units:
    From the 5 UCB units exhibiting preferably the same pattern for major HLA class I groups genotype
    Erythrocytes-depleting each UCB unit by density gradient separation, by Ficoll-Paque® density gradient separation;
    Optionally (see second experiment), the population of cells obtained is frozen, kept in liquid nitrogen and thawed before their use
    The 5 Ficoll/depleted nUCB units cells obtained in the preceding step are pooled.
  The pooled NK cells obtained are thus expanding and activating by contacting the NK cells contained in the pool, in a suitable medium to produce said population of pooled expanded and activated NK cells as described before, for an expanding/activation step(s) total duration comprised between 9 and 28 days
    Irradiated PLH at D0, D5, D8, D12;
    Culture medium: RPMI FBS 10% IL-2 100 IU/ml I-15 5 ng/ml;
    Amplification factor at D21: 256.6; 99.5% of NK cells, 100% CD69+, 84.6% CD16+(directly used for cytotoxicity test).
    After freezing/Thawing, we obtained 44.9% of CD16+.
    Patient p45: lymphoma B tumor sample (97% tumoral cells);
    Patient p46: B-cell chronic lymphocytic leukemia (B-CLL) (91% tumoral cells)
  For these two cases, the patient cells sample are thawing and, 1-2 h after thawing, are used in cytotoxicity assay
    50,000 target cells/microwell, 200 µl in final (96-well microplate conical bottom), RPMI medium FBS (Foetal bovine serum) 10%, IL-2 100 IU/ml, +/−rituximab 10 µg/ml, incubation at 37° C., 5% $CO_2$.

Figure 10A:
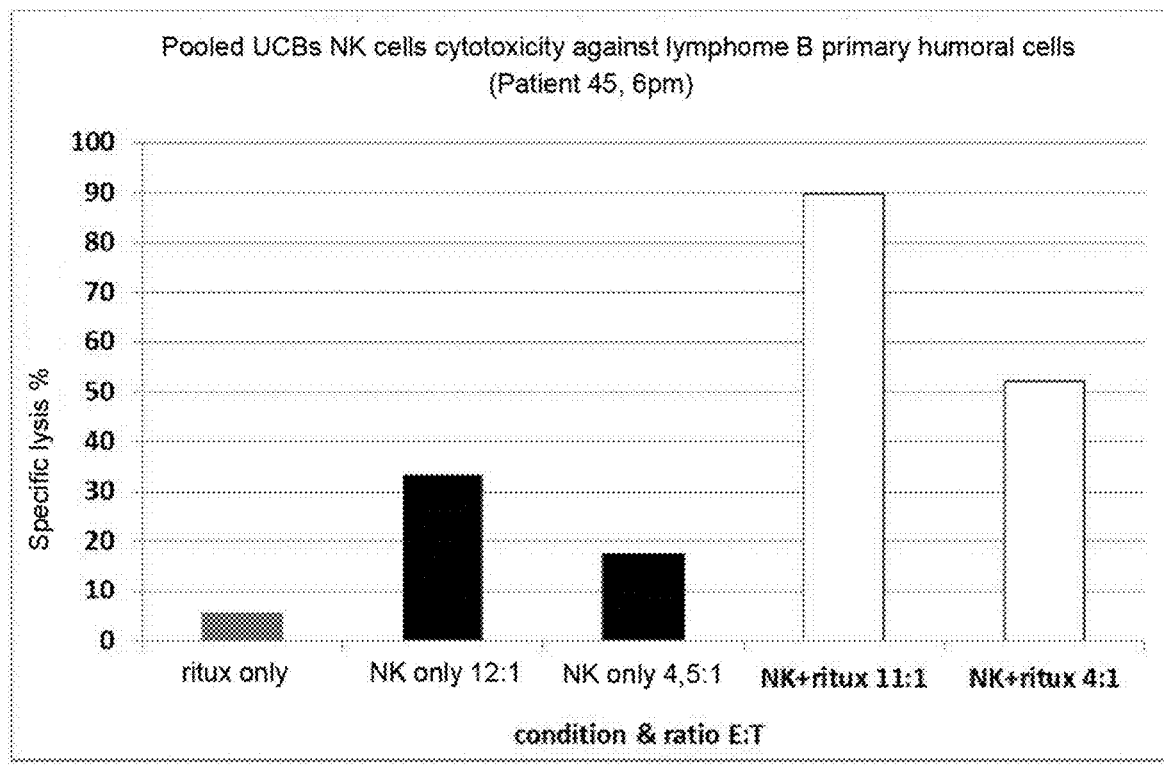
FIG. 10A-10B illustrates Example 7, first experiment.
Figure 10B:
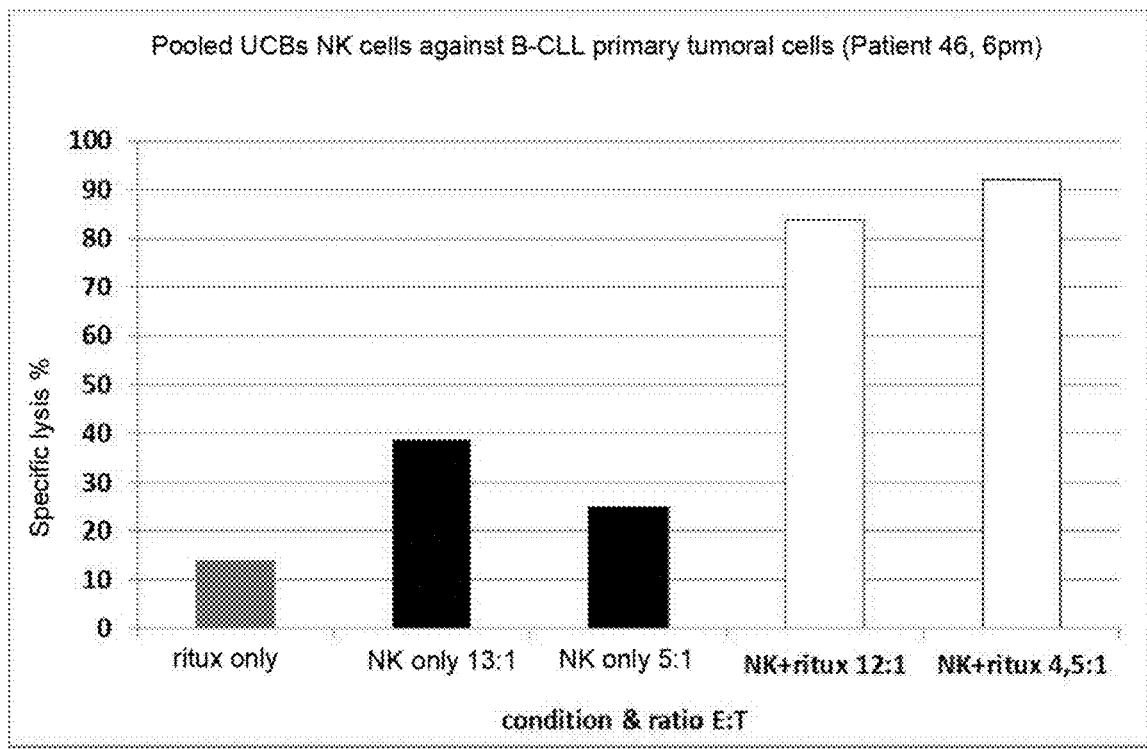

First Experiment (See FIGS. 10A-10B)

Fresh (not freezed-thawed) pooled UCBs NK cells are used (21 days after their production);
Overnight (18 h) incubation
Ratio NK cells/tumoral cells as indicated in the FIGS. 6A-6B.

Results

No cytotoxicity is observed on non NK (CD56−) and non B (CD19−) cells even when the ratio used is the strongest one;
In presence of rituximab, the pooled UCBs NK cells mediate Antibody-Dependent Cell-mediated Cytotoxicity on cellules CD20+tumoral cells.

Figure 11A:
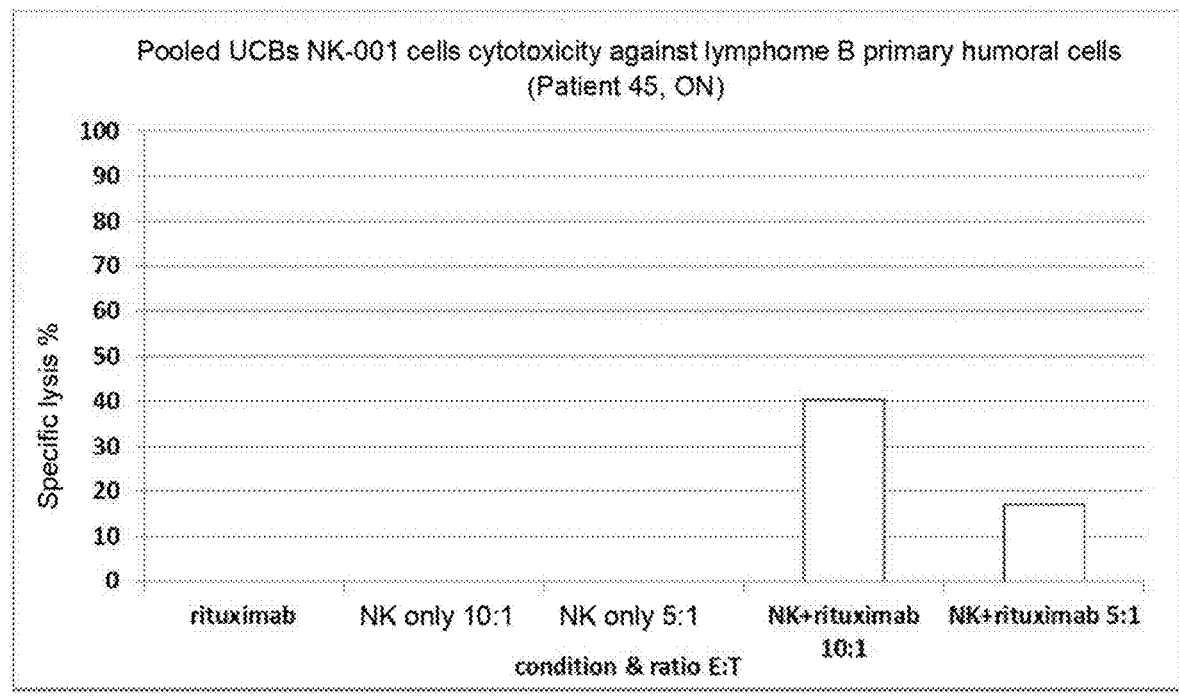
FIG. 11A-11B illustrates Example 7, second experiment.
Figure 11B:
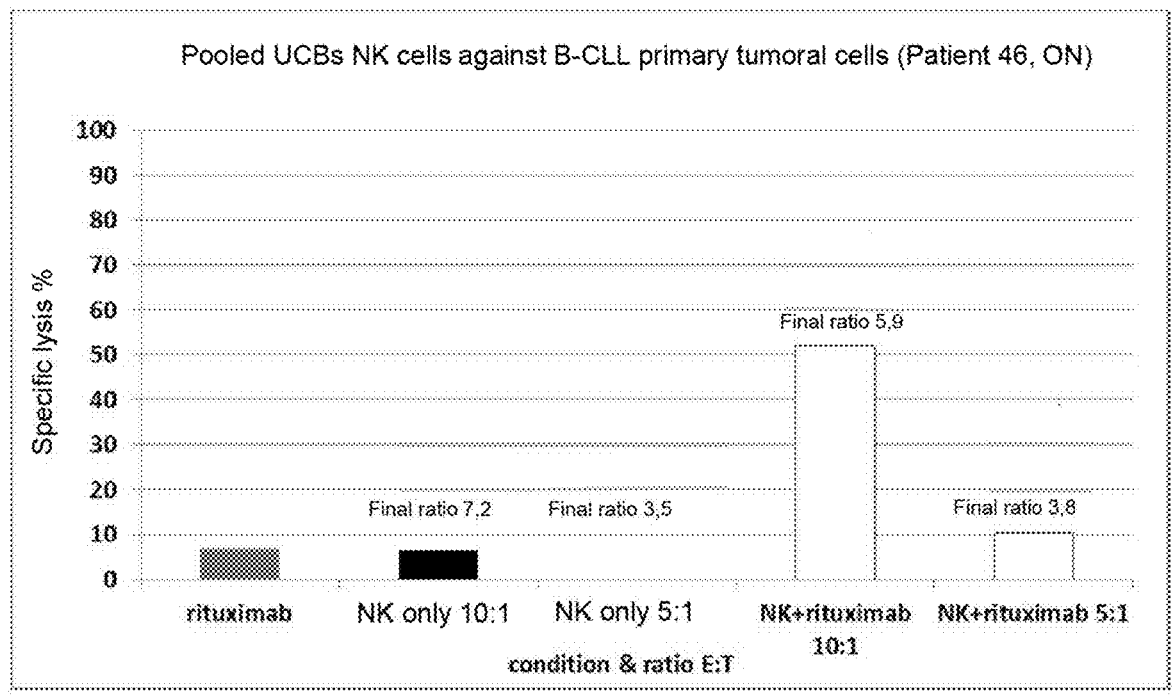

$2^{nd}$ Experiment (see FIGS. 11A-11B)

Same Lot of pooled UCB units NK cells as the first experiment but freezed at D21 et thawed at the day of cytotoxicity test;
Incubation 24 h with the ratio indicated in the FIGS. 11A-11B (we can note that the ratios at the end of the cytotoxicity test are lower than at the beginning (death of part of the NK cells after 24 h following the thawing (6 in place of 10 and 3.5-4 in place of 5).

Results

In presence of rituximab, the pooled UCBs NK cells mediate Antibody-Dependent Cell-mediated Cytotoxicity on cellules CD20+tumoral cells.

EXAMPLE 8: ANTI CD20 TG20 ACT AS A SYNERGIC MANNER TO INCREASE ADCC INVOLVED BY NK CELLS

A) Chimeric Anti-CD20 Antibody TG20

In order to increase NK cells infusion treatment efficiency, the therapy will be combined with the use of anti CD20 monoclonal antibody: TG20 (LFB S.A., Les Ulis, France, TG Therapeutics Inc., New York, N.Y.) to decrease progression or cure hematological cancers such as non-Hodgkin B-cell lymphoma or B-Cell chronic lymphocytic leukemia.

TG20 is also called TG-20, Ublituximab, LFB-R603, TG-1101 or TGTX-1101.

For more details of the structure of the chimeric anti-CD20 antibody TG20/R603 (low fucose/afucosylated mAb), see the patent application WO2012/175874 (published on Dec. 27, 2012

According to the National Cancer Institute drug dictionary, TG20 (Ublituximab biosimilar obtained from milk of transgenic mice according to the LFB US rPRO technology) is a chimeric recombinant IgG1 monoclonal antibody directed against human CD20 with potential antineoplastic activity. Ublituximab specifically binds to the B cell-specific cell surface antigen CD20, thereby potentially inducing a B cell-directed complement dependent cytotoxicity (CDC) and antibody-dependent cell-mediated cytotoxicity (ADCC) against CD20-expressing B cells, leading to B cell apoptosis. CD20 is a non-glycosylated cell surface phosphoprotein that is exclusively expressed on B cells during most stages of B cell development and is often overexpressed in B-cell malignancies. Ublituximab has a specific glycosylation profile, with a low fucose content, that may enhance its ADCC response against malignant B cells (obtained from Rac cell lines Y2B/0 (ATCC #CRL-1662, see WO2012/175874, page 30, Example 2).

NK cells are able to interact with cytotoxic monoclonal antibodies and lyse cells which are recognized by these monoclonal antibodies. This property is well known as "antibody dependent cellular cytotoxicity" (ADCC).

This example demonstrates in vitro on clinical samples from patients that anti CD20 TG20 act as a synergic manner to increase ADCC involved by expansed and activated NK cells from pooled umbilical cord blood.

NK cells are produced regarding good manufacturing process (GMP) and characterized in order to have 99% of purity at day 21.

ADCC assays were performed on patient samples and also on 5 cell lines.

B) Antibody Dependent Cellular Cytotoxicity Assay a) On Patient Samples

Patient samples are coming from CHU, Montpellier, France.

Ratio E:T «Effector (NK cells): Target (=patient cells)» are 5:1, 15:1

As 50 000 target cells for 250 000 or 750 000 NK cells

Monoclonal Antibody (mAb) concentration: 10 µg/ml

TG20 is compared to gold standard Rituximab (Genentech, Roche)

TG20 and Rituximab are pre-incubated 15 min at room temperature.

After NK addition, incubate 24 h at 37° C. before flow cytometry analysis

Results: (see FIGS. 12A, 12B and 12C)

At this time, we have tested one B-lymphoma (p45) and two B-CLL (B-cell Chronic Lymphocytic Leukemia) (p46, p53) patients.

Variation of E:T ratio observed between assays is technically experience-dependent.

Each sample of patient respond as an independent manner to the NK treatment alone.

We observed for low E:T ratio 49%, 23% or 37% of lysis induced by NK cells alone for respectively p45, p46 and p53 patients. With a higher E:T ratio lysis induced by NK cells alone increased as 58% for p45 and 39% for p46.

MAb (TG20 or Rituximab) treatment alone is poorly efficient.

Association of NK cells and mAb increase dramatically percentage of target lysis in all cases. Compare to treatment of NK cells alone, we observe an increase of about 40% with the combination of NK cells+mAb in patient p45, an increase of 145% for low E:T ratio and 50% for high E:T ratio in patient p46 and an increase of 29% for NK+TG20 10 µg/ml and 18% for NK+Rituximab 10 µg/ml in patient p53.

For instance we do not observe any significant difference between efficiency of TG20 and Rituximab. Moreover each response to combination of NK+mAb is patient dependent.

b) On Cell Lines

Cell LINES:

Daudi (Burkitt lymphoma, high CD20), Raji (Burkitt lymphoma, low CD20), SUDHL4 (DL-BCL GC (Diffuse Large B Cell Lymphoma Germinal Center)), R1-1 (DL-BCL ABC (Activated B-Cell)) and HL60 (AML (Acute Myeloid Leukaemia)).

Ratio E:T «Effector (NK cells): Target (=cell line cells)» are 1:1, 2:1 and 3:1

As 50 000 target cells for 50 000, 100 000 or 150 000 NK cells

Monoclonal Antibody (mAb) concentration: 0.1; 1; 5 et 10 µg/ml

TG20 is compared to gold standard Rituximab (Genentech, Roche)

TG20 and Rituximab are pre-incubated 15 min at room temperature.

After NK addition, incubate 4 h at 37° C. before flow cytometry analysis

Results: ADCC and synergic action of mAb and NK cells on cell lines (see FIGS. 13A, 13B and 13C) and anti-CD20 dose effect (ratio E:T: 1/1) ((see FIGS. 14A, 14B, 13C and 14C)

1:1 E:T ratio is more appropriate to study ADCC and synergic action of mAb and NK cells. To evaluate dose effect of mAb we should start at 5 µg/ml of mAb as a minimal dose.

On AML HL60 cell line we do not observe a real synergic action of mAb and NK which is a normal result as HL60 cells do not exhibit CD20 on surface (data not shown).

At this time, TG20 seems to be as efficient as Rituximab. Furthermore, we observe on SUDHL4 cell line better results of synergic action between TG20-NK cells than Rituximab-NK cells.

Binding of TG20 and Rituximab were also tested on Daudi and Raji cell lines and no significate results were observed (data not shown). On Daudi cells: TG20 EC50=75.6 ng/ml; Rituximab EC50=105 ng/ml. On Raji cells: TG20 EC50=229 ng/ml; Rituximab EC50=230 ng/ml. (EC50 is concentration of mAb to obtain 50% of binding).

Inhibition of CD20 after mAb binding was also analyzed on Daudi and Raji cells (data not shown). On Daudi cells we observed: TG20 EC50=4 µg/ml; Rituximab EC50=3.4 µg/ml. On Raji cells we observed: TG20 EC50=5 µg/ml; Rituximab EC50=3.7 µg/ml. The differences observed for both mAb on each cell line are not significant. EC50 is concentration of mAb to obtain 50% of CD20 inhibition.

Finally, we have performed complement dependent cytotoxicity on the 5 cell lines and we did not observe any difference between lysis induced by complement with TG20 or Rituximab (data not shown).

EXAMPLE 9: ANTI CD20 RITUXIMAB AND UBLITUXIMAB R603 ACT AS A SYNERGIC MANNER TO INCREASE ADCC INVOLVED BY NK CELLS

A) Experimental Study

The aim of this example is to demonstrate on clinical samples of blood of patients with non-Hodgkin B lymphoma that anti CD20 mAb as Ublituximab R603 potentiate the ADCC induced by NK001 demonstrating a synergetic action between NK001 and mAb.

Samples of patients come from Hemodiag collection, CHU Montpellier.

Cell Line:

Daudi: the Daudi line was derived from a 16-year-old male with Burkitt's lymphoma, Daudi expresses high level of CD20.

Clinical Samples:

Non-Hodgkin B lymphoma:

Mantle cell lymphoma (p44 et p15-30)

Marginal zone B cell lymphoma (p16-01 et p16-48)

Diffuse large B-cells lymphoma (p16-108)

Anti CD20 mAbs

UblituxiMAb R603 (afucosylated, TGTX)

RituxiMAb (Roche Genentech, as a standard control)

NK001

5 different batches of NK001 (from NK001-2 to NK001-6) were produced, amplified and activated for this study.

Experimental Design:

1—On Daudi cell line (incubation time is 4 h): Rituximab cytotoxicity: dose effect to choose the best concentration; ADCC with Rituximab+NK001 dose effect (1a) to determine the best E:T ratio and ADCC with NK001+Rituximab dose effect (1b) to confirm Rituximab concentration and gain of lysis as a synergy between NK001+Rituximab and not as an additive effect.

2—On clinical samples: mAb anti CD20 cytotoxicity (24 h at 10 g/ml)

3—ADCC with an E:T (effector: target) ratio of 5:1 using 10 g/ml of anti CD20 mAb, pre-incubated 15 min at room temperature and placed at 37° C. for 24 h.

4—ADCC with 5 different batches of NK001 production, example of 3 clinical samples, to demonstrate reproducibility of results.

Results

On Daudi Cell Line

Characterization of anti-CD20 mAb in our in vitro condition

1a) Rituximab Cytotoxicity: Dose Effect and ADCC with Rituximab+NK001 Dose Effect See FIGS. 15A and 15B and Table 6

TABLE 6

% gain of lysis obtained between the natural cytotoxicity of NK001 and the lysis induced by combination NK001 + anti CD20 mAb.

| Daudi Ratio E:T | % gain of lysis NK001 + Rituximab |
| --- | --- |
| 0.5:1 | 30.1 |
| 1:1 | 21.3 |
| 2:1 | 11.9 |
| 3:1 | 1.4 |

These experiments allow to determine the best concentration of anti CD20 mAb: 10 g/ml (see FIG. 15 B)

Concerning ADCC assays on Daudi cells we conclude that ratio Effector (NK): Target (Daudi) 0.5:1 and 1:1 are the most appropriate to see a gain of target lysis using combination of NK001+Rituximab. For these 2 ratio, % of gain of targets' lysis are superior to 2

1b) ADCC with NK001+Rituximab Dose Effect

See FIG. 16 and Table 7

% gain=(lysis "NK001+mAb"−lysis NK001)×100/lysis NK001

TABLE 7

ADCC with NK001 + Rituximab dose effect on Daudi cell line

| Daudi cell line [mAb] μg/ml | % gain NK001 + Rituximab |
| --- | --- |
| 10 | 29.4 |
| 5 | 13.1 |

TABLE 7-continued

ADCC with NK001 + Rituximab dose effect on Daudi cell line

| Daudi cell line [mAb] μg/ml | % gain NK001 + Rituximab |
| --- | --- |
| 1 | 7.7 |
| 0.1 | 12.2 |

The statistical test used is a student test (t-test) with p-value compared to NK001 alone.

p-value<0.05: *; p-value<0.01: ; p-value<0.001: *

This result comforts us to use an anti CD20 mAb concentration of 10 g/ml to observe the more relevant results.

2—mAb Anti CD20 Cytotoxicity on Clinical Sample

See FIG. 17

We have assayed 5 clinical samples. We do not have a high level of cytotoxicity of anti CD20 mAbs in our in vitro condition assay. The maximum level of lysis observed is 4% (R603). Moreover no significant difference is observed between R603 and Rituximab.

3—ADCC Induced by NK-001 in Synergy with Anti CD20 mAb

See FIG. 18 and Table 8

TABLE 8

% gain of lysis obtained between the natural cytotoxicity of NK001 and the lysis induced by combination NK001 + anti CD20 mAb on 5 clinical sample

| | % Gain | |
| --- | --- | --- |
| Samples | NK001 + R603 | NK001 + Rituximab |
| P16-48 | 94.7 | 54.4 |
| P16-108 | 98.5 | 100.8 |
| P15-30 | 94.5 | 75.2 |
| P44 | 86.0 | 60.2 |
| P16-01 | 45.2 | 45.0 |

To demonstrate synergy between NK001 and anti CD20 mAbs we have performed ADCC on 5 clinical samples. For all presented results E:T ratio is 5:1.

In our in vitro conditions assays, although we do not observe cytotoxicity of anti CD20 mAbs alone, we demonstrate an increase of specific lysis of target cells when NK001 are combined with anti CD20 mAbs, as mentioned in the table. The smaller % of gain of lysis observed is 45% and the maximum is 100%.

Regarding these results we can suggest that for all the clinical samples we have a clear synergy of action between NK001 and anti CD20 mAbs.

4—ADCC with 5 Lots of NK001: Reproducibility of Results

See FIGS. 19A-19 C and (voir FIG. 5A-5C (Doc 6/01 de 8 pages sur Rituxi/R603)

We performed ADCC with 5 batches of NK001 production on clinical samples. We present results obtained for 3 clinical samples.

We confirm having a reproducibility of the results using different lots of NK001 and a similar efficacy between R603 and Rituximab.

The higher difference observed is for the clinical sample "p44" between batches NK001-2 and NK001-4, with 25.5% of difference.

For "p15-30", the mean difference between NK001-n+Rituximab is 10.2% and results obtained have a dispersion (SD) of 8.54. For "p15-30", the mean difference between NK001-n+R603 is 7.9% and results obtained have a dispersion (SD) of 6.4.

For "p44", the mean difference between NK001-n+Rituximab is 8.9% and results obtained have a dispersion (SD) of 7. For "p15-30", the mean difference between NK001-n+R603 is 13.4% and results obtained have a dispersion (SD) of 10.5.

For "p16-01", the mean difference between NK001-n+Rituximab is 6.1% and results obtained have a dispersion (SD) of 5. For "p16-01", the mean difference between NK001-n+R603 is 8.1% and results obtained have a dispersion (SD) of 6.8

Conclusion

On Daudi cell line (high CD20), 0.5:1 and 1:1 E:T ratio appear to be the most appropriate for conducting ADCC assays and for getting a difference of target lysis between treatment with NK001 alone vs NK001 combined with monoclonal antibodies.

In our in vitro conditions, to observe a positive dose effect of anti CD20 mAbs in ADCC, the minimal effective concentration is 10 µg/ml.

On clinical samples, association of NK001 with anti CD20 mAbs increases lysis of tumor cells compare to results obtain with NK001 cytotoxicity. Indeed, we calculated the % of gain of targets' lysis and obtained a minimum of 45% and a maximum of 100% of gain of lysis.

We do not observe any significant difference of efficacy between Ublituximab R603 and Rituximab.

So we can conclude that we have demonstrated a synergy of action between NK001 and anti CD20 mAbs.

Then we performed ADCC with 5 different batches of NK001 on clinical samples and observed a reproducibility of the results using different lots of NK001 and similar efficacy between UblituxiMAb R603 and Rituximab. The dispersion (Standard Deviation) of the % of lysis obtained with 5 lots of NK001 (+mAbs) is comprised between 5 and 10 which easily acceptable.

In our in vitro assay conditions we do not observe an important lysis of tumor cells induced by treatment of anti CD20 mAb alone.

Response to treatment depend on patients but are independent of the type of NH B lymphoma.

In the context of NK001 project, we set up a methodology to study the efficacy of NK001+mAb anti CD20 combination therapy on both cell cultures and on biological samples of patients (hematological cancers).

This methodology and its technology can be transposed with other types of monoclonal antibodies, either with new targets for hematological or solid cancer.

EXAMPLE 10: ANTI CD20 RITUXIMAB AND TG20: BINDING, CYTOTOXICITY AND INDUCED ADCC

Experimental Study
Samples of patients come from Hemodiag collection, CHU Montpellier.
Cell Lines
  Daudi: the Daudi line was derived from a 16-year-old male with Burkitt's lymphoma, Daudi expresses high level of CD20.
  Raji: the Raji line of lymphoblast-like cells was established from a Burkitt's lymphoma of an 11-year-old male. Raji expresses a low level of CD20.
  Ri-1: The cell line Ri-1 has been established from the peripheral blood of a 48-year-old female patient with B-cell lymphoma.
  SUDHL4: The cell line SUDHL4 has been established from the peritoneal effusion of a 38-year-old man with B-NHL (diffuse large cell, cleaved cell type).
  HL60: HL-60 is a promyelocytic cell line. Peripheral blood leukocytes were obtained by leukopheresis from a 36-year-old Caucasian female with acute promyelocytic leukemia. HL60 does not express CD20 (negative control)
Clinical Samples:
  Non-Hodgkin B lymphoma:
  Diffuse large B-cells lymphoma (p16-108 et p45)
  Mantle cell lymphoma (p44 et p15-30)
  Marginal zone B cell lymphoma (p16-01 et p16-48)
  Chronic lymphocytic leukemia:
  BCLL (p46 et p53)
Anti CD20 mAbs
  TG20 (afucosylated, LFB)
  RituxiMAb (Roche Genentech, as a standard control)
NK001
  6 different batches of NK001 (from NK001-1 to NK001-6) were produced, amplified and activated for this study.
Experimental Design:
  1—Anti CD20 mAb binding on NK-001 (1a) and Daudi, Raji cell lines: direct binding (1b) with a human Ig antibody and analyze of CD20 inhibition (1c).
  2—Quantification of apoptotic cells (Daudi, Raji) after 24 h incubation of anti CD20 mAb.
  3—Study of Complement Dependent Cytotoxicity (CDC) after 24 h incubation of anti CD20 mAb+20% of human serum on Daudi, Ri-1 and SUDHL4 cell lines.
  4—On Daudi cell line: mAb anti CD20 cytotoxicity: dose effect (4a) to choose the best concentration and ADCC with anti CD20 mAb+NK001 dose effect (4b) to determine the best E:T ratio.
  5—On Daudi cell line, ADCC with NK001+mAb anti CD20 dose effect to prove synergy of action or additive effect.
  6—On cell lines (Daudi, Raji, Ri-1, SUDHL4 and HL60 as a negative control): mAb anti CD20 cytotoxicity (6a) using 10 µg/ml and ADCC (6b) with an E:T ratio of 1:1 using 10 µg/ml of anti CD20 mAb, pre-incubated 15 min at room temperature and placed at 37° C. for 4 h. This experiment is done to determine the background and the acceptable % of gain of lysis for the rest of the study.
  7—mAb anti CD20 cytotoxicity (24 h at 10 µg/ml) on clinical samples.
  8—ADCC on clinical samples with an E:T ratio of 5:1 using 10 µg/ml of anti CD20 mAb, pre-incubated 15 min at room temperature and placed at 37° C. for 24 h.
Results
NK001
1a—Anti CD20 mAb Binding on NK001 (See FIG. 20))
  As TG20 is an afucosylated mAb, we observed a better binding to the CD16 of NK001 than Rituximab. This result was expected.
Cell Lines: Characterization of Anti CD20 mAb
1b—Direct Binding Analyses (hIg) (See FIGS. 21A and 21B)
  We do not observe any difference of binding on Daudi (high CD20) or on Raji (low CD20) between TG20 and Rituximab.
  For Daudi, EC50 [TG20]=75.6 ng/ml and EC50 [Rituximab]=105 ng/ml.

And for Raji, EC50 [TG20]=229 ng/ml and EC50 [Rituximab]=230 ng/ml.

1c—Binding Analyses by Inhibition of CD20 Labelling (See FIGS. 22A and 22B)

We do not observe any difference of CD20 inhibition on Daudi (high CD20) or on Raji (low CD20) cells between TG20 and Rituximab.

For Daudi, EC50 [TG20]=4 µg/ml and EC50 [Rituximab]=3.4 µg/ml.

And for Raji, EC50 [TG20]=5 µg/ml and EC50 [Rituximab]=3.7 µg/ml.

These results are consistent with the literature.

2—Quantification of Apoptotic Cells (See FIGS. 23A and 23B)

Apoptosis of cell lines slightly increases in proportion to the dose of anti CD20 mAb after 24 h of incubation.

3—Complement Dependent Cytotoxicity (CDC) (See FIGS. 24A, 24B and 24C)

Complement dependent cytotoxicity is more important when concentration of anti CD20 mAb increases.

We still do not observe any significant difference between TG20 and Rituximab.

4a—Cytotoxicity of Anti CD20 mAb: Dose Effect (See FIG. 25 and Table 9)

TABLE 9

| Daudi/[mAb] | % Lysis | |
|---|---|---|
| µg/ml | NK001 + TG20 | NK0021 = Rituximab |
| 0.1 | 9.6 | 7.1 |
| 1 | 10.1 | 6.7 |
| 5 | 12.6 | 12.2 |
| 10 | 18 | 17 |

This experiment permits to determine the best concentration of anti CD20 mAb: 10 µg/ml 4b—ADCC Induced by NK-001+Anti CD20 mAb [10 µg/Ml]: NK001 Dose Effect (See FIG. 26 and Table 10)

TABLE 10

| Daudi/[mAb] | % Gain | |
|---|---|---|
| µg/ml | NK001 + TG20 | NK001 + Rituximab |
| 10 | 30.0 | 29.4 |
| 5 | 13.1 | 13.1 |
| 1 | 5.4 | 7.7 |
| 0.1 | 10.4 | 12.2 |

The statistical test used is a student test (t-test) with p-value compared to NK001 alone.

p-value<0.05: *; p-value<0.01: ; p-value<0.001: *

Concerning ADCC assays on cell lines we conclude that ratio Effector (NK): Target (cell line) 0.5:1 and 1:1 are the most appropriate to see a gain of target lysis using combination of NK001+mAbs. For these 2 ratio, % of gain of targets' lysis are superior to 20%.

In conclusion, for the rest of the study, we are using an E:T ratio of 1:1 and a concentration of anti CD20 mAb=10 µg/ml.

5—ADCC Induced by NK-001+Anti CD20 mAb: mAb Dose Effect (See FIG. 27 and Table 11

TABLE 11

| Daudi/ | % Gain | |
|---|---|---|
| Ratio E:T | NK001 + TG20 | NK0021 = Rituximab |
| 0.5:1 | 30.6 | 30.1 |
| 1:1 | 23.5 | 21.3 |
| 2:1 | 12.2 | 11.9 |
| 3:1 | 5.0 | 1.4 |

This experiment allows to determine if the % of gain of lysis is due to a cumulative effect or a synergetic action between NK001+anti CD20 mAbs.

The statistical test used is a student test (t-test) with p-value compared to NK001 alone.

p-value<0.05: *; p-value<0.01: ; p-value<0.001: *

This result comforts us to use an anti CD20 mAb concentration of 10 µg/ml to observe the more relevant results.

6a—Cytotoxicity of Anti CD20 mAb: Cell Lines (See FIG. 28 and Table 12)

TABLE 12

| | % Lysis | |
|---|---|---|
| Cell lines | TG20 | Rituximab |
| Daudi | 16 | 14.9 |
| Raji | 12.2 | 9.7 |
| Ri-1 | 12 | 8.8 |
| SUDHL4 | 12.3 | 12.9 |
| HL60 | 2.5 | 2 |

In CD20 positive cell lines we only observe a weak cytotoxicity of CD20 mAb for 24 h.

The maximum of lyse obtained was 16% (TG20) and the minimum was 8.8% (Rituximab).

HL60 is a negative control and correspond to the background.

We do not observe significant difference between TG20 and Rituximab.

6b—ADCC Induced by NK-001 in Synergy with Anti CD20 mAb (See FIG. 29 and Table 13)

TABLE 13

| | % Lysis | |
|---|---|---|
| Cell lines | NK001 + TG20 | NK001 + Rituximab |
| Daudi | 26.0 | 25.4 |
| Raji | 45.3 | 41.1 |
| Ri-1 | 64.8 | 51.7 |
| SUDHL4 | 30.2 | 26.5 |
| HL60 | 20.1 | 10.9 |

The statistical test used is a student test (t-test) with p-value compared to NK001 alone.

p-value<0.05: *; p-value<0.01: ; p-value<0.001: *

Table of % of gain of targets' lysis of ADCC results (NK001+mAb) compare to natural NK001 cytotoxicity:

NB: formula of % gain explain end of the Example.

Regarding statistical analysis and negative control HL60, we can suggest for the following study that if the % of gain when NK001 is combined with mAb is less than 20%, there is no synergetic action of NK001 and mAb.

Clinical Samples

7—Anti CD20 mAbs Cytotoxicity (See FIG. 30)

We have assayed 8 clinical samples (detailed in III-Report content). As observed on cell lines, we do not have a high level of cytotoxicity of anti CD20 mAbs in our in vitro condition assay. The maximum level of lysis observed is 11.2% (Rituximab) and the minimum is 1.7% (TG20). Moreover no significant difference is observed between TG20 and Rituximab.

8—ADCC Induced by NK-001+Anti CD20 mAbs (See FIG. 31 and Table 14)

To demonstrate synergy between NK001 and anti CD20 mAbs we have performed ADCC on 8 clinical samples. For all presented results E:T ratio is 5:1.

TABLE 14

| | % Lysis | |
| --- | --- | --- |
| Patients | NK001 + TG20 | NK001 + Rituximab |
| p46 | 145.9 | 149.4 |
| p16-18 | 94.9 | 99.2 |
| p53 | 60.7 | 45.7 |
| p15-30 | 124.5 | 136.1 |
| p44 | 118.1 | 141.2 |
| p45 | 40.7 | 55.9 |
| p16-108 | 24.5 | 38.1 |
| p16-108 | 19.1 | 25.8 |

For clinical samples we need to use a higher E:T ratio (5:1) than which one is used for cell lines (0.5:1 or 1:1) and an incubation of 24 h to observe a relative high cytotoxicity of NK001 alone. Other E:T ratio were tested, data not shown.

In our in vitro conditions assays, although we do not observe cytotoxicity of anti CD20 mAbs alone, we demonstrate an increase of specific lysis of target cells when NK001 are combined with anti CD20 mAbs, as mentioned in the table. The inferior limit is 20% and the maximum of gain of targets' lysis observed is 150%.

Regarding the characterization done on cell lines we can suggest that for all the clinical samples we have a clear synergy of action between NK001 and anti CD20 mAbs.

We performed ADCC with 6 batches of NK001 production on clinical samples. We present results obtained for 3 clinical samples.

As we fixed a limit of 20% of acceptable difference with the in vitro study made on cell lines, we can suggest that we have a reproducibility of the results using different lots of NK001 and similar efficacy between TG20 and Rituximab.

Conclusion

On NK001, TG20 is higher than binding of Rituximab. TG20 is an afucosylated mAb so its fixation to CD16 receptor is more effective.

The binding of TG20 and Rituximab was tested on Daudi (high CD20) and Raji (low CD20) lines. On Daudi, the EC50 for TG20 is 75.6 ng/ml and the EC50 for Rituximab is 105 ng/ml. On Raji, the EC50 of the TG20 is 229 ng/ml and the EC50 of the Rituximab is 230 ng/ml. The small differences observed are not significant. The EC50 is to reach 50% of mAb fixation on cell surface.

The inhibition of CD20 was also tested on Daudi (high CD20) and Raji (low CD20) lines.

On Daudi, the EC50 for TG20 is 4 µg/ml and the EC50 for Rituximab is 3.4 g/ml.

On Raji, the EC50 of TG20 is 5 µg/ml and the EC50 of Rituximab is 3.7 µg/ml.

The EC50 is to achieve 50% inhibition of CD20 labelling on cell surface.

The results are consistent with the literature and the small differences observed are not significant.

Apoptosis of cell lines slightly increases in proportion to the dose of anti CD20 mAb after 24 h of incubation.

Also, complement dependent cytotoxicity is more important when concentration of anti CD20 mAb increases.

We do not observe any significant difference between TG20 and Rituximab.

On Daudi cell line, we first analyzed the lysis induced by dose effect of anti-CD20 mAb and chose 10 µg/ml as a work concentration. Then we performed a dose escalation of E:T ratio for ADCC assay and 0.5:1 and 1:1 E:T ratio appear to be the most appropriate for conducting ADCC assays and for getting a difference of target lysis between treatment with NK001 alone vs NK001 combined with monoclonal antibodies. Based on these results and statistical analysis we suggest that we have a synergetic action between NK001+ and anti CD20 mAb that we also assayed on other CD20 positive cell lines.

In our in vitro conditions, to observe a positive dose effect of anti CD20 mAbs in ADCC, the minimal effective concentration is 10 µg/ml.

On HL60 cell line (CD20 neg) no significant synergetic action of anti-CD20 combined with NK001 is observed, which is normal as a negative control of ADCC. This result permits to fix a limit of 20% of difference between % of gain of target lysis obtained with NK001 alone and NK001+anti CD20 mAbs.

Moreover in all assays performed, TG20 seems to be as effective as the standard Rituximab control.

On clinical samples, association of NK001 with anti CD20 mAbs increases lysis of tumor cells compare to results obtain with NK001 alone, as observed on cell lines. But, we need to use a higher E:T ratio (5:1) than which one is used for cell lines (0.5:1 or 1:1) and an incubation of 24 h to observe a relative high cytotoxicity of NK001 alone.

We calculated the % of gain of targets' lysis and obtained an inferior limit of 20% (determine as acceptable by study on cell lines) and a maximum of 150% of gain of lysis.

So we can conclude that we have demonstrated a synergy of action between NK001 and anti CD20 mAbs.

Then we performed ADCC with 6 different batches of NK001 on clinical samples and observed a reproducibility of the results using different lots of NK001 and similar efficacy between TG20 and Rituximab.

Response to treatment depend on patients but are independent of the type of NH B lymphoma.

With our in vitro assay conditions we do not observe an important lyse of tumor cells induced by treatment of anti CD20 mAb alone.

These results show the efficacy of NK001+mAb anti CD20 combination therapy on both cell cultures and on biological samples of patients (hematological cancers).

Abbreviation

ADCC: antibody dependent cellular cytotoxicity
CDC: complement dependent cytotoxicity
EC50: Half maximal effective concentration
E:T: Effector (=NK001): Target (cell lines or tumor cells)
IV: intra venous
mAb: monoclonal antibody
NSG: NOD scid gamma NH: Non Hodgkin
NK: natural killer cell
Statistical analyses are basic Student t-test.

% gain=(lysis "NK001+mAb"—lysis NK001)×100
lysis NK001

EXAMPLE 11: ANTI HER 2 ANTIBODIES ACT AS A SYNERGIC MANNER TO INCREASE ADCC INVOLVED BY NK CELLS

It is demonstrated here that the efficacy of cell therapeutic treatment for solid cancer expressing Her2/neu receptor as some breast or ovarian cancer can be increased by association of NK001 cells with anti Her2/neu monoclonal antibodies (mAb) which act in synergic action.

Indeed, NK cells are able to interact with cytotoxic mAb and kill cells recognized by these mAbs. This own property of NK cells is known as "Antibody Dependent Cellular Cytotoxicity" (ADCC).

Material and Method

Experimental Study—Anti Her2 mAb Approach

One of the main characteristic of NK001 cells production process is getting a high percentage of CD16 receptor (FcγRIII) on NK001 which is in favor of a high level of cytotoxicity and could be potentiated with mAb association (ADCC).

Demonstration, in vitro on tumor cell lines expressing Her2/neu receptor that anti Her2/neu mAb as Trastuzumab (Roche, Genentech) or Herceptin-like (LFB US) potentiate the ADCC induced by NK001.

Cell Lines
  SKBR3: The SKBR3 line was derived from metastatic pleural effusion of a 43 years old female with a breast adenocarcinoma. SKBR3 are epithelial and adherent cells.
  SKOV3: The SKOV3 line was derived from the ovary tissue (ascites of an adenocarcinoma) of a 64 years old female. SKOV3 are epithelial and adherent cells.
Anti Her2 mAbs
Herceptin Like (LFB US)
  Herceptin-like, is a biosimilar antibody of the Trastuzumab ("Herceptin™") which is produced in the milk of transgenic goats, It has been obtained using the rPRO™ platform, a disruptive innovation, which uses genetic recombination to express a protein in mammal milk, particularly goat milk, that can be used in human medicine. The protein is then isolated, purified and made safe using the highest pharmaceutical standards. According to LFB US, rPRO™ is a robust, productive technology, with an excellent economic profile, largely because it increases production greatly while keeping costs down.
  For the process of preparation of monoclonal antibody (Mab) from milk of transgenic goats se for example U.S. Pat. No. 8,173,860, Meade et al. May 8, 2012,
  GTC Biotherapeutics) and for the humanized trastuzumab MAb sequence, the U.S. Pat. No. 5,821,337 (Carter et al., Oct. 13, 1998, Roche/Genentech).
Trastuzumab (Roche Genentech)
NK001 (Emercell)
  2 different batches of NK001 (NK001-1 and NK001-2) were produced, amplified and activated for this study.

Experimental Design:
  1—Anti Her2 mAbs binding on NK-001: direct binding with a human IgG antibody.
  2—Anti Her2 mAbs cytotoxicity on SKOV3 and SKBR3, 3 h, 10 g/ml.
  3—ADCC with 10 g/ml of anti Her2 mAbs+NK001 with E:T ratio as 5:1, 3 h.
  Analysis by flow cytometry and microscopy.
Results
NK001
1—Anti Her2 mAbs Binding on NK001 (See FIG. 33)
  Herceptin-like and Trastuzumab binding to the CD16 of NK001 are observed, with a better binding for Herceptin-like than Trastuzumab.
2—Anti-Her2 mAbs Cytotoxicity (See FIG. 34)
  This experiment permits to determine the lysis induced by 10 g/ml of anti Her2 mAbs for 3 h in order to compare to ADCC. In these in vitro conditions we observed a weak cytotoxicity of anti Her2 mAbs on SKBR3 and SKOV3. SKOV3 seems to be more sensitive to anti Her2 mAb treatment.
3—ADCC Induced by NK-001+Anti Her2 mAb [10 µg/Ml]; E:T Ratio is 5:1, 3 h
  (See FIGS. 35A, 35B)

TABLE 15

| % Gain of Lysis | % gain of lysis | | | |
|---|---|---|---|---|
| | SKBR3 | | SKOV3 | |
| | Mean | SD | Mean | SD |
| NK001 + Trastuzumab | 134.5 | 25.5 | 19.2 | 12.5 |
| NK001 + Herceptin-like | 121.1 | 28.3 | 88.4 | 10.3 |

On SKBR3 cell line, an important synergetic action between NK001 and anti-Her2 mAbs was observed, as a result of a gain of lysis of 134% for NK001+Trastuzumab and 121% for NK001+Herceptin-like. No difference was observed between both anti Her2 mAbs.

On SKOV3 cell line, an important synergetic action between NK001 and anti-Her2 mAbs was observed (See FIGS. 36 and 37)

Herceptin-like appears to be more efficient than Trastuzumab on SKOV3 cell lines.

Effector (NK001): Target (cells) ratio (E:T ratio) of 5:1 is acceptable for a cytotoxicity of 3 h at 37° C.

Conclusion

It can be concluded that a synergy of action has been demonstrated between NK001 and anti Her2 mAbs in 2 models of adherent tumor cell lines for anti-Her2 mAbs.

On NK001, binding of Herceptin like is higher than binding of Trastuzumab.

Then, ADCC assay was performed on SKBR3 and SKOV3 cell line, using 10 g/ml of anti-Her2 mAbs for 3 h at 37° C. The anti-Her2 mAbs were pre-incubated at room temperature for 15 minutes.

On SKBR3 no difference was observed between Trastuzumab and Herceptin like. Gain of lysis of NK001+ anti Her2 mAbs compare to natural cytotoxicity of NK001 was higher for SKBR3 than for SKOV3. However it seems that association of NK001+Herceptin-like is more efficient for SKOV3 cell line.

The invention claimed is:
1. A method for treating cancer comprising the administration to a subject in need of treatment for cancer of a therapeutically effective amount of a first composition and a second composition, wherein said first composition comprising a population of alloreactive natural killer cells (NK cells) which are derived from a mixture of at least n umbilical cord blood units (UCB units) pooled from two or more different donors, or a mixture of fraction thereof containing said NK cells, with n≥2; and said second composition comprising a monoclonal antibody or a specific binding fragment thereof directed to a cell receptor antigen of cells of said subject;

wherein the population of alloreactive NK cells comprised in said first composition are obtained by a method comprising:

(A) providing at least n umbilical cord blood units (UCB units), or fraction thereof, each UCB unit or fraction thereof comprising NK cells and T cells, with n≥2;

(B) pooling said at least n UCB units from two or more different donors, or pooled fraction thereof, and depleting said T cells to produce the population of cells comprising pooled NK cells;

(C) expanding and activating said pooled NK cells in a medium comprising accessory cells to produce a population of expanded activated NK cells; and (D) recovering said expanded activated NK cells; and wherein the pattern for major HLA class I groups genotype is the same in each of said n UCB units pooled from two or more different donors, or pooled fraction thereof, and is selected from the group consisting of HLA A3/A11, which is recognized by KIR3DL2; HLA Bw4, which recognized by KIR3DL1; HLA C group 1, which is recognized by KIR2DL2/3; and HLA C group 2, which is recognized by KIR2DL1; and wherein in step (C) said pooled NK cells and said accessory cells are HLA-KIR mismatched.

2. A method for treating cancer according to claim 1, wherein said first and second composition are administered simultaneously, separately or sequentially.

3. A method for treating cancer according to claim 1, wherein said cancer is selected from cancers overexpressing a cell receptor at the surface of the tumoral cells of the subject in need of the treatment, and wherein the monoclonal antibody of said second composition is directed against said receptor.

4. A method for treating cancer according to claim 1, wherein said second composition comprises a monoclonal antibody which is a low or non-fucosylated antibody.

5. A method for treating cancer according to claim 1, wherein said second composition comprises a monoclonal antibody selected the group consisting of anti-CD20, anti-HER2/Neu and anti-EGFR antibodies.

6. A method for treating cancer according to claim 1, wherein said second composition comprises a monoclonal antibody selected the group consisting of Ublituximab, Trastuzumab and Trastuzumab-like antibodies.

7. A method for treating cancer according to claim 1, wherein cancer to be treated are selected from the group of hematologic malignancy tumor cells, solid tumor cells or carcinoma cells, acute T cell leukemia cells, chronic myeloid lymphoma (CML) cells, acute myelogenous leukemia cells, chronic myelogenous leukemia (CML) cells, multiple myeloma cells, or lung, colon, prostate, glyoblastoma cancer.

8. The method of claim 1, wherein n is: 2<n≤100.

9. The method of claim 1, wherein n is: 3≤n≤50.

10. The method of claim 1, wherein said accessory cells are irradiated.

11. The method of claim 1, wherein said accessory cells are immortalized.

12. The method of claim 1, wherein said accessory cells are immortalized by Epstein Barr Virus (EBV) transformation.

13. The method of claim 1, wherein said accessory cells are cells from HLA-typed mammals.

14. The method of claim 1, wherein said provided UCB units are thawed UCB units from frozen stored UCB units.

15. The method of claim 1, wherein the pooled NK cells are expanded for from 9 to 28 days and the amplification factor for NK cells after the expanding is at least 100.

16. The method of claim 1, wherein the amplification factor for NK cells after the expanding is at least 300.

17. The method of claim 1, wherein in step A), each of the n UCB units are T cells depleted before the step B) of pooling.

* * * * *